US012714670B2

(12) United States Patent
Du et al.

(10) Patent No.: US 12,714,670 B2
(45) Date of Patent: Aug. 25, 2026

(54) CARBONYL LIPIDS AND LIPID NANOPARTICLE FORMULATIONS FOR DELIVERY OF NUCLEIC ACIDS

(71) Applicant: Acuitas Therapeutics, Inc., Vancouver (CA)

(72) Inventors: Xinyao Du, Richmond (CA); Steven M. Ansell, Vancouver (CA)

(73) Assignee: Acuitas Therapeutics, Inc., Vancouver (CA)

(*) Notice: Subject to any disclaimer, the term of this patent is extended or adjusted under 35 U.S.C. 154(b) by 82 days.

(21) Appl. No.: 18/482,574

(22) Filed: Oct. 6, 2023

(65) Prior Publication Data

US 2024/0122854 A1 Apr. 18, 2024

Related U.S. Application Data

(63) Continuation of application No. 16/608,610, filed as application No. PCT/US2018/029778 on Apr. 27, 2018, now Pat. No. 11,820,728.

(60) Provisional application No. 62/595,497, filed on Dec. 6, 2017, provisional application No. 62/546,227, filed on Aug. 16, 2017, provisional application No. 62/491,659, filed on Apr. 28, 2017, provisional application No. 62/491,664, filed on Apr. 28, 2017.

(51) Int. Cl.

| | |
|---|---|
| ***A61K 9/1271*** | (2025.01) |
| ***A61K 9/51*** | (2006.01) |
| ***A61K 47/14*** | (2017.01) |
| ***A61K 47/28*** | (2006.01) |
| ***A61K 47/34*** | (2017.01) |
| ***A61K 48/00*** | (2006.01) |
| ***C07C 229/24*** | (2006.01) |
| ***C07C 233/36*** | (2006.01) |
| ***C07C 237/06*** | (2006.01) |
| ***C07C 237/08*** | (2006.01) |
| *A61K 31/7105* | (2006.01) |

(52) U.S. Cl.

CPC .......... *A61K 9/1271* (2013.01); *A61K 9/5123* (2013.01); *A61K 47/14* (2013.01); *A61K 47/28* (2013.01); *A61K 47/34* (2013.01); *A61K 48/0008* (2013.01); *C07C 229/24* (2013.01); *C07C 233/36* (2013.01); *C07C 237/06* (2013.01); *C07C 237/08* (2013.01); *A61K 31/7105* (2013.01)

(58) Field of Classification Search

CPC ...... A61K 9/1271; A61K 47/14; A61K 47/28; A61K 47/34; A61K 48/0008; C07C 229/24; C07C 233/36

See application file for complete search history.

(56) References Cited

U.S. PATENT DOCUMENTS

| | | | |
|---|---|---|---|
| 2,411,662 | A | 11/1946 | Hans et al. |
| 2,856,420 | A | 10/1958 | Crawford, Jr. |
| 3,340,299 | A | 9/1967 | Lester et al. |
| 3,594,224 | A | 7/1971 | Peter |
| 3,729,564 | A | 4/1973 | Chang et al. |
| 3,838,991 | A | 10/1974 | Garth |
| 3,931,430 | A | 1/1976 | Tada et al. |
| 3,951,581 | A | 4/1976 | Nakayama et al. |
| 4,121,898 | A | 10/1978 | Kirschnek et al. |

(Continued)

FOREIGN PATENT DOCUMENTS

| | | | |
|---|---|---|---|
| CN | 102604115 | A | 7/2012 |
| CN | 102905763 | A | 1/2013 |

(Continued)

OTHER PUBLICATIONS

Akinc et al., "A combinatorial library of lipid-like materials for delivery of RNAi therapeutics," Nature Biotechnology 26(5):561-569, May 2008.

Akinc et al., "Targeted delivery of RNAi therapeutics with endogenous and exogenous ligand-based mechanisms," Mol. Ther. 18(7):1357-1364, 2010.

Alabi et al., "Multiparametric approach for the evaluation of lipid nanoparticles for siRNA delivery," PNAS 110(32):12881-12886, Aug. 6, 2013.

(Continued)

*Primary Examiner* — Kamal A Saeed
*Assistant Examiner* — Sagar Patel
(74) *Attorney, Agent, or Firm* — Seed Intellectual Property Law Group LLP

(57) ABSTRACT

Compounds are provided having one of the following structures (I) or (II):

(I)

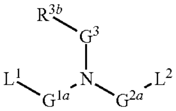

or (II)

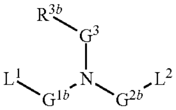

or a pharmaceutically acceptable salt, tautomer or stereoisomer thereof, wherein $R^{3a}$, $R^{3b}$, $L^1$, $L^2$, $G^{1a}$, $G^{1b}$, $G^{2a}$, $G^{2b}$ and $G^3$ are as defined herein. Use of the compounds as a component of lipid nanoparticle formulations for delivery of a therapeutic agent, compositions comprising the compounds and methods for their use and preparation are also provided.

22 Claims, No Drawings

(56) References Cited

U.S. PATENT DOCUMENTS 4,450,282 A 5/1984 Ritzer et al.
4,503,252 A 3/1985 Felder et al.
4,639,468 A 1/1987 Roncucci et al.
4,897,355 A 1/1990 Eppstein et al.
4,946,787 A 8/1990 Eppstein et al.
5,049,386 A 9/1991 Eppstein et al.
5,176,996 A 1/1993 Hogan et al.
5,389,221 A 2/1995 Jorgenson et al.
5,420,032 A 5/1995 Marshall et al.
5,422,251 A 6/1995 Fresco
5,527,524 A 6/1996 Tomalia et al.
5,705,385 A 1/1998 Bally et al.
5,744,335 A 4/1998 Wolff et al.
5,756,785 A 5/1998 O'Lenick, Jr.
5,759,230 A 6/1998 Chow et al.
5,789,538 A 8/1998 Rebar et al.
5,919,743 A 7/1999 O'Lenick, Jr.
5,925,523 A 7/1999 Dove et al.
5,965,542 A 10/1999 Wasan et al.
5,976,567 A 11/1999 Wheeler et al.
5,981,501 A 11/1999 Wheeler et al.
6,008,336 A 12/1999 Hanson et al.
6,013,453 A 1/2000 Choo et al.
6,013,813 A 1/2000 O'Lenick, Jr.
6,020,526 A 2/2000 Schwartz et al.
6,034,137 A 3/2000 Belloni et al.
6,077,509 A 6/2000 Weiner et al.
6,107,286 A 8/2000 Byk et al.
6,140,081 A 10/2000 Barbas
6,140,466 A 10/2000 Barbas, III et al.
6,200,759 B1 3/2001 Dove et al.
6,242,568 B1 6/2001 Barbas, III et al.
6,300,321 B1 10/2001 Scherman et al.
6,333,433 B1 12/2001 Banerjee et al.
6,410,248 B1 6/2002 Greisman et al.
6,410,328 B1 6/2002 Maclachlan et al.
6,443,610 B1 9/2002 Shechter et al.
6,453,242 B1 9/2002 Eisenberg et al.
6,458,381 B1 10/2002 Sourovoi et al.
6,479,626 B1 11/2002 Kim et al.
6,503,717 B2 1/2003 Case et al.
6,534,018 B1 3/2003 Baker et al.
6,534,261 B1 3/2003 Cox, III et al.
6,534,484 B1 3/2003 Wheeler et al.
6,586,410 B1 7/2003 Wheeler et al.
6,599,692 B1 7/2003 Case et al.
6,607,882 B1 8/2003 Cox, III et al.
6,620,794 B1 9/2003 O'Lenick, Jr. et al.
6,689,558 B2 2/2004 Case
6,723,551 B2 4/2004 Kotin et al.
6,794,136 B1 9/2004 Eisenberg et al.
6,815,432 B2 11/2004 Wheeler et al.
6,824,978 B1 11/2004 Cox, III et al.
6,833,252 B1 12/2004 Dujon et al.
6,858,224 B2 2/2005 Wheeler et al.
6,903,185 B2 6/2005 Kim et al.
6,933,113 B2 8/2005 Case et al.
6,979,539 B2 12/2005 Cox, III et al.
6,986,902 B1 1/2006 Chen et al.
6,989,264 B2 1/2006 Atkinson et al.
7,013,219 B2 3/2006 Case et al.
7,030,215 B2 4/2006 Liu et al.
7,067,317 B2 6/2006 Rebar et al.
7,070,934 B2 7/2006 Cox, III et al.
7,074,596 B2 7/2006 Darzynkiewicz et al.
7,112,337 B2 9/2006 Huang et al.
7,153,949 B2 12/2006 Kim et al.
7,163,824 B2 1/2007 Cox, III et al.
7,217,509 B2 5/2007 Wolffe et al.
7,253,273 B2 8/2007 Collingwood
7,262,054 B2 8/2007 Jamieson et al.
7,271,002 B2 9/2007 Kotin et al.
7,361,635 B2 4/2008 Miller et al.
7,404,969 B2 7/2008 Chen et al.
7,470,781 B2 12/2008 Crouzet et al.
7,745,651 B2 6/2010 Heyes et al.
7,799,565 B2 9/2010 MacLachlan et al.
7,803,397 B2 9/2010 Heyes et al.
7,811,602 B2 10/2010 Cullis et al.
7,893,302 B2 2/2011 Chen et al.
7,901,708 B2 3/2011 MacLachlan et al.
7,951,925 B2 5/2011 Ando et al.
7,982,027 B2 7/2011 MacLachlan et al.
8,034,376 B2 10/2011 Manoharan et al.
8,158,601 B2 4/2012 Chen et al.
8,206,747 B2 6/2012 Zale et al.
8,278,036 B2 10/2012 Kariko et al.
8,283,333 B2 10/2012 Yaworski et al.
8,293,276 B2 10/2012 Troiano et al.
8,318,208 B1 11/2012 Zale et al.
8,318,211 B2 11/2012 Zale et al.
8,329,070 B2 12/2012 MacLachlan et al.
8,466,122 B2 6/2013 Heyes et al.
8,569,256 B2 10/2013 Heyes et al.
8,575,123 B2 11/2013 Manoharan et al.
8,642,076 B2 2/2014 Manoharan et al.
8,691,750 B2 4/2014 Constien et al.
8,722,082 B2 5/2014 Manoharan et al.
8,748,089 B2 6/2014 Kariko et al.
8,754,062 B2 6/2014 de Fougerolles et al.
8,802,644 B2 8/2014 Chen et al.
8,822,668 B2 9/2014 Yaworski et al.
8,835,108 B2 9/2014 Kariko et al.
9,012,498 B2 4/2015 Manoharan et al.
9,139,554 B2 9/2015 Hope et al.
9,352,042 B2 5/2016 Heyes et al.
9,604,908 B2 3/2017 Stanton et al.
9,682,922 B2 6/2017 Manoharan et al.
9,737,619 B2 8/2017 Ansell et al.
9,738,593 B2 8/2017 Ansell et al.
9,750,824 B2 9/2017 Kariko et al.
9,795,566 B2 10/2017 Oya et al.
9,873,894 B2 1/2018 Conway et al.
10,106,490 B2 10/2018 Du
10,117,941 B2 11/2018 Manoharan et al.
10,144,725 B2 12/2018 Brown
10,166,298 B2 1/2019 Ansell et al.
10,221,127 B2 3/2019 Du et al.
10,238,731 B2 3/2019 Ciaramella et al.
10,307,490 B2 6/2019 Lee et al.
10,682,374 B2 6/2020 Dong et al.
10,723,692 B2 7/2020 Ansell et al.
11,040,112 B2 6/2021 Ansell et al.
11,168,051 B2 11/2021 Du et al.
11,241,490 B2 2/2022 Weissman et al.
11,357,856 B2 6/2022 Ansell et al.
11,453,639 B2 9/2022 Du
11,472,766 B2 10/2022 Ying
11,524,932 B2 12/2022 Du
11,542,225 B2 1/2023 Du
11,583,504 B2 2/2023 Brader
11,597,698 B2 3/2023 Benenato et al.
11,634,379 B2 4/2023 Ansell et al.
11,639,329 B2 5/2023 Du
11,648,324 B2 5/2023 Ansell et al.
11,712,481 B2 8/2023 Hope et al.
11,820,728 B2 11/2023 Du et al.
11,976,019 B2 5/2024 Gatenyo et al.
12,065,396 B2 8/2024 Du
12,129,223 B2 10/2024 Du et al.
12,138,305 B2 11/2024 Weissman et al.
12,151,996 B2 11/2024 Du
12,329,857 B2 6/2025 Barbosa et al.
12,410,121 B2 9/2025 Gatenyo et al.
12,491,261 B2 12/2025 Hope et al.
12,583,816 B2 3/2026 Hansell
2003/0031704 A1 2/2003 Huang et al.
2003/0049310 A1 3/2003 Gao
2003/0073640 A1 4/2003 Beigelman et al.
2003/0153081 A1 8/2003 Tagawa et al.
2004/0142025 A1 7/2004 MacLachlan et al.
2004/0142474 A1 7/2004 Mahato et al.
2004/0157149 A1 8/2004 Hofmann
2005/0064595 A1 3/2005 MacLachlan et al.

(56) References Cited

U.S. PATENT DOCUMENTS

2005/0222064 A1 10/2005 Vargeese et al.
2005/0250723 A1 11/2005 Hoerr et al.
2006/0083780 A1 4/2006 Heyes et al.
2006/0100177 A1 5/2006 Nishimura et al.
2006/0188490 A1 8/2006 Hoerr et al.
2006/0188987 A1 8/2006 Guschin et al.
2006/0240554 A1 10/2006 Chen et al.
2007/0042031 A1 2/2007 MacLachlan et al.
2008/0020058 A1 1/2008 Chen et al.
2008/0025944 A1 1/2008 Hoerr et al.
2009/0086558 A1 4/2009 Do
2009/0209037 A1 8/2009 Tagawa et al.
2009/0247608 A1 10/2009 Manoharan et al.
2009/0263407 A1 10/2009 Dande et al.
2009/0285881 A1 11/2009 Dande et al.
2009/0324584 A1 12/2009 Hoerr et al.
2010/0036115 A1 2/2010 Beigelman et al.
2010/0068285 A1 3/2010 Zale et al.
2010/0068286 A1 3/2010 Troiano et al.
2010/0069426 A1 3/2010 Zale et al.
2010/0087337 A1 4/2010 Dewitt
2010/0104645 A1 4/2010 Ali et al.
2010/0104655 A1 4/2010 Zale et al.
2010/0189729 A1 7/2010 Hoerr et al.
2010/0203076 A1 8/2010 Fotin-Mleczek et al.
2010/0285112 A1 11/2010 Novobrantseva et al.
2010/0291156 A1 11/2010 Barner et al.
2010/0305196 A1 12/2010 Probst et al.
2010/0324120 A1 12/2010 Chen et al.
2011/0045473 A1 2/2011 De Fougerolles et al.
2011/0091525 A1 4/2011 Heyes et al.
2011/0097720 A1 4/2011 Ciufolini et al.
2011/0152175 A1 6/2011 Lipkowska et al.
2011/0200582 A1 8/2011 Baryza et al.
2011/0250225 A1 10/2011 Fotin-Mleczek et al.
2011/0256175 A1 10/2011 Hope et al.
2011/0262491 A1 10/2011 Keegan et al.
2011/0262527 A1 10/2011 Heyes et al.
2011/0274759 A1 11/2011 Troiano et al.
2011/0294717 A1 12/2011 Ali et al.
2011/0300205 A1 12/2011 Geall et al.
2011/0305770 A1 12/2011 Zhao et al.
2011/0311582 A1 12/2011 Manoharan et al.
2011/0311583 A1 12/2011 Manoharan et al.
2012/0004293 A1 1/2012 Zale et al.
2012/0009222 A1 1/2012 Nguyen et al.
2012/0021043 A1 1/2012 Kramps et al.
2012/0027796 A1 2/2012 Manoharan et al.
2012/0027803 A1 2/2012 Manoharan et al.
2012/0046478 A1 2/2012 Manoharan et al.
2012/0058144 A1 3/2012 Manoharan et al.
2012/0058188 A1 3/2012 MacLachlan et al.
2012/0095075 A1 4/2012 Manoharan et al.
2012/0101148 A1 4/2012 Aking et al.
2012/0128760 A1 5/2012 Manoharan et al.
2012/0172411 A1 7/2012 Heyes et al.
2012/0177724 A1 7/2012 Irvine et al.
2012/0178702 A1 7/2012 Huang et al.
2012/0183602 A1 7/2012 Chen et al.
2012/0202871 A1 8/2012 Heyes et al.
2012/0207845 A1 8/2012 Sung et al.
2012/0225434 A1 9/2012 Ciufolini et al.
2012/0244207 A1 9/2012 Fitzgerald et al.
2012/0251618 A1 10/2012 Schrum et al.
2012/0264810 A1 10/2012 Lin et al.
2012/0276209 A1 11/2012 Cullis et al.
2012/0288541 A1 11/2012 Zale et al.
2012/0295832 A1 11/2012 Constien et al.
2013/0017223 A1 1/2013 Hope et al.
2013/0022649 A1 1/2013 Yaworski et al.
2013/0064894 A1 3/2013 Martin et al.
2013/0108685 A1 5/2013 Kuboyama et al.
2013/0122104 A1 5/2013 Yaworski et al.
2013/0123338 A1 5/2013 Heyes et al.
2013/0129754 A1 5/2013 Thess et al.
2013/0129811 A1 5/2013 Kuboyama et al.
2013/0164400 A1 6/2013 Knopov et al.
2013/0177960 A1 7/2013 Rebar
2013/0259879 A1 10/2013 Baumhof et al.
2013/0261172 A1 10/2013 Kariko et al.
2013/0266640 A1 10/2013 de Fougerolles et al.
2013/0280283 A1 10/2013 Lorenz et al.
2013/0280305 A1 10/2013 Kuboyama et al.
2013/0295043 A1 11/2013 Kallen et al.
2013/0323269 A1 12/2013 Manoharan et al.
2013/0336998 A1 12/2013 Kallen et al.
2013/0338210 A1 12/2013 Manoharan et al.
2014/0044772 A1 2/2014 MacLachlan et al.
2014/0045913 A1 2/2014 Kuboyama et al.
2014/0087036 A1 3/2014 Organ et al.
2014/0121393 A1 5/2014 Manoharan et al.
2014/0134260 A1 5/2014 Heyes et al.
2014/0179761 A1 6/2014 Manoharan et al.
2014/0256785 A1 9/2014 Manoharan et al.
2014/0294937 A1 10/2014 MacLachlan et al.
2014/0295449 A1 10/2014 Ciufolini et al.
2014/0308304 A1 10/2014 Manoharan et al.
2014/0309277 A1 10/2014 Baryza et al.
2014/0323548 A1 10/2014 Budzik et al.
2015/0037326 A1 2/2015 Butler-Ransohoff et al.
2015/0050302 A1 2/2015 Thess
2015/0057340 A1 2/2015 Thess et al.
2015/0093413 A1 4/2015 Thess et al.
2015/0118183 A1 4/2015 Baumhof
2015/0118264 A1 4/2015 Baumhof et al.
2015/0165006 A1 6/2015 Thess et al.
2015/0184195 A1 7/2015 Thess et al.
2015/0203446 A1 7/2015 Manoharan et al.
2015/0218554 A1 8/2015 Thess
2015/0306249 A1 10/2015 Baumhof et al.
2015/0329474 A1 11/2015 Shintou et al.
2016/0009637 A1 1/2016 Manoharan et al.
2016/0095924 A1 4/2016 Hope et al.
2016/0106842 A1 4/2016 Baryza et al.
2016/0130345 A1 5/2016 Fotin-Mleczek et al.
2016/0151284 A1 6/2016 Heyes et al.
2016/0166668 A1 6/2016 Kallen et al.
2016/0166678 A1 6/2016 Kallen et al.
2016/0166710 A1 6/2016 Baumhof
2016/0166711 A1 6/2016 Schnee et al.
2016/0168207 A1 6/2016 Kramps et al.
2016/0235864 A1 8/2016 Schlake et al.
2016/0243255 A1 8/2016 Nechev et al.
2016/0263278 A1 9/2016 Grinstaff et al.
2016/0304883 A1 10/2016 Grund et al.
2016/0361411 A1 12/2016 Gindy et al.
2017/0027803 A1 2/2017 Agrawal et al.
2017/0029847 A1 2/2017 Thess
2017/0100682 A1 4/2017 Wikfors
2017/0119667 A1 5/2017 Oya et al.
2017/0248502 A1 8/2017 Organ et al.
2017/0252430 A1 9/2017 Fotin-Mleczek et al.
2017/0266292 A1 9/2017 Luo et al.
2017/0326225 A1 11/2017 Rauch et al.
2018/0043320 A1 2/2018 Ramsay et al.
2018/0044687 A1 2/2018 Thess et al.
2018/0088091 A1 3/2018 Cormier et al.
2018/0125952 A1 5/2018 Fotin-Mleczek et al.
2018/0126003 A1 5/2018 Hoerr
2018/0147146 A1 5/2018 Eber et al.
2018/0148727 A1 5/2018 Grund et al.
2018/0195954 A1 7/2018 Strande et al.
2018/0214537 A1 8/2018 Mutzke et al.
2018/0237786 A1 8/2018 Schlake et al.
2018/0271795 A1 9/2018 Martini et al.
2018/0296663 A1 10/2018 Hipp et al.
2018/0303925 A1 10/2018 Weissman et al.
2018/0312545 A1 11/2018 Baumhof et al.
2019/0022247 A1 1/2019 Ansell et al.
2019/0024096 A1 1/2019 Schmid et al.
2019/0160164 A1 5/2019 Rauch et al.
2019/0249219 A1 8/2019 Reichert et al.
2019/0270697 A1 9/2019 Ansell et al.
2019/0274968 A1 9/2019 Weissman et al.

(56) References Cited

U.S. PATENT DOCUMENTS

| | | | |
|---|---|---|---|
| 2019/0314524 | A1 | 10/2019 | Ansell et al. |
| 2019/0359556 | A1 | 11/2019 | Du et al. |
| 2020/0046838 | A1 | 2/2020 | Ansell et al. |
| 2020/0093936 | A1 | 3/2020 | Muzykantov et al. |
| 2020/0121809 | A1 | 4/2020 | Hope et al. |
| 2020/0163878 | A1 | 5/2020 | Baumhof et al. |
| 2020/0172472 | A1 | 6/2020 | Du |
| 2020/0283372 | A1 | 9/2020 | Du |
| 2020/0368254 | A1 | 11/2020 | Xu et al. |
| 2021/0008552 | A1 | 1/2021 | Regan et al. |
| 2021/0069336 | A1 | 3/2021 | Dong et al. |
| 2021/0107861 | A1 | 4/2021 | Ansell et al. |
| 2021/0122702 | A1 | 4/2021 | Du |
| 2021/0122703 | A1 | 4/2021 | Du |
| 2021/0128488 | A1 | 5/2021 | Du |
| 2021/0251898 | A1 | 8/2021 | Baumhof et al. |
| 2021/0395188 | A1 | 12/2021 | Ansell |
| 2022/0040285 | A1 | 2/2022 | Weissman et al. |
| 2022/0072155 | A1 | 3/2022 | Ansell et al. |
| 2022/0106257 | A1 | 4/2022 | Gatenyo et al. |
| 2022/0204439 | A1 | 6/2022 | Du et al. |
| 2022/0226461 | A1 | 7/2022 | Weissman et al. |
| 2022/0273567 | A1 | 9/2022 | Barbosa et al. |
| 2022/0378938 | A1 | 12/2022 | Huang et al. |
| 2023/0093138 | A1 | 3/2023 | Huang et al. |
| 2023/0097090 | A1 | 3/2023 | Tam et al. |
| 2023/0123534 | A1 | 4/2023 | Du |
| 2023/0295075 | A1 | 9/2023 | Du et al. |
| 2023/0372537 | A1 | 11/2023 | Hope et al. |
| 2024/0075163 | A1 | 3/2024 | Ansell et al. |
| 2024/0122854 | A1 | 4/2024 | Du et al. |
| 2024/0270679 | A1 | 8/2024 | Du et al. |
| 2024/0308952 | A1 | 9/2024 | Du |
| 2024/0417370 | A1 | 12/2024 | Tan et al. |
| 2024/0423914 | A1 | 12/2024 | Tan |
| 2024/0423915 | A1 | 12/2024 | Tan et al. |
| 2024/0424133 | A1 | 12/2024 | Chu et al. |
| 2025/0025427 | A1 | 1/2025 | Du et al. |
| 2025/0034081 | A1 | 1/2025 | Ansell et al. |
| 2025/0059131 | A1 | 2/2025 | Gatenyo et al. |
| 2025/0084029 | A1 | 3/2025 | Du |
| 2025/0084030 | A1 | 3/2025 | Du |
| 2025/0092002 | A1 | 3/2025 | Tan et al. |
| 2025/0161227 | A1 | 5/2025 | Ansell et al. |
| 2025/0188016 | A1 | 6/2025 | Ansell |
| 2025/0188020 | A1 | 6/2025 | Du et al. |
| 2025/0236586 | A1 | 7/2025 | Du |
| 2025/0288522 | A1 | 9/2025 | Baumhof et al. |
| 2025/0375464 | A1 | 12/2025 | Witt et al. |

FOREIGN PATENT DOCUMENTS

| | | | |
|---|---|---|---|
| CN | 104876831 | A | 9/2015 |
| CN | 105343891 | A | 2/2016 |
| CN | 105555757 | A | 5/2016 |
| CN | 107530436 | A | 1/2018 |
| CN | 113387825 | A | 9/2021 |
| DE | 707 279 | C | 6/1941 |
| DE | 25 15 146 | A1 | 10/1976 |
| EP | 0784056 | A1 | 7/1997 |
| EP | 1083232 | A1 | 3/2001 |
| EP | 2157982 | B1 | 12/2014 |
| EP | 2871178 | A1 | 5/2015 |
| EP | 3628335 | A1 | 4/2020 |
| EP | 2852381 | B1 | 10/2020 |
| FR | 1 386 626 | A | 1/1965 |
| FR | 2407258 | A1 | 5/1979 |
| GB | 1 277 947 | A | 6/1972 |
| GB | 1545899 | A | 5/1979 |
| JP | H05331118 | A | 12/1993 |
| JP | H09255638 | | 9/1997 |
| JP | H09315006 | A | 12/1997 |
| JP | H103643 | A | 1/1998 |
| JP | H10152461 | A | 6/1998 |
| JP | H11510489 | A | 9/1999 |
| JP | 2001325715 | A | 11/2001 |
| JP | 2001338416 | A | 12/2001 |
| JP | 2003081776 | A | 3/2003 |
| JP | 4538429 | B2 | 9/2010 |
| JP | 4681425 | B2 | 5/2011 |
| JP | 2015214560 | A | 12/2015 |
| JP | 2015231981 | A | 12/2015 |
| JP | 2016023149 | A | 2/2016 |
| JP | 2018524330 | A | 8/2018 |
| JP | 2021110236 | A | 8/2021 |
| PL | 210 199 | B1 | 12/2011 |
| WO | 8505047 | A1 | 11/1985 |
| WO | 8707183 | A1 | 12/1987 |
| WO | 9116024 | A1 | 10/1991 |
| WO | 9117424 | A1 | 11/1991 |
| WO | 9703939 | A1 | 2/1997 |
| WO | 9816599 | A1 | 4/1998 |
| WO | 9905094 | A1 | 2/1999 |
| WO | 9933493 | A1 | 7/1999 |
| WO | 0030444 | A1 | 6/2000 |
| WO | 0030688 | A2 | 6/2000 |
| WO | 0107548 | A1 | 2/2001 |
| WO | 0148233 | A1 | 7/2001 |
| WO | 02090988 | A1 | 11/2002 |
| WO | 03053409 | A1 | 7/2003 |
| WO | 2005060934 | A1 | 7/2005 |
| WO | 2006009011 | A1 | 1/2006 |
| WO | 2006138380 | A2 | 12/2006 |
| WO | 2007024708 | A2 | 3/2007 |
| WO | 2009107902 | A1 | 9/2009 |
| WO | 2009132131 | A1 | 10/2009 |
| WO | 2010033043 | A1 | 3/2010 |
| WO | 2010042877 | A1 | 4/2010 |
| WO | 2010048536 | A2 | 4/2010 |
| WO | 2010054405 | A1 | 5/2010 |
| WO | 2010054406 | A1 | 5/2010 |
| WO | 2010057150 | A1 | 5/2010 |
| WO | 2010062322 | A2 | 6/2010 |
| WO | 2010088537 | A2 | 8/2010 |
| WO | 2011075656 | A1 | 6/2011 |
| WO | 2011106688 | A1 | 9/2011 |
| WO | 2011140627 | A1 | 11/2011 |
| WO | 2011141703 | A1 | 11/2011 |
| WO | 2011141705 | A1 | 11/2011 |
| WO | 2011143230 | A1 | 11/2011 |
| WO | 2011153493 | A2 | 12/2011 |
| WO | 2012000104 | A1 | 1/2012 |
| WO | 2012016184 | A2 | 2/2012 |
| WO | 2012019630 | A1 | 2/2012 |
| WO | 2012044638 | A1 | 4/2012 |
| WO | 2012054365 | A2 | 4/2012 |
| WO | 2012054923 | A2 | 4/2012 |
| WO | 2012061259 | A2 | 5/2012 |
| WO | 2012068176 | A1 | 5/2012 |
| WO | 2013014073 | A1 | 1/2013 |
| WO | 2013016058 | A1 | 1/2013 |
| WO | 2013044008 | A2 | 3/2013 |
| WO | 2013059496 | A1 | 4/2013 |
| WO | 2013086322 | A1 | 6/2013 |
| WO | 2013086354 | A1 | 6/2013 |
| WO | 2013086373 | A1 | 6/2013 |
| WO | 2013143555 | A1 | 10/2013 |
| WO | 2014008334 | A1 | 1/2014 |
| WO | 2014028487 | A1 | 2/2014 |
| WO | 2014089239 | A1 | 6/2014 |
| WO | 2014136086 | | 9/2014 |
| WO | 2014153163 | A1 | 9/2014 |
| WO | 2014160243 | A1 | 10/2014 |
| WO | 2014160284 | A1 | 10/2014 |
| WO | 2014191467 | A1 | 12/2014 |
| WO | 2015074085 | A1 | 5/2015 |
| WO | 2015123576 | A2 | 8/2015 |
| WO | 2015130584 | A2 | 9/2015 |
| WO | 2015164674 | A1 | 10/2015 |
| WO | 2015177752 | A1 | 11/2015 |
| WO | 2015199952 | A1 | 12/2015 |
| WO | 2016010840 | A1 | 1/2016 |
| WO | 2016014463 | A1 | 1/2016 |
| WO | 2016014794 | A1 | 1/2016 |

(56) References Cited

FOREIGN PATENT DOCUMENTS

| | | | | |
|---|---|---|---|---|
| WO | 2016071857 | | 5/2016 | |
| WO | 2016168469 | A1 | 10/2016 | |
| WO | 2016176330 | A1 | 11/2016 | |
| WO | 2016210190 | A1 | 12/2016 | |
| WO | 2017004143 | A1 | 1/2017 | |
| WO | 2017021546 | A1 | 2/2017 | |
| WO | 2017048770 | A1 | 3/2017 | |
| WO | WO-2017049245 | A2 * | 3/2017 | A61P 37/04 |
| WO | 2017070616 | A2 | 4/2017 | |
| WO | 2017070626 | A2 | 4/2017 | |
| WO | 2017075531 | A1 | 5/2017 | |
| WO | 2017112865 | A1 | 6/2017 | |
| WO | 2017117528 | A1 | 7/2017 | |
| WO | 2017137095 | A1 | 8/2017 | |
| WO | 2017140905 | A1 | 8/2017 | |
| WO | 2017173054 | A1 | 10/2017 | |
| WO | 2017182634 | A1 | 10/2017 | |
| WO | 2017194454 | A1 | 11/2017 | |
| WO | 2017201332 | A1 | 11/2017 | |
| WO | 2018078053 | A1 | 5/2018 | |
| WO | 2018081638 | A1 | 5/2018 | |
| WO | 2018087753 | A1 | 5/2018 | |
| WO | 2018191657 | A1 | 10/2018 | |
| WO | 2018200943 | A1 | 11/2018 | |
| WO | 2019036030 | A1 | 2/2019 | |
| WO | 2019067872 | A1 | 4/2019 | |
| WO | 2019067992 | A1 | 4/2019 | |
| WO | 2019089828 | A1 | 5/2019 | |
| WO | 2019152848 | A1 | 8/2019 | |
| WO | 2020198697 | A1 | 10/2020 | |
| WO | 2022016070 | A1 | 1/2022 | |
| WO | 2022214025 | A1 | 10/2022 | |
| WO | 2023078950 | A1 | 5/2023 | |
| WO | 2023091490 | A1 | 5/2023 | |
| WO | 2024233387 | A1 | 11/2024 | |

OTHER PUBLICATIONS

Alexidis et al., "Novel 1,4 Substituted Piperidine Derivatives. Synthesis and Correlation of Antioxidant Activity with Structure and Lipophilicity," J. Pharm. Pharmacol. 47:131-137, 1995.

American Cancer Society, "Can Cancer Be Prevented?," Cancer Facts & Figures 2009, retrieved from www.cancer.org, Feb. 2009.

Anderson et al., "Incorporation of pseudouridine into mRNA enhances translation by diminishing PKR activation," Nucleic Acids Res. 38(17):5884-5892, 2010.

Anderson et al., "Nucleoside modifications in RNA limit activation of 2'-5'-oligoadenylate synthetase and increase resistance to cleavage by RNase L.," Nucleic Acids Research 39(21):9329-9338, 2011.

Ansell et al., "Application of Oligo-(14-amino-3,6,9,12-tetraoxatetradecanoic acid) Lipid Conjugates as Steric Barrier Molecules in Liposomal Formulations," Bioconjugate Chem. 10:653-666, 1999.

Aroua et al., "C60 Pyrrolidine Bis-carboxylic Acid Derivative as a Versatile Precursor for Biocompatible Fullerenes," Org. Lett. 16:1688-1691, 2014.

Aroua et al., "Essential Factors for Control of the Equilibrium in the Reversible Rearrangement of M3N@Ih-C80 Fulleropyrrolidines: Exohedral Functional Groups versus Endohedral Metal Clusters," Chem. Eur. J. 20:14032-14039, 2014. (with Supporting Information).

Aroua et al., "Essential Factors for Control of the Equilibrium in the Reversible Rearrangement of M3N@Ih-C80 Fulleropyrrolidines: Exohedral Functional Groups versus Endohedral Metal Clusters," Chemistry A European Journal 20(43):14032-14039, Oct. 2014. (146 pages).

Avanti Polar Lipids, "DMG-PEG 2000," Empirical Formula: C122H242O50, CAS No. 160743-62-4, 2024. (7 pages).

Basha et al., "Influence of cationic lipid composition on gene silencing properties of lipid nanoparticle formulations of siRNA in antigen-presenting cells," Mol. Ther. 19(12):2186-2200, 2011.

Belliveau et al., "Microfluidic Synthesis of Highly Potent Limit-size Lipid Nanoparticles for In Vivo Delivery of siRNA," Mol. Ther. Nucleic Acids 1:e37, 2012 (9 pages).

Bhattacharya et al., "Synthesis, Thermotropic Behavior, and Permeability Properties of Vesicular Membranes Composed of Cationic Mixed-Chain Surfactants," Langmuir 11:4748-4757, 1995.

Brito et al., "A Cationic Nanoemulsion for the Delivery of Next-generation RNA Vaccines," Molecular Therapy 22 (12):2118-2129, 2014.

Bruner et al., "3,5,5-Trimethylhexanol and Its Derivatives," Industrial & Engineering Chemistry 41(12):2860-2864, Dec. 1949. (5 pages).

CAS Registry No. 1027164-36-8, STN Entry Date: Jun. 11, 2008.

CAS Registry No. 1027557-08-9, STN Entry Date: Jun. 12, 2008.

CAS Registry No. 151271-61-3, STN Entry Date: Nov. 17, 1993.

CAS Registry No. 1851445-86-7, entered STN: Jan. 24, 2016, 1 page.

CAS Registry No. 1851849-79-0, Jan. 24, 2016, 1 page.

CAS Registry No. 1858471-71-2, entered STN: Feb. 3, 2016, 1 page.

CAS Registry No. 1861604-44-5, entered STN: Feb. 8, 2016, 1 page.

CAS Registry No. 1862119-13-8, entered STN: Feb. 8, 2016, 1 page.

CAS Registry No. 1866635-46-2, entered STN: Feb. 15, 2016, 1 page.

CAS Registry No. 1872489-33-2, Feb. 24, 2016, 1 page.

CAS Registry No. 2022900-51-0, entered STN: Nov. 1, 2016, 1 page.

CAS Registry No. 2106349-68-0, entered STN: Aug. 1, 2017, 1 page.

CAS Registry No. 719993-61-0, Jul. 30, 2004, 1 page.

CAS Registry No. 720660-49-1, Aug. 1, 2004, 1 page.

CAS Registry No. 745775-87-5, Sep. 16, 2004, 2 pages.

CAS Registry No. 749830-60-2, Sep. 23, 2004, 1 page.

CAS Registry No. 772323-67-8, STN Entry Date: Oct. 29, 2004.

CAS Registry No. 87973-08-8, Nov. 16, 1984, 1 page.

CAS Registry No. 92829-26-0, Dec. 17, 1984, 1 page.

Cattanach et al., "Studies in the Indole Series. Part IV. Tetrahydro-1H-pyrido[4,3-b]-indoles as Serotonin Antagonists," J. Chem Soc. (C):1235-1243, 1968.

Chang et al., U.S. Appl. No. 62/825,637, priority document of WO2020198697A1.

Chen et al., "Development of lipid nanoparticle formulations of siRNA for hepatocyte gene silencing following subcutaneous administration," Journal of Controlled Release 196:106-112, Oct. 5, 2014. (7 pages).

Chen et al., "Influence of particle size on the in vivo potency of lipid nanoparticle formulations of siRNA," Journal of Controlled Release 235:236-244, 2016.

Chen et al., "Lipopolyplex for Therapeutic Gene Delivery and Its Application for the Treatment of Parkinson's Disease," Frontiers in Aging Neuroscience 8:1-10, 2016.

Chen et al., "Rapid Discovery of Potent siRNA-Containing Lipid Nanoparticles Enabled by Controlled Microfluidic Formulation," J. Am. Chem. Soc. 134:6948-6951, 2012.

Chevalier et al., "Design, Activity, and Structure of a Highly Specific Artificial Endonuclease," Molecular Cell 10:895-905, 2002.

Choo et al., "Advances in Zinc Finger Engineering," Current Opinion in Structural Biology 10:411-416, 2000.

Conference call presentation entitled, "CureVac: Final Analysis of Pivotal Phase 2b/3 HERALD Study", Jul. 1, 2021. (14 pages).

Conference call transcript entitled, Final Analysis of Phase 2b/3 Clinical Trial of First-Generation COVID-19 Vaccine Candidate, CVnCoV, Jul. 1, 2021. (13 pages).

Cook et al., "Synthesis and Characterization of cis-Dioxomolybdenum(VI) Complexes with Sterically Bulky Tripodal Tetradentate Ligands," Inorganica Chimica Acta 144:81-87, 1988.

Durbin et al., "RNAs Containing Modified Nucleotides Fail to Trigger RIG-I Conformational Changes for Innate Immune Signaling," mBio 7(5):e00833-16, 2016 (11 pages).

(56) References Cited

OTHER PUBLICATIONS

Elbert et al., "Hydrophilic spacer groups in polymerizable lipids: formation of biomembrane models from bulk polymerized lipids," J. Am. Chem. Soc. 107:4134-4141, 1985. (8 pages).
Ernsting et al., "Factors controlling the pharmacokinetics, biodistribution and intratumoral penetration of nanoparticles," Journal of Controlled Release 172:782-794, 2013.
Evers et al., "State-of-the-Art Design and Rapid-Mixing Production Techniques of Lipid Nanoparticles for Nucleic Acid Delivery," Small Methods 2:1700375, Apr. 26, 2018. (20 pages).
Fagerlund et al., "The Cpf1 CRISPR-Cas Protein Expands Genome-Editing Tools," Genom Bio 16:251, 2015 (3 pages).
Falcone et al., "Both the 5' Untranslated Region and the Sequences Surrounding the Start Site Contribute to Efficient Initiation of Translation In Vitro," Molecular and Cellular Biology 11(5):2656-2664, 1991.
Frank-Kamenetsky et al., "Therapeutic RNAi targeting PCSK9 acutely lowers plasma cholesterol in rodents and LDL cholesterol in nonhuman primates," PNAS 105(33):11915-11920, Aug. 19, 2008 [with Supporting Information]. (13 pages).
Frisch et al. "A New Triantennary Galactose-Targeted PEGylated Gene Carrier, Characterization of Its Complex with DNA, and Transfection of Hepatoma Cells," Bioconjugate Chem. 15: 754-764, 2004.
Fumoto, "Organ-, Region-, and Cell-Selective Gene Transfer Using Non-Viral Vectors," Yakugaku Zasshi 129(9):1055-1061, 2009. (7 pages).
Hafez et al., "On the mechanism whereby cationic lipids promote intracellular delivery of polynucleic acids," Gene Therapy 8:1188-1196, 2001.
Haft et al., "A Guild of 45 CRISPR-Associated (Cas) Protein Families and Multiple CRISPR/Cas Subtypes Exist in Prokaryotic Genomes," PLoS Computational Biology 1(6):e60, 2005.
Han et al., "Synthesis and Properties of Di-Chain Esterquat Surfactants," J. Surfact Deterg. 18: 91-95, 2015.
Hassett et al., "Optimization of Lipid Nanoparticles for Intramuscular Administration of mRNA Vaccines," Molecular Therapy: Nucleic Acids 15:1-11, 2019.
Hekele et al., "Rapidly produced SAM® vaccine against H7N9 influenza is immunogenic in mice," Emerging Microbes and Infections 2:e52, 2013 (7 pages).
Heuer et al., "Repeat Domain Diversity of avrBs3-Like Genes in Ralstonia Solancearum Strains and Association with Host Preferences in the Field," Applied and Environmental Microbiology 73(13):4379-4384, 2007.
Higashi et al., "Novel lipidated sorbitol-based molecular transporters for non-viral gene delivery," Journal of Controlled Release 136:140-147, 2009.
Jasin, "Genetic Manipulation of Genomes with Rare-Cutting Endonucleases," Trends Genet 12:224-228, 1996.
Jayaraman et al., "Maximizing the Potency of siRNA Lipid Nanoparticles for Hepatic Gene Silencing In Vivo," Angew. Chem. Int. Ed. 51(34):8529-8533, XP055063645, 2012.
Jyotsana et al., "Lipid nanoparticle mediated siRNA delivery for safe targeting of human CML in vivo," Annals of Hematology 98(8):1905-1918, Aug. 1, 2019 (Europe PMC Funders Group Author Manuscript, available in PMC Feb. 1, 20211). (35 pages).
Kariko et al., "Incorporation of Pseudouridine into mRNA Yields Superior Nonimmunogenic Vector With Increased Translational Capacity and Biological Stability," Mol. Ther. 16(11):1833-1840, 2008.
Kariko et al., "Increased Erythropoiesis in Mice Injected with Submicrogram Quantities of Pseudouridine-containing mRNA Encoding Erythropoietin," Mol. Ther. 20(5):948-953, 2012.
Kariko et al., "Suppression of RNA Recognition by Toll-like Receptors: The Impact of Nucleoside Modification and the Evolutionary Origin of RNA," Immunity 23:165-175, 2005.
Kay et al., "A Bacterial Effector Acts as a Plant Transcription Factor and Induces a Cell Size Regulator," Science 318:648-651, 2007.
Kim et al., "Highly Efficient RNA-Guided Genome Editing in Human Cells via Delivery of Purified Cas9 Ribonucleoproteins," Genome Research 24(6):1012-1019, 2014.
Kim et al., "Hybrid restriction enzymes: zinc finger fusions to Fok I cleavage domain," PNAS USA 93(3):1156-1160, 1996.
Kim et al., "Synthesis of Novel Poly(amido ethylenimine) (PAMEIM) Dendrimer and Its Self-assembly with Plasmid DNA," Bull. Korean Chem. Soc. 27(11):1894-1896, 2006.
Kim et al., "Anti-EGFR immunonanoparticles containing IL 12 and salmosin genes for targeted cancer gene therapy," International Journal of Oncology 49:1130-1138, 2016.
Koh et al., "Delivery of antisense oligodeoxyribonucleotide lipopolyplex nanoparticles assembled by microfluidic hydrodynamic focusing," Journal of Controlled Release 141(1):62-69, 2010.
Kulkarni et al., "Lipid Nanoparticle Technology for Clinical Translation of siRNA Therapeutics," Accounts of Chemical Research 52:2435-2444, Aug. 9, 2019. (10 pages).
Kulkarni et al., "Lipid Nanoparticles Enabling Gene Therapies: From Concepts to Clinical Utility," Nucleic Acid Therapeutics 28(3):146-157, Jun. 2018 [Published online Apr. 23, 2018]. (12 pages).
Leblond et al., "Lipopolythioureas: A New Non-Cationic System for Gene Transfer," Bioconjugate Chemistry 18(2):484-493, 2007.
Lee et al., "Lipid nanoparticle siRNA systems for silencing the androgen receptor in human prostate cancer in vivo," Int. J. Cancer 131(5):E781-E790, 2012.
Leroueil et al., "Wide Varieties of Cationic Nanoparticles Induce Defects in Supported Lipid Bilayers," Nano Letters 8(2):420-424, 2008.
Leung et al., "Lipid Nanoparticles Containing siRNA Synthesized by Microfluidic Mixing Exhibit an Electron-Dense Nanostructured Core," J. Phys. Chem. C. Nanomater. Interfaces 116(34):18440-18450, 2012.
Leung et al., "Microfluidic Mixing: A General Method for Encapsulating Macromolecules in Lipid Nanoparticle Systems," J. Phys. Chem. B 119:8698-8706, 2015.
Lonez et al., "Cationic liposomal lipids: From gene carriers to cell signaling," Progress in Lipid Research 47(5):340-347, Sep. 2008.
MacLachlan, "Lipid Nanoparticle-Mediated Delivery of Messenger RNA," 1st International mRNA Health Conference, Oct. 24, 2013, Tübingen, Germany, 32 pages.
Maier et al., "Biodegradable lipids enabling rapidly eliminated lipid nanoparticles for systemic delivery of RNAi therapeutics," Mol. Ther. 21(8):1570-1578, 2013.
Makarova et al., "A Putative RNA-Interference-Based Immune System in Prokaryotes: Computational Analysis of the Predicted Enzymatic Machinery, Functional Analogies with Eukaryotic RNAi, and Hypothetical Mechanisms of Action," Biology Direct 1:7, 2006.
Marchi-Artzner et al., "Adhesion of Arg-Gly-Asp (RGD) Peptide Vesicles onto an Integrin Surface: Visualization of the Segregation of RGD Ligands into the Adhesion Plaques by Fluorescence," Langmuir 19:835-841, 2003.
Masuda et al., "Envelope-type lipid nanoparticles incorporating a short PEG-lipid conjugate for improved control of intracellular trafficking and transgene transcription," Biomaterials 30:4806-4814, 2009.
Mui et al., "Influence of Polyethylene Glycol Lipid Desorption Rates on Pharmacokinetics and Pharmacodynamics of siRNA Lipid Nanoparticles," Mol. Ther. Nucleic Acids 2:e139, 2013 (8 pages).
Nguyen et al, "Lipid-derived nanoparticles for immunostimulatory RNA adjuvant delivery", Proceedings of the National Academy of Sciences 109(14):E797-E803, 2012.
Nishida, "Disk-shaped magnetic recording medium," Caplus Database, Accession No. 2001:881906, 2001 (1 page).
Novobrantseva et al., "Systemic RNAi-mediated Gene Silencing in Nonhuman Primate and Rodent Myeloid Cells," Molecular Therapy—Nucleic Acids 1(e4), 2012, 13 pages.
Pabo et al., "Design and Selection of Novel Cys2His2 Zinc Finger Proteins," Ann. Rev. Biochem. 70:313-340, 2001.
Pajewski et al., "Pore formation in and enlargement of phospholipid liposomes by synthetic models of ceramides and sphingomyelin," Bioorganic & Medicinal Chemistry 13:29-37, 2005. (9 pages).

(56) References Cited

OTHER PUBLICATIONS

Pardi et al., "Expression kinetics of nucleoside-modified mRNA delivered in lipid nanoparticles to mice by various routes," Journal of Controlled Release 217:345-351, 2015.
Patani et al., "Bioisosterism: A Rational Approach in Drug Design," Chem. Rev. 96(8):3147-3176, Dec. 19, 1996.
Perler et al., "Protein splicing elements: inteins and exteins—a definition of terms and recommended nomenclature," Nucleic Acids Research 22(7):1125-1127, 1994.
Petsch et al., "Protective efficacy of in vitro synthesized, specific mRNA vaccines against influenza A virus infection," Nature Biotechnology 30(12):1210-1216, 2012 (9 pages).
Press release entitled, "CureVac Final Data from Phase 2b/3 Trial of First-Generation COVID-19 Vaccine Candidate, CVnCoV, Demonstrates Protection in Age Group of 18 to 60", Jun. 30, 2021.
Rajesh et al., "Dramatic Influence of the Orientation of Linker between Hydrophilic and Hydrophobic Lipid Moiety in Liposomal Gene Delivery," Journal of the American Chemical Society 129(37):11408-11420, 2007.
Reed et al., "Behavior of Plasticizers in Vinyl Chloride-Acetate Resins," Industrial & Engineering Chemistry 35(8):896-904, Aug. 1943. (9 pages).
Reichmuth et al., "mRNA vaccine delivery using lipid nanoparticles," Therapeutic Delivery 7(5):319-334, Apr. 14, 2016. (16 pages).
Rungta et al., "Lipid Nanoparticle Delivery of siRNA to Silence Neuronal Gene Expression in the Brain," Molecular Therapy 2:e136, Dec. 3, 2013. (17 pages).
Russell et al., "The Stability of Human β-Globin mRNA is Dependent on Structural Determinants Positioned Within Its 3' Untranslated Region," Blood 87:5314-5323, 1996.
Schar et al., "Long Chain Linear Fatty Alcohols from ZIEGLER-Synthesis, their Mixtures, Derivatives and Use," IP.com Prior Art Database Technical Disclosure, Jan. 17, 2011, 39 pages.
Scherphof et al., "Modulation of pharmacokinetic behavior of liposomes," Advanced Drug Delivery Reviews 24:179-191, Mar. 17, 1997. (13 pages).
Schnee et al., "An mRNA Vaccine Encoding Rabies Virus Glycoprotein Induces Protection against Lethal Infection in Mice and Correlates of Protection in Adult and Newborn Pigs," PLoS Negl. Trop. Dis. 10(6):e0004746, 2016 (20 pages).
Semple et al., "Interactions of liposomes and lipid-based carrier systems with blood proteins: Relation to clearance behaviour in vivo," Advanced Drug Delivery Reviews 32:3-17, 1998.
Semple et al., "Rational design of cationic lipids for siRNA delivery," Nature Biotechnology 28(2):172-176, 2010. (26 pages).
Szebeni et al., "Activation of complement by therapeutic liposomes and other lipid excipient-based therapeutic products: Prediction and prevention," Advanced Drug Delivery Reviews 63:1020-1030, 2011.
Szebeni et al., "Complement activation as a bioequivalence issue relevant to the development of generic liposomes and other nanoparticulate drugs," Biochemical and Biophysical Research Communications 468:490-497, 2015.
Szebeni, "Complement activation-related pseudoallergy: A stress reaction in blood triggered by nanomedicines and biologicals," Molecular Immunology 61:163-173, 2014.
Szolcsányi et al., "Short racemic syntheses of calvine and epicalvine," Tetrahedron Letters 49:1357-1360, 2008.
Tam et al., "Advances in Lipid Nanoparticles for siRNA Delivery," Pharmaceutics 5:498-507, 2013.
Tam et al., "Small molecule ligands for enhanced intracellular delivery of lipid nanoparticle formulations of siRNA," Nanomedicine 9(5):665-674, 2013.
Tas et al., "Poly(methyl methacrylate) Copolymers Containin Multiple, Pendent Plasticizing Groups," Journal of Polymer Science: Part A: Polymer Chemistry 48(11):2302-2310, Jun. 2010. (10 pages).
Tekmira Pharmaceuticals Corp, Form 20-F, EDGAR Online, filed Mar. 27, 2013, 298 pages.
Tekmira, "Tekmira and Alnylam Restructure Relationship and Settle All Litigation," Tekmira Pharmaceuticals Corporation, Nov. 12, 2012, 3 pages.
Thess et al., "Sequence-engineered mRNA Without Chemical Nucleoside Modifications Enables an Effective Protein Therapy in Large Animals," Molecular Therapy 23(9):1456-1464, Sep. 2015 [Published online Jun. 30, 2015]. (9 pages).
Torrecilla et al., "Lipid Nanoparticles as Carriers for RNAi against Viral Infections: Current Status and Future Perspectives," BioMed Research International 2014:Article ID 161794, 17 pages.
Van Doren et al., "Structure-Property Relationships in D-Glucitol Derivatives with Two Geminal Hydrocarbon Chains," J. Mater. Chem. 5(12):2153-2160, 1995.
Vanderah et al, "Oligo(ethylene oxide) Self-Assembled Monolayers with Self-Limiting Packing Densities for the Inhibition of Nonspecific Protein Adsorption," Langmuir 25(9):5026-5030, 2009.
Vogel et al., "A bacterial seek-and-destroy system for foreign DNA," Science 344(6187):972-973, 2014.
Wang et al., "Composite Nanoparticles for Gene Delivery," Adv. Genet. 88:111-137, 2014.
Wang et al., "Lipid Nanoparticles for Ocular Gene Delivery," J. Funct. Biomat 6(2):379-394, 2015.
Whitehead et al., "Synergistic Silencing: Combinations of Lipid-like Materials for Efficacious siRNA Delivery," Molecular Therapy 19(9):1688-1694, 2011.
Wilson et al., "The Combination of Stabilized Plasmid Lipid Particles and Lipid Nanoparticle Encapsulated CpG Containing Oligodeoxynucleotides as Systemic Genetic Vaccine," The Journal of Gene Medicine 11(1):14-25, 2009.
Witzigmann et al., "Lipid nanoparticle technology for therapeutic gene regulation in the liver," Advanced Drug Delivery Reviews 159:344-363, Jul. 2, 2020. (20 pages).
Xie et al., "Efficient sodium cation transport across liposome membranes using synthetic carriers," Journal of the American Chemical Society 116(2):690-696, 1994.
Xue et al., "Lipid-Based Nanocarriers for RNA Delivery," Current Pharmaceutical Design 21:3140-3147, 2015.
Yoshimura et al., "Solution Properties of Tadpole-type Cationic Amphiphilic Dendrimers Consisting of an Alkyl Chain, a Quaternary Ammonium, and a Poly(amidoamine) Dendron," Journal of Oleo Science 62(4):213-221, 2013.
Zhang et al., "Fighting against Skin Aging: The Way from Bench to Bedside," Cell Transplantation 27(5):729-738, 2018.
Zhang et al., "Biodegradable Amino-Ester Nanomaterials for Cas9 mRNA Delivery in Vitro and in Vivo," ACS Appl. Mater. Interfaces 9(30):25481-25487, 2017. (15 pages).
U.S. Appl. No. 19/212,290, filed May 19, 2025.
U.S. Appl. No. 19/296,652, filed Aug. 11, 2025.
U.S. Appl. No. 19/370,610, filed Oct. 27, 2025.
U.S. Appl. No. 19/389,853, filed Nov. 14, 2025.
U.S. Appl. No. 19/409,837, filed Dec. 5, 2025.
U.S. Appl. No. 19/530,016, filed Feb. 4, 2026.
U.S. Appl. No. 19/548,772, filed Feb. 24, 2026.

* cited by examiner

CARBONYL LIPIDS AND LIPID NANOPARTICLE FORMULATIONS FOR DELIVERY OF NUCLEIC ACIDS

BACKGROUND

Technical Field

Embodiments of the present invention generally relate to novel lipids that can be used in combination with other lipid components, such as neutral lipids, cholesterol and polymer conjugated lipids, to form lipid nanoparticles for delivery of therapeutic agents, such as nucleic acids (e.g., oligonucleotides, messenger RNA), both in vitro and in vivo.

Description of the Related Art

There are many challenges associated with the delivery of nucleic acids to affect a desired response in a biological system. Nucleic acid based therapeutics have enormous potential but there remains a need for more effective delivery of nucleic acids to appropriate sites within a cell or organism in order to realize this potential. Therapeutic nucleic acids include, e.g., messenger RNA (mRNA), antisense oligonucleotides, ribozymes, DNAzymes, plasmids, immune stimulating nucleic acids, antagomir, antimir, mimic, supermir, and aptamers. Some nucleic acids, such as mRNA or plasmids, can be used to effect expression of specific cellular products as would be useful in the treatment of, for example, diseases related to a deficiency of a protein or enzyme. The therapeutic applications of translatable nucleotide delivery are extremely broad as constructs can be synthesized to produce any chosen protein sequence, whether or not indigenous to the system. The expression products of the nucleic acid can augment existing levels of protein, replace missing or non-functional versions of a protein, or introduce new protein and associated functionality in a cell or organism.

Some nucleic acids, such as miRNA inhibitors, can be used to effect expression of specific cellular products that are regulated by miRNA as would be useful in the treatment of, for example, diseases related to deficiency of protein or enzyme. The therapeutic applications of miRNA inhibition are extremely broad as constructs can be synthesized to inhibit one or more miRNA that would in turn regulate the expression of mRNA products. The inhibition of endogenous miRNA can augment its downstream target endogenous protein expression and restore proper function in a cell or organism as a means to treat disease associated to a specific miRNA or a group of miRNA.

Other nucleic acids can down-regulate intracellular levels of specific mRNA and, as a result, down-regulate the synthesis of the corresponding proteins through processes such as RNA interference (RNAi) or complementary binding of antisense RNA. The therapeutic applications of antisense oligonucleotide and RNAi are also extremely broad, since oligonucleotide constructs can be synthesized with any nucleotide sequence directed against a target mRNA. Targets may include mRNAs from normal cells, mRNAs associated with disease-states, such as cancer, and mRNAs of infectious agents, such as viruses. To date, antisense oligonucleotide constructs have shown the ability to specifically down-regulate target proteins through degradation of the cognate mRNA in both in vitro and in vivo models. In addition, antisense oligonucleotide constructs are currently being evaluated in clinical studies.

However, two problems currently face the use of oligonucleotides in therapeutic contexts. First, free RNAs are susceptible to nuclease digestion in plasma. Second, free RNAs have limited ability to gain access to the intracellular compartment where the relevant translation machinery resides. Lipid nanoparticles formed from lipids formulated with other lipid components, such as neutral lipids, cholesterol, PEG, PEGylated lipids, and oligonucleotides have been used to block degradation of the RNAs in plasma and facilitate the cellular uptake of the oligonucleotides.

There remains a need for improved lipids and lipid nanoparticles for the delivery of oligonucleotides. Preferably, these lipid nanoparticles would provide optimal drug: lipid ratios, protect the nucleic acid from degradation and clearance in serum, be suitable for systemic or local delivery, and provide intracellular delivery of the nucleic acid. In addition, these lipid-nucleic acid particles should be well-tolerated and provide an adequate therapeutic index, such that patient treatment at an effective dose of the nucleic acid is not associated with unacceptable toxicity and/or risk to the patient. The present invention provides these and related advantages.

BRIEF SUMMARY

In brief, embodiments of the present invention provide lipid compounds, including stereoisomers, pharmaceutically acceptable salts, prodrugs or tautomers thereof, which can be used alone or in combination with other lipid components such as neutral lipids, charged lipids, steroids (including for example, all sterols) and/or their analogs, and/or polymer conjugated lipids to form lipid nanoparticles for the delivery of therapeutic agents. In some instances, the lipid nanoparticles are used to deliver nucleic acids such as antisense and/or messenger RNA. Methods for use of such lipid nanoparticles for treatment of various diseases or conditions, such as those caused by infectious entities and/or insufficiency of a protein, are also provided.

In one embodiment, compounds having the following structure (I) are provided:

(I)

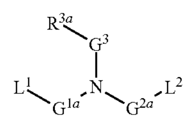

or a pharmaceutically acceptable salt, tautomer, prodrug or stereoisomer thereof, wherein $R^{3a}$, $L^1$, $L^2$, $G^{1a}$, $G^{2a}$, and $G^3$ are as defined herein.

In other embodiments, compounds having the following structure (II) are provided:

(II)

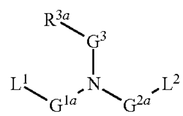

or a pharmaceutically acceptable salt, tautomer, prodrug or stereoisomer thereof, wherein $R^{3b}$, $L^1$, $L^2$, $G^{1b}$, $G^{2b}$, and $G^3$ are as defined herein.

Pharmaceutical compositions comprising one or more of the foregoing compounds of structure (I) or (II) and a therapeutic agent are also provided. Also provided are lipid nanoparticles (LNPs) comprising one or more compounds of structure (I) or (II). In some embodiments, the pharmaceutical compositions and/or LNPs further comprise one or more components selected from neutral lipids, charged lipids, steroids and polymer conjugated lipids. The disclosed compositions are useful for formation of lipid nanoparticles for the delivery of the therapeutic agent.

In other embodiments, the present invention provides a method for administering a therapeutic agent to a patient in need thereof, the method comprising preparing a composition of lipid nanoparticles comprising the compound of structure (I) or (II) and a therapeutic agent and delivering the composition to the patient. For example, the composition may include LNPs comprising one or more compounds of structure (I) or (II).

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that the invention may be practiced without these details.

Embodiments of the present invention are based, in part, upon the discovery of novel lipids that provide advantages when used in lipid nanoparticles for the in vivo delivery of an active or therapeutic agent such as a nucleic acid into a cell of a mammal. In particular, embodiments the present invention provides nucleic acid-lipid nanoparticle compositions comprising one or more of the novel lipids described herein that provide increased activity of the nucleic acid and improved tolerability of the compositions in vivo, resulting in a significant increase in the therapeutic index as compared to nucleic acid-lipid nanoparticle compositions previously described. For example, embodiments provide a lipid nanoparticle comprising one or more compounds of structure (I) or (II).

In particular embodiments, the present invention provides novel lipids that enable the formulation of improved compositions for the in vitro and in vivo delivery of mRNA and/or other oligonucleotides. In some embodiments, these improved lipid nanoparticle compositions are useful for expression of protein encoded by mRNA. In other embodiments, these improved lipid nanoparticles compositions are useful for upregulation of endogenous protein expression by delivering miRNA inhibitors targeting one specific miRNA or a group of miRNA regulating one target mRNA or several mRNA. In other embodiments, these improved lipid nanoparticle compositions are useful for down-regulating (e.g., silencing) the protein levels and/or mRNA levels of target genes. In some other embodiments, the lipid nanoparticles are also useful for delivery of mRNA and plasmids for expression of transgenes. In yet other embodiments, the lipid nanoparticle compositions are useful for inducing a pharmacological effect resulting from expression of a protein, e.g., increased production of red blood cells through the delivery of a suitable erythropoietin mRNA, or protection against infection through delivery of mRNA encoding for a suitable antigen or antibody.

The lipid nanoparticles and compositions of embodiments of the present invention may be used for a variety of purposes, including the delivery of encapsulated or associated (e.g., complexed) therapeutic agents such as nucleic acids to cells, both in vitro and in vivo. Accordingly, embodiments of the present invention provide methods of treating or preventing diseases or disorders in a subject in need thereof by contacting the subject with a lipid nanoparticle that encapsulates or is associated with a suitable therapeutic agent, wherein the lipid nanoparticle comprises one or more of the novel lipids described herein.

As described herein, embodiments of the lipid nanoparticles of the present invention are particularly useful for the delivery of nucleic acids, including, e.g., mRNA, antisense oligonucleotide, plasmid DNA, microRNA (miRNA), miRNA inhibitors (antagomirs/antimirs), messenger-RNA-interfering complementary RNA (micRNA), DNA, multivalent RNA, dicer substrate RNA, complementary DNA (cDNA), etc. Therefore, the lipid nanoparticles and compositions of embodiments of the present invention may be used to induce expression of a desired protein both in vitro and in vivo by contacting cells with a lipid nanoparticle comprising one or more novel lipids described herein, wherein the lipid nanoparticle encapsulates or is associated with a nucleic acid that is expressed to produce the desired protein (e.g., a messenger RNA or plasmid encoding the desired protein) or inhibit processes that terminate expression of mRNA (e.g., miRNA inhibitors). Alternatively, the lipid nanoparticles and compositions of embodiments of the present invention may be used to decrease the expression of target genes and proteins both in vitro and in vivo by contacting cells with a lipid nanoparticle comprising one or more novel lipids (e.g., a compound of structure (I) or (II)) described herein, wherein the lipid nanoparticle encapsulates or is associated with a nucleic acid that reduces target gene expression (e.g., an antisense oligonucleotide or small interfering RNA (siRNA)). The lipid nanoparticles and compositions of embodiments of the present invention may also be used for co-delivery of different nucleic acids (e.g., mRNA and plasmid DNA) separately or in combination, such as may be useful to provide an effect requiring colocalization of different nucleic acids (e.g., mRNA encoding for a suitable gene modifying enzyme and DNA segment(s) for incorporation into the host genome).

Nucleic acids for use with embodiments of this invention may be prepared according to any available technique. For mRNA, the primary methodology of preparation is, but not limited to, enzymatic synthesis (also termed in vitro transcription) which currently represents the most efficient method to produce long sequence-specific mRNA. In vitro transcription describes a process of template-directed synthesis of RNA molecules from an engineered DNA template comprised of an upstream bacteriophage promoter sequence (e.g., including but not limited to that from the T7, T3 and SP6 coliphage) linked to a downstream sequence encoding the gene of interest. Template DNA can be prepared for in vitro transcription from a number of sources with appropriate techniques which are well known in the art including, but not limited to, plasmid DNA and polymerase chain reaction amplification (see Linpinsel, J. L and Conn, G. L., General protocols for preparation of plasmid DNA template and Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012)

Transcription of the RNA occurs in vitro using the linearized DNA template in the presence of the corresponding RNA polymerase and adenosine, guanosine, uridine and cytidine ribonucleoside triphosphates (rNTPs) under conditions that support polymerase activity while minimizing potential degradation of the resultant mRNA transcripts. In vitro transcription can be performed using a variety of commercially available kits including, but not limited to RiboMax Large Scale RNA Production System (Promega), MegaScript Transcription kits (Life Technologies) as well as with commercially available reagents including RNA polymerases and rNTPs. The methodology for in vitro transcription of mRNA is well known in the art. (see, e.g., Losick, R., 1972, In vitro transcription, Ann Rev Biochem v. 41 409-46; Kamakaka, R. T. and Kraus, W. L. 2001. In Vitro Transcription. Current Protocols in Cell Biology. 2:11.6:11.6.1-11.6.17; Beckert, B. And Masquida, B., (2010) Synthesis of RNA by In Vitro Transcription in RNA in Methods in Molecular Biology v. 703 (Neilson, H. Ed), New York, N.Y. Humana Press, 2010; Brunelle, J. L. and Green, R., 2013, Chapter Five—In vitro transcription from plasmid or PCR-amplified DNA, Methods in Enzymology v. 530, 101-114; all of which are incorporated herein by reference).

The desired in vitro transcribed mRNA is then purified from the undesired components of the transcription or associated reactions (including unincorporated rNTPs, protein enzyme, salts, short RNA oligos, etc.). Techniques for the isolation of the mRNA transcripts are well known in the art. Well known procedures include phenol/chloroform extraction or precipitation with either alcohol (ethanol, isopropanol) in the presence of monovalent cations or lithium chloride. Additional, non-limiting examples of purification procedures which can be used include size exclusion chromatography (Lukaysky, P. J. and Puglisi, J. D., 2004, Large-scale preparation and purification of polyacrylamide-free RNA oligonucleotides, RNA v. 10, 889-893), silica-based affinity chromatography and polyacrylamide gel electrophoresis (Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012). Purification can be performed using a variety of commercially available kits including, but not limited to SV Total Isolation System (Promega) and In Vitro Transcription Cleanup and Concentration Kit (Norgen Biotek).

Furthermore, while reverse transcription can yield large quantities of mRNA, the products can contain a number of aberrant RNA impurities associated with undesired polymerase activity which may need to be removed from the full-length mRNA preparation. These include short RNAs that result from abortive transcription initiation as well as double-stranded RNA (dsRNA) generated by RNA-dependent RNA polymerase activity, RNA-primed transcription from RNA templates and self-complementary 3' extension. It has been demonstrated that these contaminants with dsRNA structures can lead to undesired immunostimulatory activity through interaction with various innate immune sensors in eukaryotic cells that function to recognize specific nucleic acid structures and induce potent immune responses. This in turn, can dramatically reduce mRNA translation since protein synthesis is reduced during the innate cellular immune response. Therefore, additional techniques to remove these dsRNA contaminants have been developed and are known in the art including but not limited to scaleable HPLC purification (see, e.g., Kariko, K., Muramatsu, H., Ludwig, J. And Weissman, D., 2011, Generating the optimal mRNA for therapy: HPLC purification eliminates immune activation and improves translation of nucleoside-modified, protein-encoding mRNA, Nucl Acid Res, v. 39 e142; Weissman, D., Pardi, N., Muramatsu, H., and Kariko, K., HPLC Purification of in vitro transcribed long RNA in Synthetic Messenger RNA and Cell Metabolism Modulation in Methods in Molecular Biology v. 969 (Rabinovich, P. H. Ed), 2013). HPLC purified mRNA has been reported to be translated at much greater levels, particularly in primary cells and in vivo.

A significant variety of modifications have been described in the art which are used to alter specific properties of in vitro transcribed mRNA, and improve its utility. These include, but are not limited to modifications to the 5' and 3' termini of the mRNA. Endogenous eukaryotic mRNA typically contain a cap structure on the 5'-end of a mature molecule which plays an important role in mediating binding of the mRNA Cap Binding Protein (CBP), which is in turn responsible for enhancing mRNA stability in the cell and efficiency of mRNA translation. Therefore, highest levels of protein expression are achieved with capped mRNA transcripts. The 5'-cap contains a 5'-5'-triphosphate linkage between the 5'-most nucleotide and guanine nucleotide. The conjugated guanine nucleotide is methylated at the N7 position. Additional modifications include methylation of the ultimate and penultimate most 5'-nucleotides on the 2'-hydroxyl group.

Multiple distinct cap structures can be used to generate the 5'-cap of in vitro transcribed synthetic mRNA. 5'-capping of synthetic mRNA can be performed co-transcriptionally with chemical cap analogs (i.e. capping during in vitro transcription). For example, the Anti-Reverse Cap Analog (ARCA) cap contains a 5'-5'-triphosphate guanine-guanine linkage where one guanine contains an N7 methyl group as well as a 3'-O-methyl group. However, up to 20% of transcripts remain uncapped during this co-transcriptional process and the synthetic cap analog is not identical to the 5'-cap structure of an authentic cellular mRNA, potentially reducing translatability and cellular stability. Alternatively, synthetic mRNA molecules may also be enzymatically capped post-transcriptionally. These may generate a more authentic 5'-cap structure that more closely mimics, either structurally or functionally, the endogenous 5'-cap which have enhanced binding of cap binding proteins, increased half-life, reduced susceptibility to 5' endonucleases, and/or reduced 5' decapping. Numerous synthetic 5'-cap analogs have been developed and are known in the art to enhance mRNA stability and translatability (see, e.g., .Grudzien-Nogalska, E., Kowalska, J., Su, W., Kuhn, A. N., Slepenkov, S. V., Darynkiewicz, E., Sahin, U., Jemielity, J., and Rhoads, R. E., Synthetic mRNAs with superior translation and stability properties in Synthetic Messenger RNA and Cell Metabolism Modulation in Methods in Molecular Biology v. 969 (Rabinovich, P. H. Ed), 2013).

On the 3'-terminus, a long chain of adenine nucleotides (poly-A tail) is normally added to mRNA molecules during RNA processing. Immediately after transcription, the 3' end of the transcript is cleaved to free a 3' hydroxyl to which poly-A polymerase adds a chain of adenine nucleotides to the RNA in a process called polyadenylation. The poly-A tail has been extensively shown to enhance both translational efficiency and stability of mRNA (see Bernstein, P. and Ross, J., 1989, Poly (A), poly (A) binding protein and the regulation of mRNA stability, Trends Bio Sci v. 14 373-377; Guhaniyogi, J. And Brewer, G., 2001, Regulation of mRNA stability in mammalian cells, Gene, v. 265, 11-23; Dreyfus, M. And Regnier, P., 2002, The poly (A) tail of mRNAs: Bodyguard in eukaryotes, scavenger in bacteria, Cell, v. 111, 611-613).

Poly (A) tailing of in vitro transcribed mRNA can be achieved using various approaches including, but not limited to, cloning of a poly (T) tract into the DNA template or by post-transcriptional addition using Poly (A) polymerase. The first case allows in vitro transcription of mRNA with poly (A) tails of defined length, depending on the size of the poly (T) tract, but requires additional manipulation of the template. The latter case involves the enzymatic addition of a poly (A) tail to in vitro transcribed mRNA using poly (A) polymerase which catalyzes the incorporation of adenine residues onto the 3' termini of RNA, requiring no additional manipulation of the DNA template, but results in mRNA with poly(A) tails of heterogeneous length. 5'-capping and 3'-poly (A) tailing can be performed using a variety of commercially available kits including, but not limited to Poly (A) Polymerase Tailing kit (EpiCenter), mMESSAGE mMACHINE T7 Ultra kit and Poly (A) Tailing kit (Life Technologies) as well as with commercially available reagents, various ARCA caps, Poly (A) polymerase, etc.

In addition to 5' cap and 3' poly adenylation, other modifications of the in vitro transcripts have been reported to provide benefits as related to efficiency of translation and stability. It is well known in the art that pathogenic DNA and RNA can be recognized by a variety of sensors within eukaryotes and trigger potent innate immune responses. The ability to discriminate between pathogenic and self DNA and RNA has been shown to be based, at least in part, on structure and nucleoside modifications since most nucleic acids from natural sources contain modified nucleosides In contrast, in vitro synthesized RNA lacks these modifications, thus rendering it immunostimulatory which in turn can inhibit effective mRNA translation as outlined above. The introduction of modified nucleosides into in vitro transcribed mRNA can be used to prevent recognition and activation of RNA sensors, thus mitigating this undesired immunostimulatory activity and enhancing translation capacity (see e.g. Kariko, K. And Weissman, D. 2007, Naturally occurring nucleoside modifications suppress the immunostimulatory activity of RNA: implication for therapeutic RNA development, Curr Opin Drug Discov Devel, v. 10 523-532; Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v. 969 (Rabinovich, P. H. Ed), 2013); Kariko, K., Muramatsu, H., Welsh, F. A., Ludwig, J., Kato, H., Akira, S., Weissman, D., 2008, Incorporation of Pseudouridine Into mRNA Yields Superior Nonimmunogenic Vector With Increased Translational Capacity and Biological Stability, Mol Ther v. 16, 1833-1840. The modified nucleosides and nucleotides used in the synthesis of modified RNAs can be prepared monitored and utilized using general methods and procedures known in the art. A large variety of nucleoside modifications are available that may be incorporated alone or in combination with other modified nucleosides to some extent into the in vitro transcribed mRNA (see e.g. US2012/0251618). In vitro synthesis of nucleoside-modified mRNA have been reported to have reduced ability to activate immune sensors with a concomitant enhanced translational capacity.

Other components of mRNA which can be modified to provide benefit in terms of translatability and stability include the 5' and 3' untranslated regions (UTR). Optimization of the UTRs (favorable 5' and 3' UTRs can be obtained from cellular or viral RNAs), either both or independently, have been shown to increase mRNA stability and translational efficiency of in vitro transcribed mRNA (see e.g. Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v. 969 (Rabinovich, P. H. Ed), 2013).

In addition to mRNA, other nucleic acid payloads may be used for embodiments of this invention. For oligonucleotides, methods of preparation include but are not limited to chemical synthesis and enzymatic, chemical cleavage of a longer precursor, in vitro transcription as described above, etc. Methods of synthesizing DNA and RNA nucleotides are widely used and well known in the art (see, e.g. Gait, M. J. (ed.) Oligonucleotide synthesis: a practical approach, Oxford [Oxfordshire], Washington, D.C.: IRL Press, 1984; and Herdewijn, P. (ed.) Oligonucleotide synthesis: methods and applications, Methods in Molecular Biology, v. 288 (Clifton, N.J.) Totowa, N.J.: Humana Press, 2005; both of which are incorporated herein by reference).

For plasmid DNA, preparation for use with embodiments of this invention commonly utilizes but is not limited to expansion and isolation of the plasmid DNA in vitro in a liquid culture of bacteria containing the plasmid of interest. The presence of a gene in the plasmid of interest that encodes resistance to a particular antibiotic (penicillin, kanamycin, etc.) allows those bacteria containing the plasmid of interest to selectively grow in antibiotic-containing cultures. Methods of isolating plasmid DNA are widely used and well known in the art (see, e.g. Heilig, J., Elbing, K. L. and Brent, R (2001) Large-Scale Preparation of Plasmid DNA. Current Protocols in Molecular Biology. 41:II:1.7: 1.7.1-1.7.16; Rozkov, A., Larsson, B., Gillström, S., Björnestedt, R. and Schmidt, S. R. (2008), Large-scale production of endotoxin-free plasmids for transient expression in mammalian cell culture. Biotechnol. Bioeng., 99: 557-566; and U.S. Pat. No. 6,197,553B1). Plasmid isolation can be performed using a variety of commercially available kits including, but not limited to Plasmid Plus (Qiagen), GenJET plasmid MaxiPrep (Thermo) and PureYield MaxiPrep (Promega) kits as well as with commercially available reagents.

Various exemplary embodiments of the lipids of the present invention, lipid nanoparticles and compositions comprising the same, and their use to deliver active (e.g. therapeutic agents), such as nucleic acids, to modulate gene and protein expression, are described in further detail below.

As used herein, the following terms have the meanings ascribed to them unless specified otherwise.

Unless the context requires otherwise, throughout the present specification and claims, the word "comprise" and variations thereof, such as, "comprises" and "comprising" are to be construed in an open and inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a", "an" and "the" include plural references unless the context clearly dictates otherwise.

The phrase "induce expression of a desired protein" refers to the ability of a nucleic acid to increase expression of the desired protein. To examine the extent of protein expression, a test sample (e.g. a sample of cells in culture expressing the desired protein) or a test mammal (e.g. a mammal such as a human or an animal model such as a rodent (e.g. mouse) or a non-human primate (e.g., monkey) model) is contacted with a nucleic acid (e.g. nucleic acid in combination with a lipid of the present invention). Expression of the desired protein in the test sample or test animal is compared to expression of the desired protein in a control sample (e.g. a sample of cells in culture expressing the desired protein) or a control mammal (e.g., a mammal such as a human or an animal model such as a rodent (e.g. mouse) or non-human primate (e.g. monkey) model) that is not contacted with or administered the nucleic acid. When the desired protein is present in a control sample or a control mammal, the expression of a desired protein in a control sample or a control mammal may be assigned a value of 1.0. In particular embodiments, inducing expression of a desired protein is achieved when the ratio of desired protein expression in the test sample or the test mammal to the level of desired protein expression in the control sample or the control mammal is greater than 1, for example, about 1.1, 1.5, 2.0. 5.0 or 10.0. When a desired protein is not present in a control sample or a control mammal, inducing expression of a desired protein is achieved when any measurable level of the desired protein in the test sample or the test mammal is detected. One of ordinary skill in the art will understand appropriate assays to determine the level of protein expression in a sample, for example dot blots, northern blots, in situ hybridization, ELISA, immunoprecipitation, enzyme function, and phenotypic assays, or assays based on reporter proteins that can produce fluorescence or luminescence under appropriate conditions.

The phrase "inhibiting expression of a target gene" refers to the ability of a nucleic acid to silence, reduce, or inhibit the expression of a target gene. To examine the extent of gene silencing, a test sample (e.g. a sample of cells in culture expressing the target gene) or a test mammal (e.g. a mammal such as a human or an animal model such as a rodent (e.g. mouse) or a non-human primate (e.g. monkey) model) is contacted with a nucleic acid that silences, reduces, or inhibits expression of the target gene. Expression of the target gene in the test sample or test animal is compared to expression of the target gene in a control sample (e.g. a sample of cells in culture expressing the target gene) or a control mammal (e.g. a mammal such as a human or an animal model such as a rodent (e.g. mouse) or non-human primate (e.g. monkey) model) that is not contacted with or administered the nucleic acid. The expression of the target gene in a control sample or a control mammal may be assigned a value of 100%. In particular embodiments, silencing, inhibition, or reduction of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%. In other words, the nucleic acids are capable of silencing, reducing, or inhibiting the expression of a target gene by at least about 5%, 10%, 15%, 20%, 25%, 30%, 35%, 40%, 45%, 50%, 55%, 60%, 65%, 70%, 75%, 80%, 85%, 90%, 95%, or 100% in a test sample or a test mammal relative to the level of target gene expression in a control sample or a control mammal not contacted with or administered the nucleic acid. Suitable assays for determining the level of target gene expression include, without limitation, examination of protein or mRNA levels using techniques known to those of skill in the art, such as, e.g., dot blots, northern blots, in situ hybridization, ELISA, immunoprecipitation, enzyme function, as well as phenotypic assays known to those of skill in the art.

An "effective amount" or "therapeutically effective amount" of an active agent or therapeutic agent such as a therapeutic nucleic acid is an amount sufficient to produce the desired effect, e.g. an increase or inhibition of expression of a target sequence in comparison to the normal expression level detected in the absence of the nucleic acid. An increase in expression of a target sequence is achieved when any measurable level is detected in the case of an expression product that is not present in the absence of the nucleic acid. In the case where the expression product is present at some level prior to contact with the nucleic acid, an in increase in expression is achieved when the fold increase in value obtained with a nucleic acid such as mRNA relative to control is about 1.05, 1.1, 1.2, 1.3, 1.4, 1.5, 1.75, 2, 2.5, 3, 4, 5, 6, 7, 8, 9, 10, 15, 20, 25, 30, 40, 50, 75, 100, 250, 500, 750, 1000, 5000, 10000 or greater. Inhibition of expression of a target gene or target sequence is achieved when the value obtained with a nucleic acid such as antisense oligonucleotide relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, fluorescence or luminescence of suitable reporter proteins, as well as phenotypic assays known to those of skill in the art.

The term "nucleic acid" as used herein refers to a polymer containing at least two deoxyribonucleotides or ribonucleotides in either single- or double-stranded form and includes DNA, RNA, and hybrids thereof. DNA may be in the form of antisense molecules, plasmid DNA, cDNA, PCR products, or vectors. RNA may be in the form of small hairpin RNA (shRNA), messenger RNA (mRNA), antisense RNA, miRNA, micRNA, multivalent RNA, dicer substrate RNA or viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, single nucleotide polymorphisms, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res., 19:5081 (1991); Ohtsuka et al., J. Biol. Chem., 260:2605-2608 (1985); Rossolini et al., Mol. Cell. Probes, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are generally characterized by being poorly soluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

A "steroid" is a compound comprising the following carbon skeleton:

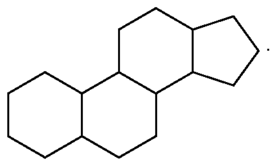 [SMILES: C1CCC2C(C1)CCC1C3CCCC3CCC21]

Non-limiting examples of steroids include cholesterol, and the like.

A "cationic lipid" refers to a lipid capable of being positively charged. Exemplary cationic lipids include one or more amine group(s) which bear the positive charge. Preferred cationic lipids are ionizable such that they can exist in a positively charged or neutral form depending on pH. The ionization of the cationic lipid affects the surface charge of the lipid nanoparticle under different pH conditions. This charge state can influence plasma protein absorption, blood clearance and tissue distribution (Semple, S. C., et al., Adv. Drug Deliv Rev 32:3-17 (1998)) as well as the ability to form endosomolytic non-bilayer structures (Hafez, I. M., et al., Gene Ther 8:1188-1196 (2001)) critical to the intracellular delivery of nucleic acids.

The term "polymer conjugated lipid" refers to a molecule comprising both a lipid portion and a polymer portion. An example of a polymer conjugated lipid is a pegylated lipid. The term "pegylated lipid" refers to a molecule comprising both a lipid portion and a polyethylene glycol portion. Pegylated lipids are known in the art and include 1-(monomethoxy-polyethyleneglycol)-2,3-dimyristoylglycerol (PEG-DMG) and the like.

The term "neutral lipid" refers to any of a number of lipid species that exist either in an uncharged or neutral zwitterionic form at a selected pH. At physiological pH, such lipids include, but are not limited to, phosphotidylcholines such as 1,2-Distearoyl-sn-glycero-3-phosphocholine (DSPC), 1,2-Dipalmitoyl-sn-glycero-3-phosphocholine (DPPC), 1,2-Dimyristoyl-sn-glycero-3-phosphocholine (DMPC), 1-Palmitoyl-2-oleoyl-sn-glycero-3-phosphocholine (POPC), 1,2-dioleoyl-sn-glycero-3-phosphocholine (DOPC), phophatidylethanolamines such as 1,2-Dioleoyl-sn-glycero-3-phosphoethanolamine (DOPE), sphingomyelins (SM), ceramides, steroids such as sterols and their derivatives. Neutral lipids may be synthetic or naturally derived.

The term "charged lipid" refers to any of a number of lipid species that exist in either a positively charged or negatively charged form independent of the pH within a useful physiological range e.g. pH~3 to pH~9. Charged lipids may be synthetic or naturally derived. Examples of charged lipids include phosphatidylserines, phosphatidic acids, phosphatidylglycerols, phosphatidylinositols, sterol hemi succinates, dialkyl trimethylammonium-propanes, (e.g. DOTAP, DOTMA), dialkyl dimethylaminopropanes, ethyl phosphocholines, dimethylaminoethane carbamoyl sterols (e.g. DC-Chol).

The term "lipid nanoparticle" refers to particles having at least one dimension on the order of nanometers (e.g., 1-1,000 nm) which include one or more of the compounds of structure (I) or (II) or other specified cationic lipids. In some embodiments, lipid nanoparticles are included in a formulation that can be used to deliver an active agent or therapeutic agent, such as a nucleic acid (e.g., mRNA) to a target site of interest (e.g., cell, tissue, organ, tumor, and the like). In some embodiments, the lipid nanoparticles of the invention comprise a nucleic acid. Such lipid nanoparticles typically comprise a compound of structure (I) or (II) and one or more excipient selected from neutral lipids, charged lipids, steroids and polymer conjugated lipids. In some embodiments, the active agent or therapeutic agent, such as a nucleic acid, may be encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells e.g. an adverse immune response.

In various embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In certain embodiments, nucleic acids, when present in the lipid nanoparticles, are resistant in aqueous solution to degradation with a nuclease. Lipid nanoparticles comprising nucleic acids and their method of preparation are disclosed in, e.g., U.S. Patent Publication Nos. 2004/0142025, 2007/0042031 and PCT Pub. Nos. WO 2017/004143, WO 2015/199952, WO 2013/016058 and WO 2013/086373, the full disclosures of which are herein incorporated by reference in their entirety for all purposes.

As used herein, "lipid encapsulated" refers to a lipid nanoparticle that provides an active agent or therapeutic agent, such as a nucleic acid (e.g., mRNA), with full encapsulation, partial encapsulation, or both. In an embodiment, the nucleic acid (e.g., mRNA) is fully encapsulated in the lipid nanoparticle.

As used herein, the term "aqueous solution" refers to a composition comprising water.

"Serum-stable" in relation to nucleic acid-lipid nanoparticles means that the nucleotide is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of a therapeutic product that can result in a broad exposure of an active agent within an organism. Some techniques of administration can lead to the systemic delivery of certain agents, but not others. Systemic delivery means that a useful, preferably therapeutic, amount of an agent is exposed to most parts of the body. Systemic delivery of lipid nanoparticles can be by any means known in the art including, for example, intravenous, intraarterial, subcutaneous, and intraperitoneal delivery. In some embodiments, systemic delivery of lipid nanoparticles is by intravenous delivery.

"Local delivery," as used herein, refers to delivery of an active agent directly to a target site within an organism. For example, an agent can be locally delivered by direct injection into a disease site such as a tumor, other target site such as a site of inflammation, or a target organ such as the liver, heart, pancreas, kidney, and the like. Local delivery can also include topical applications or localized injection techniques such as intramuscular, subcutaneous or intradermal injection. Local delivery does not preclude a systemic pharmacological effect.

"Alkyl" refers to a straight or branched hydrocarbon chain radical consisting solely of carbon and hydrogen atoms, which is saturated, having, for example, from one to twenty-four carbon atoms ($C_1$-$C_{24}$ alkyl), four to twenty carbon atoms ($C_4$-$C_{20}$ alkyl), six to sixteen carbon atoms ($C_6$-$C_{16}$ alkyl), six to nine carbon atoms ($C_6$-$C_9$ alkyl), one to fifteen carbon atoms ($C_1$-$C_{15}$ alkyl), one to twelve carbon atoms ($C_1$-$C_{12}$ alkyl), one to eight carbon atoms ($C_1$-$C_8$ alkyl) or one to six carbon atoms ($C_1$-$C_6$ alkyl) and which is attached to the rest of the molecule by a single bond, e.g., methyl, ethyl, n-propyl, 1 methylethyl (iso propyl), n-butyl, n-pentyl, 1,1-dimethylethyl (t butyl), 3-methylhexyl, 2-methylhexyl, and the like. Unless stated otherwise specifically in the specification, an alkyl group is optionally substituted.

"Alkenyl" refers to a straight or branched hydrocarbon chain radical consisting solely of carbon and hydrogen atoms, which contains one or more carbon-carbon double bonds, and having, for example, from two to twenty-four carbon atoms ($C_2$-$C_{24}$ alkenyl), four to twenty carbon atoms ($C_4$-$C_{20}$ alkenyl), six to sixteen carbon atoms ($C_6$-$C_{16}$ alkenyl), six to nine carbon atoms ($C_6$-$C_9$ alkenyl), two to fifteen carbon atoms ($C_2$-$C_{15}$ alkenyl), two to twelve carbon atoms ($C_2$-$C_{12}$ alkenyl), two to eight carbon atoms ($C_2$-$C_8$ alkenyl) or two to six carbon atoms ($C_2$-$C_6$ alkenyl) and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group is optionally substituted.

"Alkynyl" refers to a straight or branched hydrocarbon chain radical consisting solely of carbon and hydrogen atoms, which contains one or more carbon-carbon triple bonds, and having, for example, from two to twenty-four carbon atoms ($C_2$-$C_{24}$ alkynyl), four to twenty carbon atoms ($C_4$-Cao alkynyl), six to sixteen carbon atoms ($C_6$-$C_{16}$ alkynyl), six to nine carbon atoms ($C_6$-$C_9$ alkynyl), two to fifteen carbon atoms ($C_2$-$C_{15}$ alkynyl), two to twelve carbon atoms ($C_2$-$C_{12}$ alkynyl), two to eight carbon atoms ($C_2$-$C_8$ alkynyl) or two to six carbon atoms ($C_2$-$C_6$ alkynyl) and which is attached to the rest of the molecule by a single bond, e.g., ethynyl, propynyl, butynyl, pentynyl, and the like. Unless stated otherwise specifically in the specification, an alkynyl group is optionally substituted.

"Alkylene" or "alkylene chain" refers to a straight or branched divalent hydrocarbon chain linking the rest of the molecule to a radical group, consisting solely of carbon and hydrogen, which is saturated, and having, for example, from one to twenty-four carbon atoms ($C_1$-$C_{24}$ alkylene), one to fifteen carbon atoms ($C_1$-$C_{15}$ alkylene), one to twelve carbon atoms ($C_1$-$C_{12}$ alkylene), one to eight carbon atoms ($C_1$-$C_8$ alkylene), one to six carbon atoms ($C_1$-$C_6$ alkylene), two to four carbon atoms ($C_2$-$C_4$ alkylene), one to two carbon atoms ($C_1$-$C_2$ alkylene), e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain may be optionally substituted.

"Alkenylene" or "alkenylene chain" refers to a straight or branched divalent hydrocarbon chain linking the rest of the molecule to a radical group, consisting solely of carbon and hydrogen, which contains one or more carbon-carbon double bonds, and having, for example, from two to twenty-four carbon atoms ($C_2$-$C_{24}$ alkenylene), two to fifteen carbon atoms ($C_2$-$C_{15}$ alkenylene), two to twelve carbon atoms ($C_2$-$C_{12}$ alkenylene), two to eight carbon atoms ($C_2$-$C_8$ alkenylene), two to six carbon atoms ($C_2$-$C_6$ alkenylene) or two to four carbon atoms ($C_2$-$C_4$ alkenylene), e.g., ethenylene, propenylene, n-butenylene, and the like. The alkenylene chain is attached to the rest of the molecule through a single or double bond and to the radical group through a single or double bond. The points of attachment of the alkenylene chain to the rest of the molecule and to the radical group can be through one carbon or any two carbons within the chain. Unless stated otherwise specifically in the specification, an alkenylene chain may be optionally substituted.

"Aryl" refers to a carbocyclic ring system radical comprising hydrogen, 6 to 18 carbon atoms and at least one aromatic ring. For purposes of this invention, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$-$R_c$ where $R_b$ is an alkylene or alkenylene as defined above and $R_c$ is one or more aryl radicals as defined above, for example, benzyl, diphenylmethyl and the like. Unless stated otherwise specifically in the specification, an aralkyl group is optionally substituted.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, from three to ten carbon atoms, or from three to eight carbon atoms, and which is saturated and attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylene" is a divalent cycloalkyl group. Unless otherwise stated specifically in the specification, a cycloalkylene group may be optionally substituted.

"Cycloalkenyl" refers to a stable non-aromatic monocyclic or polycyclic hydrocarbon radical consisting solely of carbon and hydrogen atoms, which may include fused or bridged ring systems, having from three to fifteen carbon atoms, from three to ten carbon atoms, or from three to eight carbon atoms, and which includes one or more carbon-carbon double bonds and is attached to the rest of the molecule by a single bond. Monocyclic cycloalkenyl radicals include, for example, cyclopropenyl, cyclobutenyl, cyclopentenyl, cyclohexenyl, cycloheptenyl, and cyclooctenyl. Unless otherwise stated specifically in the specification, a cycloalkenyl group may be optionally substituted.

"Cycloalkenylene" is a divalent cycloalkenyl group. Unless otherwise stated specifically in the specification, a cycloalkenylene group may be optionally substituted.

The term "substituted" used herein means any of the above groups (e.g. alkyl, alkenyl, alkynyl, alkylene, alkenylene, aryl, aralkyl, cycloalkyl, cycloalkyenyl, cycloalkylene or cycloalkenylene) wherein at least one hydrogen atom is replaced by a bond to a non-hydrogen atom such as, but not limited to: a halogen atom such as F, Cl, Br, or I; oxo groups (═O); hydroxyl groups (—OH); $C_1$-$C_{12}$ alkyl groups; cycloalkyl groups; —(C═O)OR'; —O(C═O)R'; —C(═O)R'; —OR'; —S(O)$_x$R'; —S—SR'; —C(═O)SR'; —SC(═O)R'; —NR'R'; —NR'C(═O)R'; —C(═O)NR'R'; —NR'C(═O)NR'R'; —OC(═O)NR'R'; —NR'C(═O)OR'; —NR'S(O)$_x$NR'R'; —NR'S(O)$_x$R'; and —S(O)$_x$NR'R', wherein: R' is, at each occurrence, independently H, $C_1$-$C_{15}$ alkyl or cycloalkyl, and x is 0, 1 or 2. In some embodiments the substituent is a $C_1$-$C_{12}$ alkyl group. In other embodiments, the substituent is a cycloalkyl group. In other embodiments, the substituent is a halo group, such as fluoro. In other embodiments, the substituent is an oxo group. In other embodiments, the substituent is a hydroxyl group. In other embodiments, the substituent is an alkoxy group (—OR'). In other embodiments, the substituent is a carboxyl group. In other embodiments, the substituent is an amine group (—NR'R').

"Optional" or "optionally" (e.g., optionally substituted) means that the subsequently described event of circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

"Prodrug" is meant to indicate a compound that may be converted under physiological conditions or by solvolysis to a biologically active compound of structure (I) or (II). Thus, the term "prodrug" refers to a metabolic precursor of a compound of structure (I) or (II) that is pharmaceutically acceptable. A prodrug may be inactive when administered to a subject in need thereof, but is converted in vivo to an active compound of structure (I) or (II). Prodrugs are typically rapidly transformed in vivo to yield the parent compound of structure (I) or (II), for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of structure (I) or (II) in vivo when such prodrug is administered to a mammalian subject. Prodrugs of a compound of structure (I) or (II) may be prepared by modifying functional groups present in the compound of structure (I) or (II) in such a way that the modifications are cleaved, either in routine manipulation or in vivo, to the parent compound of structure (I) or (II). Prodrugs include compounds of structure (I) or (II) wherein a hydroxy, amino or mercapto group is bonded to any group that, when the prodrug of the compound of structure (I) or (II) is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of structure (I) or (II) and the like.

Embodiments of the invention disclosed herein are also meant to encompass all pharmaceutically acceptable compounds of the compound of structure (I) or (II) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labelled compounds of structure (I) or (II), for example, those incorporating a radioactive isotope, are useful in drug and/or substrate tissue distribution studies. The radioactive isotopes tritium, i.e., $^{3}H$, and carbon-14, i.e., $^{14}C$, are particularly useful for this purpose in view of their ease of incorporation and ready means of detection.

Substitution with heavier isotopes such as deuterium, i.e., $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Embodiments of the invention disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, embodiments of the invention include compounds produced by a process comprising administering a compound of this invention to a mammal for a period of time sufficient to yield a metabolic product thereof. Such products are typically identified by administering a radiolabeled compound of structure (I) or (II) in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of structure (I) or (II). As used herein, the term "solvate" refers to an aggregate that comprises one or more molecules of a compound of structure (I) or (II) with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. In some embodiments, the compound of structure (I) or (II) may exist as a true solvate, while in other cases, the compound of structure (I) or (II) may merely retain adventitious water or be a mixture of water plus some adventitious solvent.

A "pharmaceutical composition" refers to a formulation of a compound of structure (I) and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of structure (I) or (II), or a lipid nanoparticle comprising the same, which, when administered to a mammal, preferably a human, is sufficient to effect treatment in the mammal, preferably a human. The amount of a lipid nanoparticle of embodiments the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of structure (I) or (II), or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Embodiments of the present invention are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Compounds

In an aspect, the invention provides novel lipid compounds which are capable of combining with other lipid components such as neutral lipids, charged lipids, steroids and/or polymer conjugated-lipids to form lipid nanoparticles with oligonucleotides. Without wishing to be bound by theory, it is thought that these lipid nanoparticles shield oligonucleotides from degradation in the serum and provide for effective delivery of oligonucleotides to cells in vitro and in vivo.

Compounds of Structure (I)

In one embodiment, the compounds have the following structure (I):

(I)

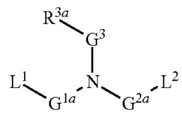

or a pharmaceutically acceptable salt, tautomer, prodrug or stereoisomer thereof, wherein:

$L^1$ is —O(C═O)$R^1$, —(C═O)O$R^1$, —C(═O)$R^1$, —O$R^1$, —S(O)$_x R^1$, —S—S$R^1$, —C(═O)S$R^1$, —SC(═O)$R^1$, —N$R^a$C(═O)$R^1$, —C(═O)N$R^b R^c$, —N$R^a$C(═O)N$R^b R^c$, —OC(═O)N$R^b R^c$ or —N$R^a$C(═O)O$R^1$;

$L^2$ is —O(C═O)$R^2$, —(C═O)O$R^2$, —C(═O)$R^2$, —O$R^2$, —S(O)$_x R^2$, —S—S$R^2$, —C(═O)S$R^2$, —SC(═O)$R^2$, —N$R^d$C(═O)$R^2$, —C(═O)N$R^e R^f$, —N$R^c$C(═O)N$R^e R^f$, —OC(═O)N$R^e R^f$; —N$R^d$C(═O)O$R^2$ or a direct bond to $R^2$;

$G^{1a}$ and $G^{2a}$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_3$-$C_8$ cycloalkylene or $C_3$-$C_8$ cycloalkenylene;

$R^a$, $R^b$, $R^d$ and $R^e$ are each independently H or $C_1$-$C_{12}$ alkyl or $C_2$-$C_{12}$ alkenyl;

$R^c$ and $R^f$ are each independently $C_1$-$C_{12}$ alkyl or $C_2$-$C_{12}$ alkenyl;

$R^1$ and $R^2$ are each independently branched $C_6$-$C_{24}$ alkyl or branched $C_6$-$C_{24}$ alkenyl;

$R^{3a}$ is —C(═O)N($R^{4a}$)$R^{5a}$ or —C(═O)O$R^6$;

$R^{4a}$ is $C_1$-$C_{12}$ alkyl;

$R^{5a}$ is H or $C_1$-$C_8$ alkyl or $C_2$-$C_8$ alkenyl;

$R^6$ is H, aryl or aralkyl; and x is 0, 1 or 2, and wherein each alkyl, alkenyl, alkylene, alkenylene, cycloalkylene, cycloalkenylene, aryl and aralkyl is independently substituted or unsubstituted.

In certain embodiments of structure (I), $G^3$ is unsubstituted. In more specific embodiments of structure (I), $G^3$ is $C_2$-$C_{12}$ alkylene, for example, in some embodiments of structure (I), $G^3$ is $C_3$-$C_7$ alkylene, or in other embodiments of structure (I), $G^3$ is $C_3$-$C_{12}$ alkylene. In some embodiments of structure (I), $G^3$ is $C_2$ or $C_3$ alkylene.

In some of the foregoing embodiments of structure (I), the compound has the following structure (IA):

(IA)

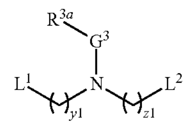

wherein y1 and z1 are each independently integers ranging from 2 to 12, for example an integer from 2 to 6, for example 4.

In some of the foregoing embodiments of structure (I), $L^1$ is —O(C═O)$R^1$, —(C═O)O$R^1$ or —C(═O)N$R^b R^c$, and $L^2$ is —O(C═O)$R^2$, —(C═O)O$R^2$ or —C(═O)N$R^e R^f$. For example, in some embodiments of structure (I) $L^1$ and $L^2$ are —(C═O)O$R^1$ and —(C═O)O$R^2$, respectively. In other embodiments of structure (I) $L^1$ is —(C═O)O$R^1$ and $L^2$ is —C(═O)N$R^e R^f$. In other embodiments of structure (I) $L^1$ is —C(═O)N$R^b R^c$ and $L^2$ is —C(═O)N$R^e R^f$.

In other embodiments of the foregoing, the compound has one of the following structures (IB), (IC), (ID) or (IE):

(IB)

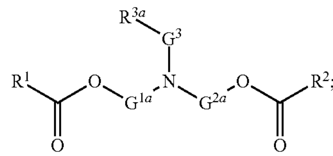

;

(IC)

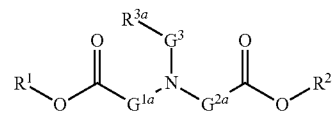

(ID)

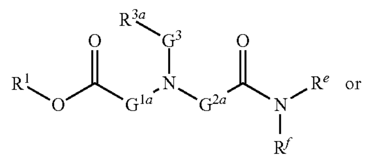

or

-continued (IE)

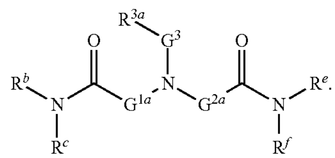

In some of the foregoing embodiments, the compound has structure (IB), in other embodiments, the compound has structure (IC) and in still other embodiments the compound has the structure (ID). In other embodiments, the compound has structure (IE).

In some different embodiments of the foregoing, the compound has one of the following structures (IF), (IG), (IH) or (IJ):

(IF)

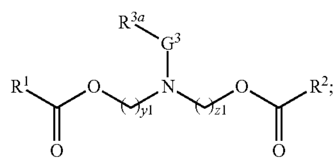

(IG)

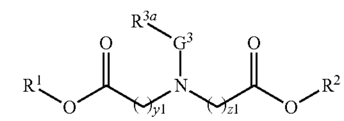

(IH)

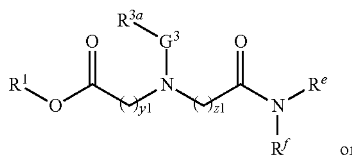

or (IJ)

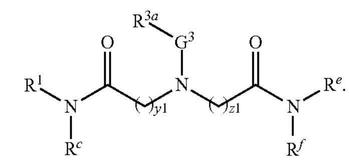

wherein y1 and z1 are each independently integers ranging from 2 to 12, for example an integer from 2 to 6, for example 4.

In some of the foregoing embodiments of structure (I), y1 and z1 are each independently an integer ranging from 2 to 10, 2 to 8, from 4 to 10 or from 4 to 7. For example, in some embodiments of structure (I), y1 is 4, 5, 6, 7, 8, 9, 10, 11 or 12. In some embodiments of structure (I), z1 is 4, 5, 6, 7, 8, 9, 10, 11 or 12. In some embodiments of structure (I), y1 and z1 are the same, while in other embodiments of structure (I) y1 and z1 are different.

In some of the foregoing embodiments of structure (I), $R^1$ or $R^2$, or both is branched $C_6$-$C_{24}$ alkyl. For example, in some embodiments of structure (I), $R^1$ and $R^2$ each, independently have the following structure:

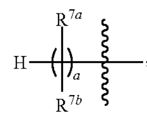

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of structure (I), at least one occurrence of $R^{7a}$ is H. For example, in some embodiments of structure (I), $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of structure (I), $R^1$ or $R^2$, or both, has one of the following structures:

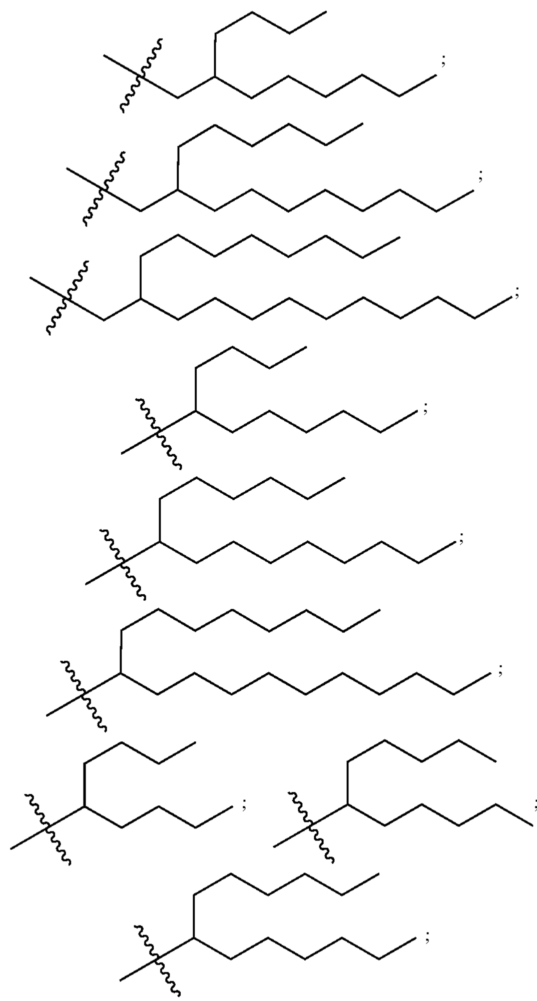

-continued

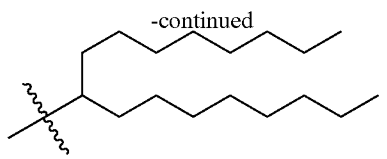

.

In some of the foregoing embodiments of structure (I), $R^b$, $R^c$, $R^e$ and $R^f$ are each independently $C_3$-$C_{12}$ alkyl. For example, in some embodiments of structure (I) $R^b$, $R^c$, $R^e$ and $R^f$ are n-hexyl and in other embodiments of structure (I) $R^b$, $R^c$, $R^e$ and $R^f$ are n-octyl.

In some of the foregoing embodiments of structure (I), $R^{3a}$ is —C(═O)N($R^{4a}$)$R^{5a}$. In more specific embodiments of structure (I), $R^{4a}$ is ethyl, propyl, n-butyl, n-hexyl, n-octyl or n-nonyl. In certain embodiments of structure (I), $R^{5a}$ is H, methyl, ethyl, propyl, n-butyl, n-hexyl or n-octyl. In some of these embodiments of structure (I), $R^{4a}$ and/or $R^{5a}$ is optionally substituted with a substituent, for example hydroxyl.

In some embodiments of structure (I), $R^{3a}$ is —C(═O)$OR^6$. In certain embodiments of structure (I), $R^6$ is benzyl and in other embodiments $R^6$ is H.

In some of the foregoing embodiments of structure (I), $R^{4a}$, $R^{5a}$ and $R^6$ are independently optionally substituted with one or more substituents selected from the group consisting of —$OR^g$, —$NR^gC$(═O)$R^h$, —C(═O)$NR^gR^h$, —C(═O)$R^h$, —OC(═O)$R^h$, —C(═O)$OR^h$ and —$OR^iOH$, wherein:

$R^g$ is, at each occurrence independently H or $C_1$-$C_6$ alkyl;

$R^h$ is at each occurrence independently $C_1$-$C_6$ alkyl; and $R^i$ is, at each occurrence independently $C_1$-$C_6$ alkylene.

In certain specific embodiments of structure (I), $R^{3a}$ has one of the following structures:

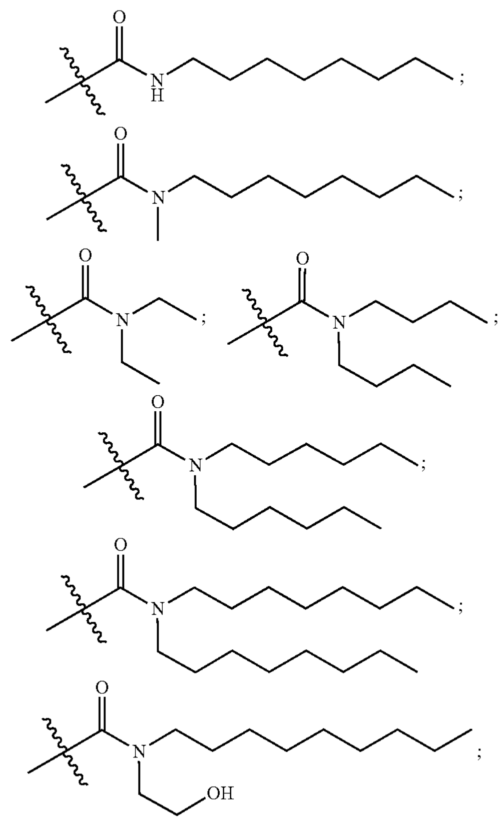

-continued

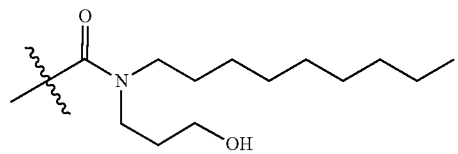

;

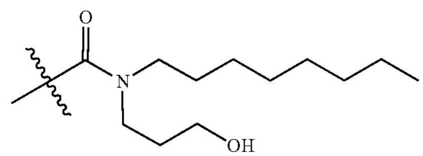

;

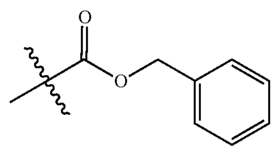

;

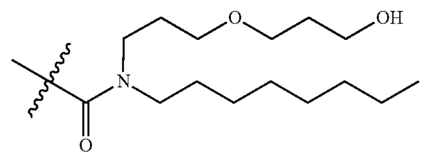

;

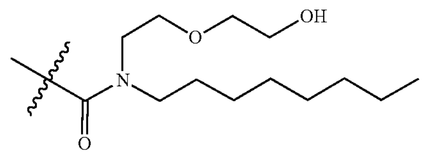

;

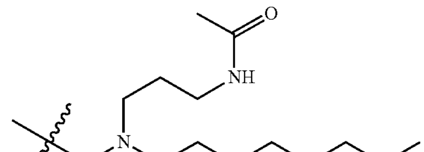

;

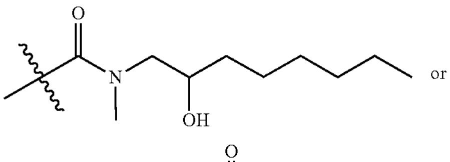

or

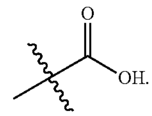

In various different embodiments, the compound has one of the structures set forth in Table 1 below.

TABLE 1
| Representative Compounds of Structure (I) | | |
|---|---|---|
| No. | Structure | Pre-paration Method |
| I-1 | 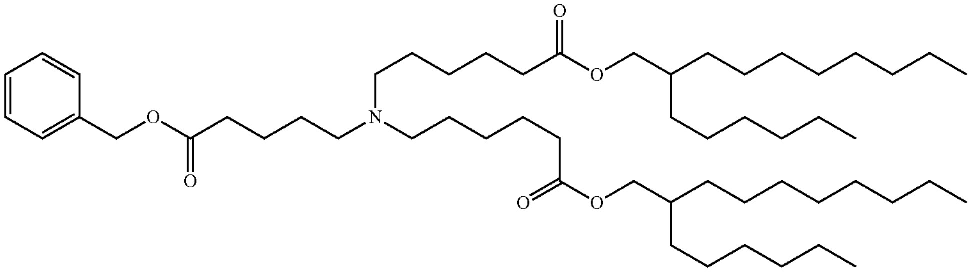 [SMILES: CCCCCCCCC(CCCCCC)COC(=O)CCCCCN(CCCCCC(=O)OCC(CCCCCC)CCCCCCCC)CCCCC(=O)OCc1ccccc1] | A |
| I-2 | 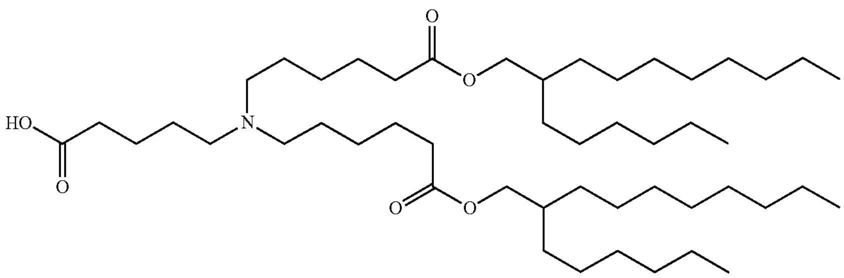 [SMILES: CCCCCCCCC(CCCCCC)COC(=O)CCCCCN(CCCCCC(=O)OCC(CCCCCC)CCCCCCCC)CCCCC(=O)O] | A |
| I-3 | 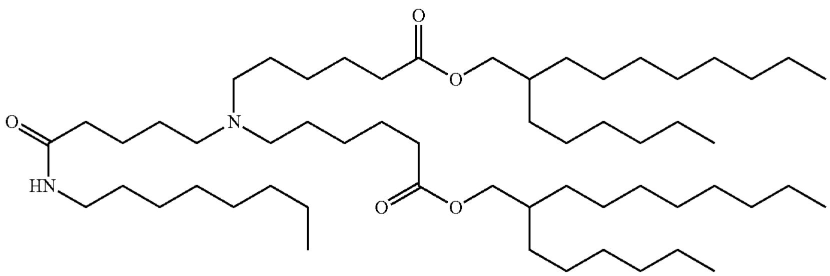 [SMILES: CCCCCCCCNC(=O)CCCCN(CCCCCC(=O)OCC(CCCCCC)CCCCCCCC)CCCCCC(=O)OCC(CCCCCC)CCCCCCCC] | A |
| I-4 | 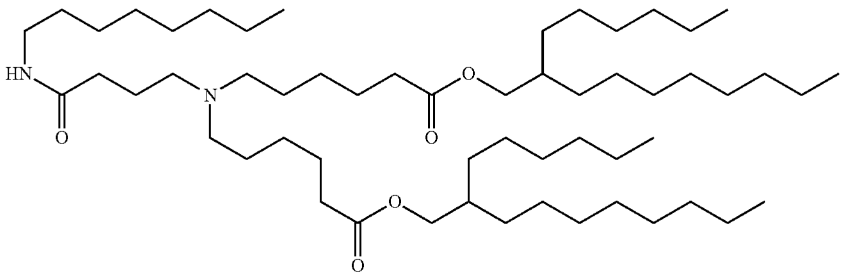 [SMILES: CCCCCCCCNC(=O)CCCN(CCCCCC(=O)OCC(CCCCCC)CCCCCCCC)CCCCCC(=O)OCC(CCCCCC)CCCCCCCC] | A |
| I-5 | 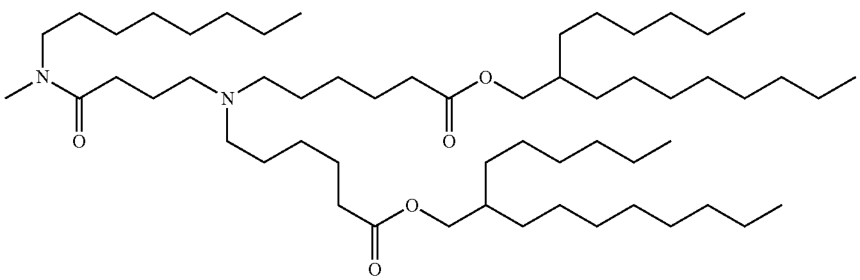 [SMILES: CCCCCCCCC(CCCCCC)COC(=O)CCCCCN(CCCCCC(=O)OCC(CCCCCC)CCCCCCCC)CCCC(=O)N(C)CCCCCCCC] | A |

TABLE 1-continued
| No. | Structure | Preparation Method |
|---|---|---|
| | Representative Compounds of Structure (I) | |
| I-6 | 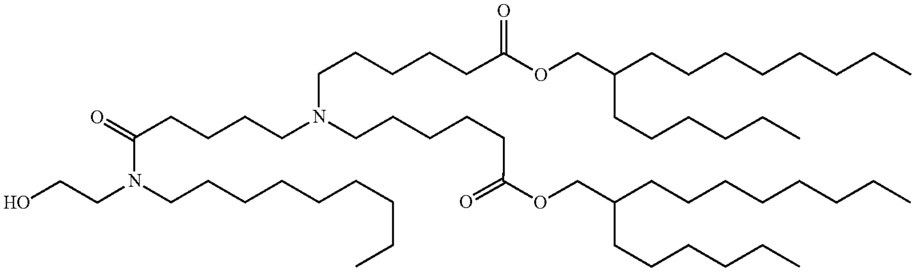 [SMILES: CCCCCCCCCN(CCO)C(=O)CCCCN(CCCCCC(=O)OCC(CCCCCC)CCCCCCCC)CCCCCC(=O)OCC(CCCCCC)CCCCCCCC] | A |
| I-7 | 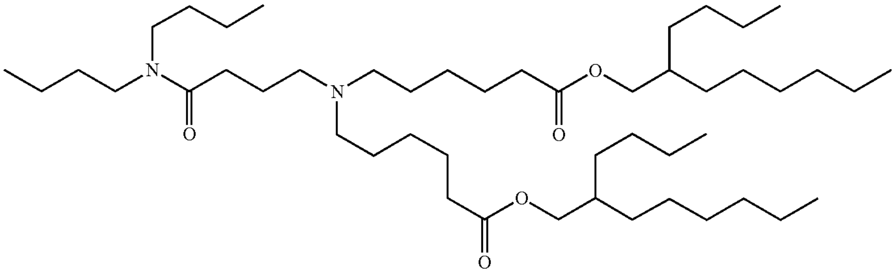 [SMILES: CCCCCCC(CCCC)COC(=O)CCCCCN(CCCCCC(=O)OCC(CCCC)CCCCCC)CCCC(=O)N(CCCC)CCCC] | B |
| I-8 | 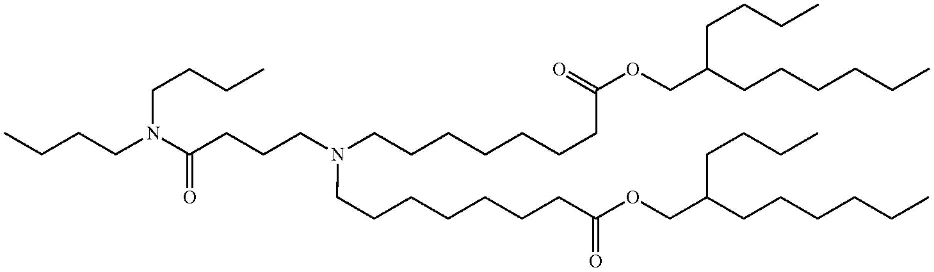 [SMILES: CCCCCCC(CCCC)COC(=O)CCCCCCCN(CCCCCCCC(=O)OCC(CCCC)CCCCCC)CCCC(=O)N(CCCC)CCCC] | B |
| I-9 | 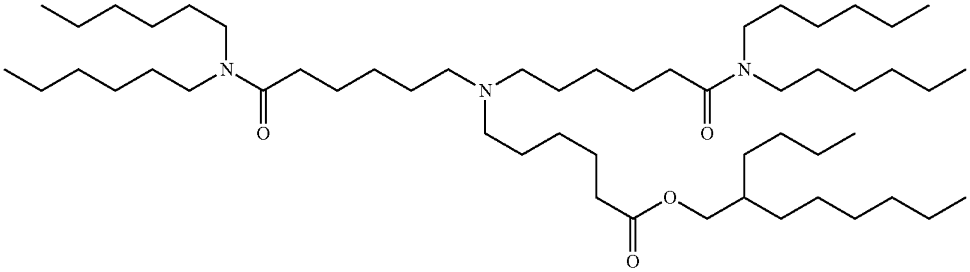 [SMILES: CCCCCCC(CCCC)COC(=O)CCCCCN(CCCCCC(=O)N(CCCCCC)CCCCCC)CCCCCC(=O)N(CCCCCC)CCCCCC] | C |
| I-10 | 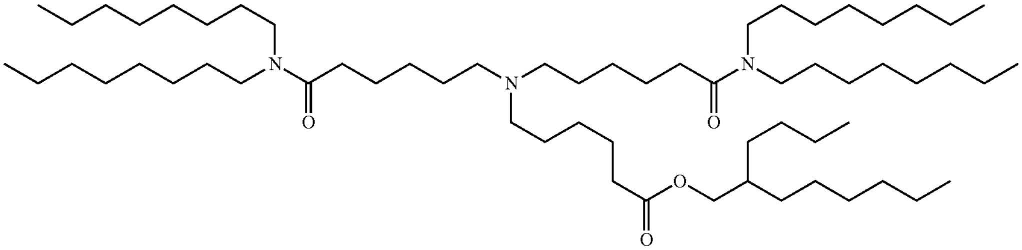 [SMILES: CCCCCCCCN(CCCCCCCC)C(=O)CCCCCN(CCCCCC(=O)OCC(CCCC)CCCCCC)CCCCCC(=O)N(CCCCCCCC)CCCCCCCC] | C |

TABLE 1-continued
| Representative Compounds of Structure (I) | | |
|---|---|---|
| No. | Structure | Preparation Method |
| I-11 | 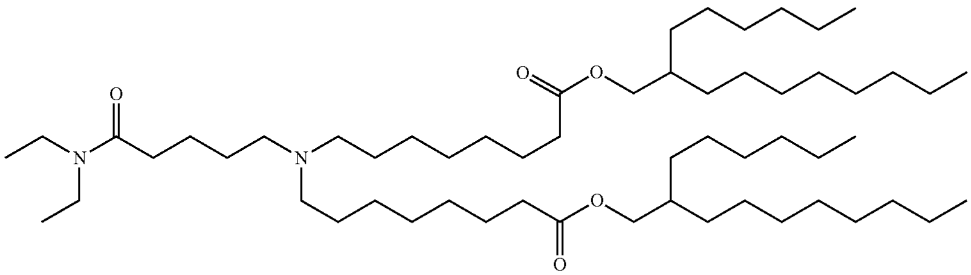 [SMILES: CCCCCCCCC(CCCCCC)COC(=O)CCCCCCCN(CCCCCCCC(=O)OCC(CCCCCC)CCCCCCCC)CCCCC(=O)N(CC)CC] | A |
| I-12 | 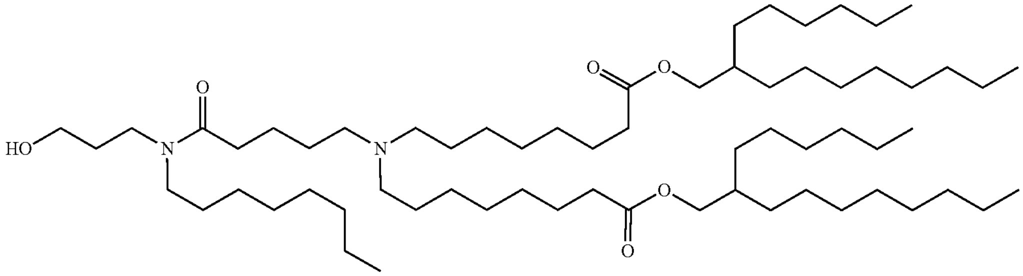 [SMILES: CCCCCCCCC(CCCCCC)COC(=O)CCCCCCCN(CCCCCCCC(=O)OCC(CCCCCC)CCCCCCCC)CCCCC(=O)N(CCCO)CCCCCCCC] | A |
| I-13 | 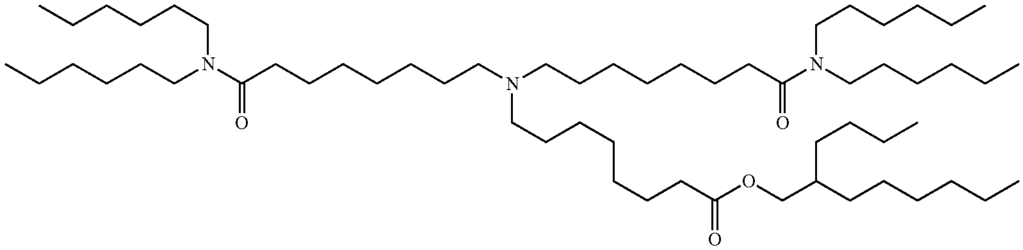 [SMILES: CCCCCCC(CCCC)COC(=O)CCCCCCCN(CCCCCCCC(=O)N(CCCCCC)CCCCCC)CCCCCCCC(=O)N(CCCCCC)CCCCCC] | C |
| I-14 | 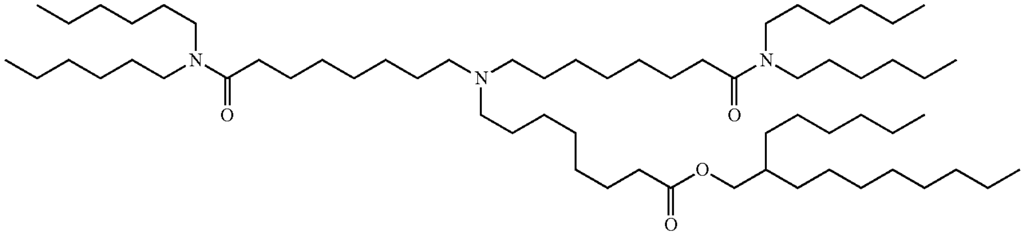 [SMILES: CCCCCCCCC(CCCCCC)COC(=O)CCCCCCCN(CCCCCCCC(=O)N(CCCCCC)CCCCCC)CCCCCCCC(=O)N(CCCCCC)CCCCCC] | C |
| I-15 | 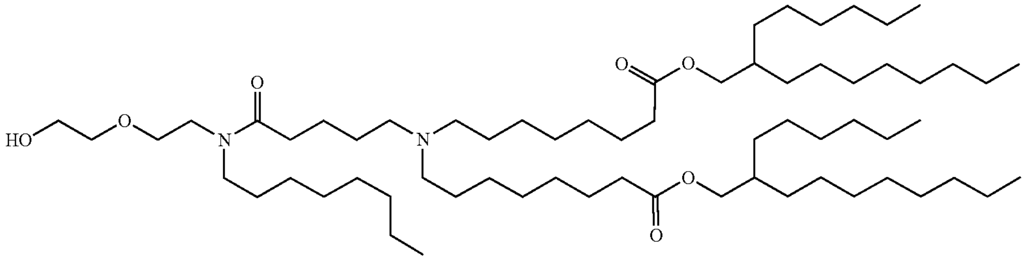 [SMILES: CCCCCCCCC(CCCCCC)COC(=O)CCCCCCCN(CCCCCCCC(=O)OCC(CCCCCC)CCCCCCCC)CCCCC(=O)N(CCCCCCCC)CCOCCO] | A |

TABLE 1-continued

Representative Compounds of Structure (I)

| No. | Structure | Preparation Method |
|---|---|---|
| I-16 | 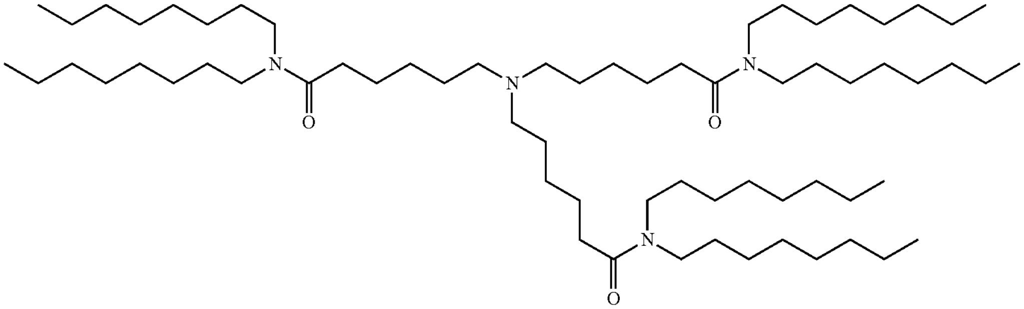 [SMILES: CCCCCCCCN(CCCCCCCC)C(=O)CCCCCN(CCCCCC(=O)N(CCCCCCCC)CCCCCCCC)CCCCCC(=O)N(CCCCCCCC)CCCCCCCC] | C |
| I-17 | 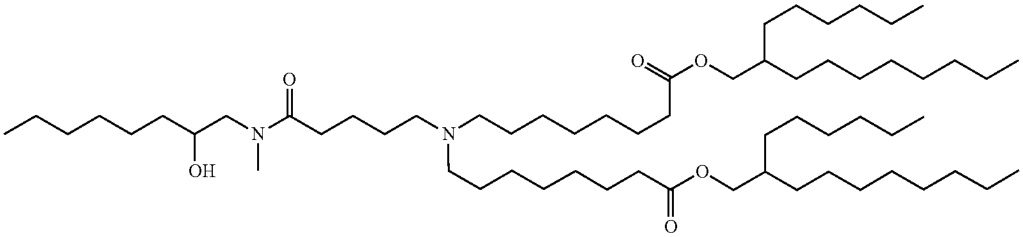 [SMILES: CCCCCCCCC(CCCCCC)COC(=O)CCCCCCCN(CCCCCCCC(=O)OCC(CCCCCC)CCCCCCCC)CCCCC(=O)N(C)CC(O)CCCCCC] | A |
| I-18 | 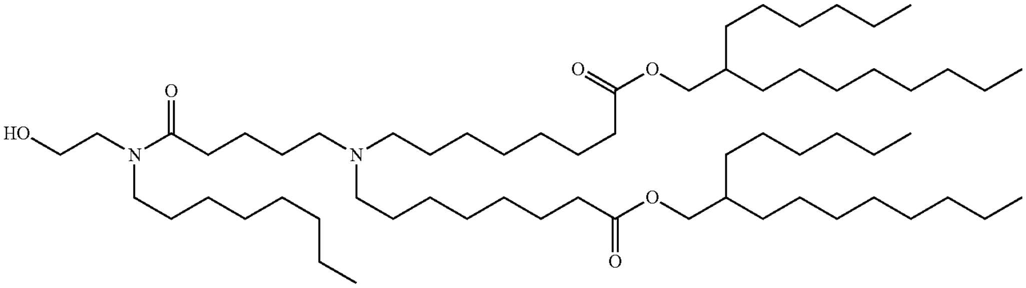 [SMILES: CCCCCCCCC(CCCCCC)COC(=O)CCCCCCCN(CCCCCCCC(=O)OCC(CCCCCC)CCCCCCCC)CCCCC(=O)N(CCO)CCCCCCCC] | A |
| I-19 | 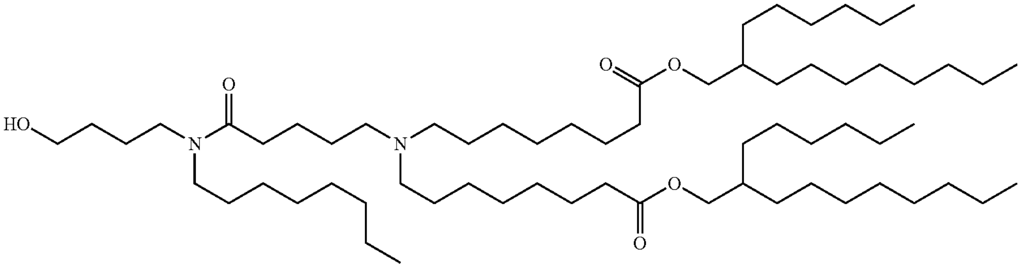 [SMILES: CCCCCCCCC(CCCCCC)COC(=O)CCCCCCCN(CCCCCCCC(=O)OCC(CCCCCC)CCCCCCCC)CCCCC(=O)N(CCCCO)CCCCCCCC] | A |

Compounds of Structure (II)

In one embodiment, the compounds have the following structure (II):

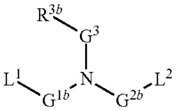

(II)

or a pharmaceutically acceptable salt, tautomer, prodrug or stereoisomer thereof, wherein:

$L^1$ is —O(C═O)$R^1$, —(C═O)O$R^1$, —C(═O)$R^1$, —O$R^1$, —S(O)$_x$$R^1$, —S—S$R^1$, —C(═O)S$R^1$, —SC(═O)$R^1$, —N$R^a$C(═O)$R^1$, —C(═O)N$R^b$$R^c$, —N$R^a$C(═O)N$R^b$$R^c$, —OC(═O)N$R^b$$R^c$ or —N$R^a$C(═O)O$R^1$;

$L^2$ is —O(C═O)$R^2$, —(C═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^e$$R^f$, —N$R^e$C(═O)N$R^e$$R^f$, —OC(═O)N$R^e$$R^f$; —N$R^d$C(═O)O$R^2$ or a direct bond;

$G^{1b}$ and $G^{2b}$ are each independently $C_1$-$C_{12}$ alkylene or $C_2$-$C_{12}$ alkenylene;

$G^3$ is $C_1$-$C_{24}$ alkylene, $C_2$-$C_{24}$ alkenylene, $C_3$-$C_8$ cycloalkylene, $C_3$-$C_8$ cycloalkenylene;

$R^a$, $R^b$, $R^d$ and $R^e$ are each independently H or $C_1$-$C_{12}$ alkyl or $C_2$-$C_{12}$ alkenyl;

$R^c$ and $R^f$ are each independently $C_1$-$C_{12}$ alkyl or $C_2$-$C_{12}$ alkenyl;

$R^1$ and $R^2$ are each independently branched $C_6$-$C_{24}$ alkyl or branched $C_6$-$C_{24}$ alkenyl;

$R^{3b}$ is —$NR^{4b}C(=O)R^{5b}$;

$R^{4b}$ is H, $C_1$-$C_{12}$ alkyl or $C_2$-$C_{12}$ alkenyl;

$R^{5b}$ is $C_2$-$C_{12}$ alkyl or $C_2$-$C_{12}$ alkenyl when $R^{4b}$ is H; or $R^5$ is $C_1$-$C_{12}$ alkyl or $C_2$-$C_{12}$ alkenyl when $R^{4b}$ is $C_1$-$C_{12}$ alkyl or $C_2$-$C_{12}$ alkenyl; and x is 0, 1 or 2, and wherein each alkyl, alkenyl, alkylene, alkenylene, cycloalkylene and cycloalkenylene is independently substituted or unsubstituted.

In certain embodiments of structure (II), $G^3$ is unsubstituted. In more specific embodiments of structure (II) $G^3$ is $C_1$-$C_{12}$ alkylene, for example, $G^3$ is $C_3$-$C_5$ alkylene or $G^3$ is $C_3$-$C_{12}$ alkylene.

In some of the foregoing embodiments, the compound has the following structure (IIA):

(IA)

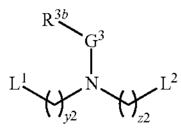

wherein y2 and z2 are each independently integers ranging from 1 to 12.

In some of the foregoing embodiments of structure (II), $L^1$ and $L^2$ are each independently —$O(C=O)R^1$ or —$(C=O)OR^1$.

In other embodiments of the foregoing, the compound has one of the following structures (IIB) or (IIC):

(IIB)

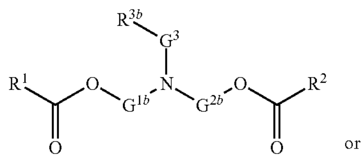

or (IIC)

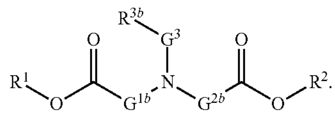

In some of the foregoing embodiments, the compound has structure (IIB), in other embodiments, the compound has structure (IIC).

In some embodiments, the compound has one of the following structures (IID) or (IIE):

(IID)

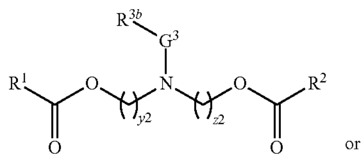

or

-continued (IIE)

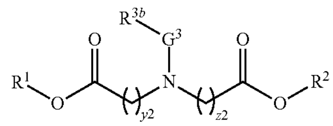

wherein y2 and z2 are each independently integers ranging from 1 to 12.

In some of the foregoing embodiments of structure (II), y2 and z2 are each independently an integer ranging from 2 to 12, for example from 2 to 10, from 2 to 8, from 4 to 7 or from 4 to 10. For example, in some embodiments of structure (II), y2 is 4, 5, 6, 7, 8, 9, 10, 11 or 12. In some embodiments of structure (II), z2 is 4, 5, 6, 7, 8, 9, 10, 11 or 12. In some embodiments of structure (II), y2 and z2 are the same, while in other embodiments of structure (II), y2 and z2 are different.

In some of the foregoing embodiments of structure (II), $R^1$ or $R^2$, or both is branched $C_6$-$C_{24}$ alkyl. For example, in some embodiments of structure (II), $R^1$ and $R^2$ each, independently have the following structure:

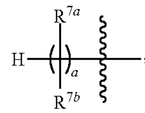

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of structure (II), at least one occurrence of $R^{7a}$ is H. For example, in some embodiments of structure (II), $R^{7a}$ is H at each occurrence. In other different embodiments of the foregoing, at least one occurrence of $R^{7b}$ is $C_1$-$C_8$ alkyl. For example, in some embodiments of structure (II), $C_1$-$C_8$ alkyl is methyl, ethyl, n-propyl, iso-propyl, n-butyl, iso-butyl, tert-butyl, n-hexyl or n-octyl.

In different embodiments of structure (II), $R^1$ or $R^2$, or both, has one of the following structures:

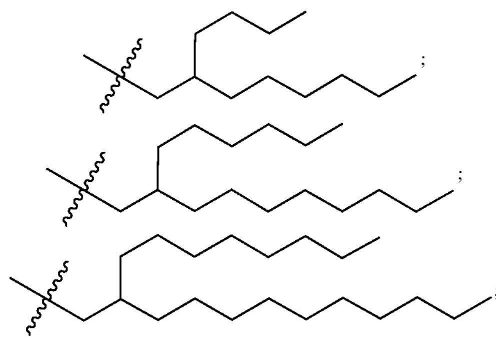

-continued

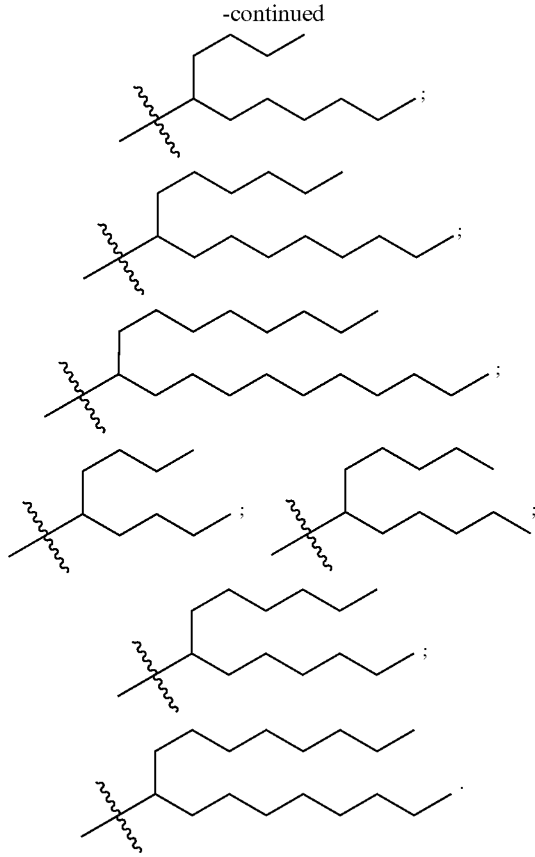

In some of the foregoing embodiments of structure (II), $R^{4b}$ is H, methyl, ethyl, propyl or octyl. In some embodiments of structure (II), $R^{5b}$ is methyl, ethyl, propyl, heptyl or octyl, for example n-heptyl or n-octyl.

In certain related embodiments of structure (II), $R^{4b}$ and $R^{5b}$ are independently optionally substituted with one or more substituents selected from the group consisting of $—OR^g$, $—NR^gC(=O)R^h$, $—C(=O)NR^gR^h$, $—C(=O)R^h$, $—OC(=O)R^h$, $—C(=O)OR^h$ and $OR^iOH$, wherein:

$R^g$ is, at each occurrence independently H or $C_1$-$C_6$ alkyl;

$R^h$ is at each occurrence independently $C_1$-$C_6$ alkyl; and $R^i$ is, at each occurrence independently $C_1$-$C_6$ alkylene.

In certain specific embodiments of structure (II), $R^{3b}$ has one of the following structures:

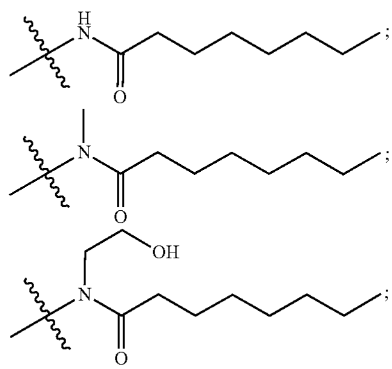

-continued

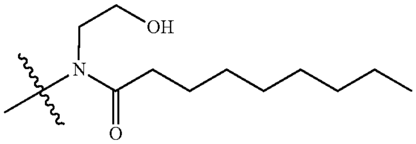

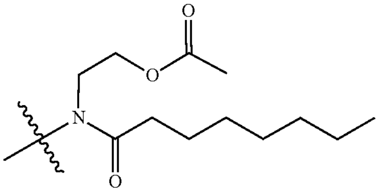

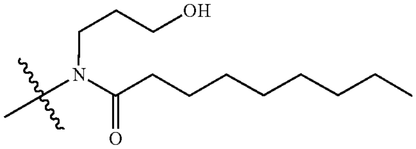

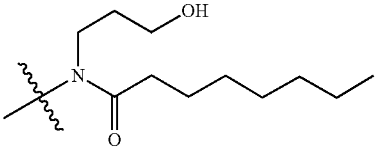

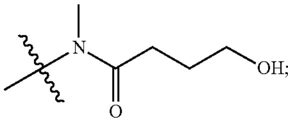

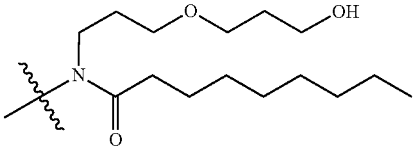

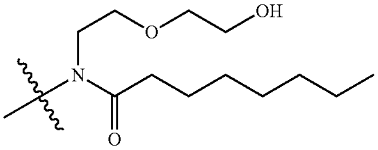

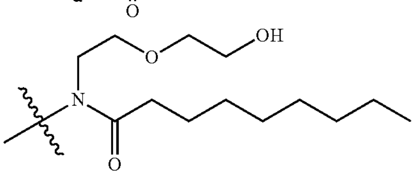

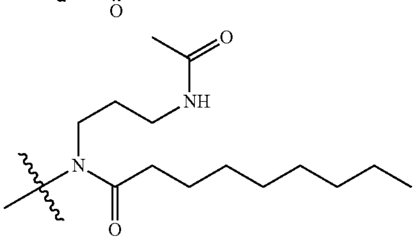

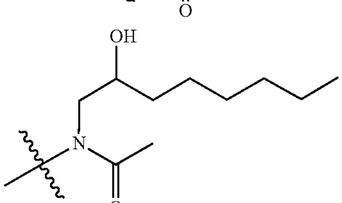

or

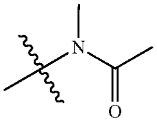

In various different embodiments, the compound of structure (II) has one of the structures set forth in Table 2 below.

TABLE 2
| Representative Compounds of Structure II | | |
|---|---|---|
| No. | Structure | Preparation Method |
| II-1 | 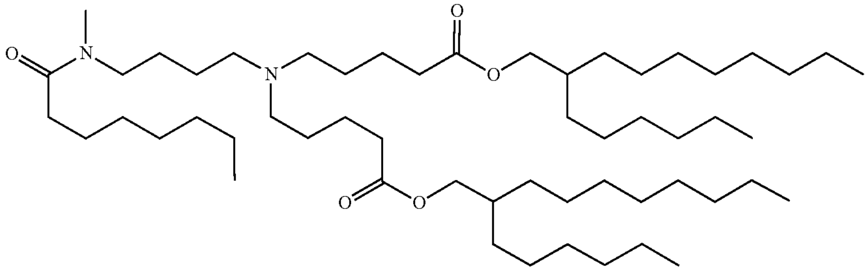 [SMILES: CCCCCCCCC(CCCCCC)COC(=O)CCCCN(CCCCC(=O)OCC(CCCCCC)CCCCCCCC)CCCCN(C)C(=O)CCCCCCC] | D |
| II-2 | 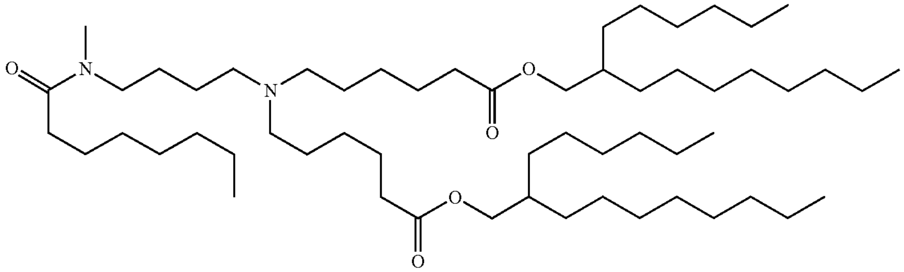 [SMILES: CCCCCCCCC(CCCCCC)COC(=O)CCCCCN(CCCCCC(=O)OCC(CCCCCC)CCCCCCCC)CCCCN(C)C(=O)CCCCCCC] | D |
| II-3 | 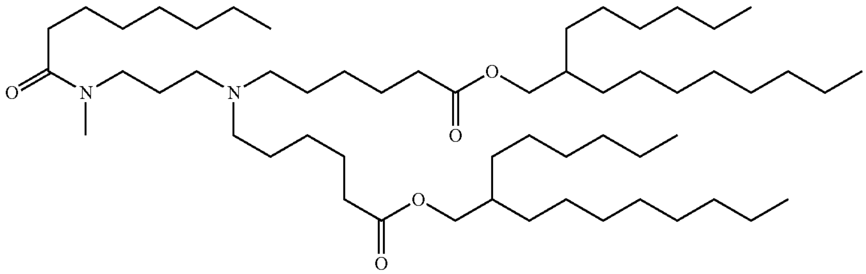 [SMILES: CCCCCCCCC(CCCCCC)COC(=O)CCCCCN(CCCCCC(=O)OCC(CCCCCC)CCCCCCCC)CCCN(C)C(=O)CCCCCCC] | A |
| II-4 | 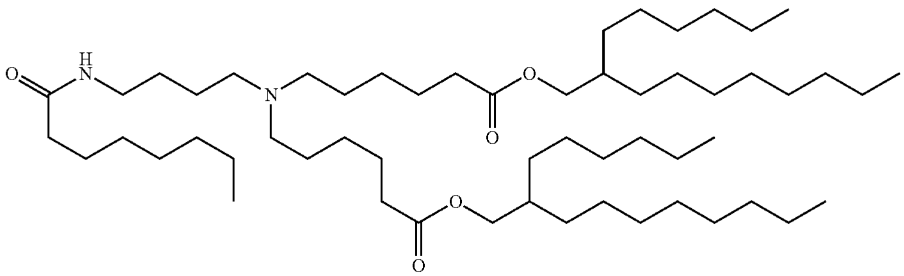 | E |
| II-5 | 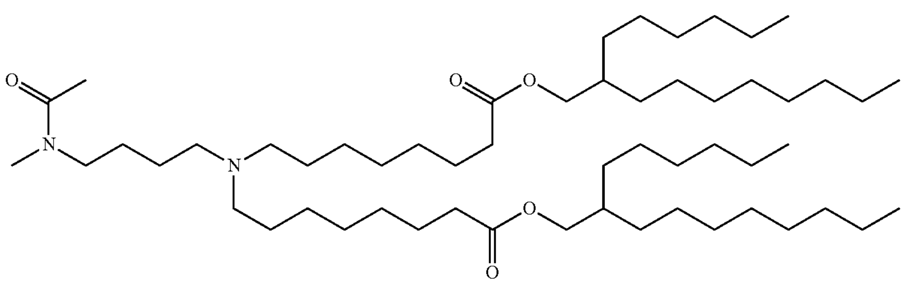 [SMILES: CCCCCCCCC(CCCCCC)COC(=O)CCCCCCCN(CCCCCCCC(=O)OCC(CCCCCC)CCCCCCCC)CCCCN(C)C(C)=O] | F |

TABLE 2-continued
| Representative Compounds of Structure II | | |
|---|---|---|
| No. | Structure | Preparation Method |
| II-6 | 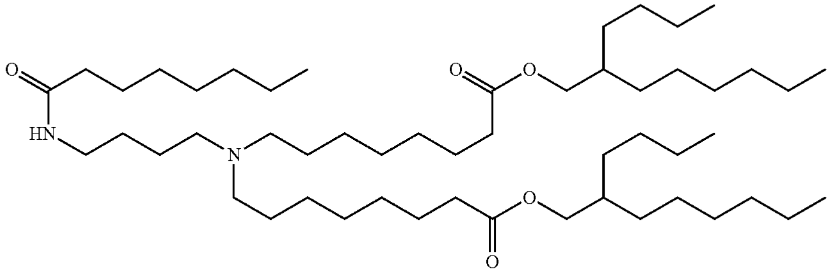 [SMILES: CCCCCCCC(=O)NCCCCN(CCCCCCCC(=O)OCC(CCCC)CCCCCC)CCCCCCCC(=O)OCC(CCCC)CCCCCC] | E |
| II-7 | 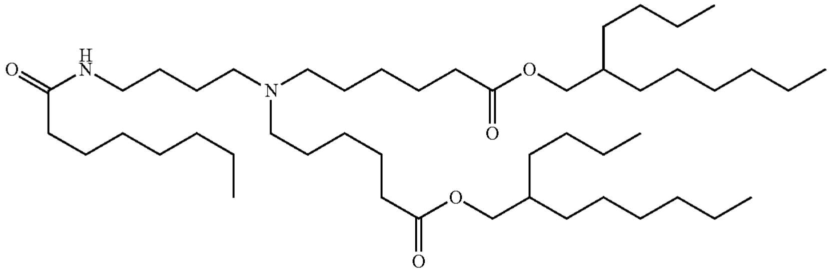 [SMILES: CCCCCCCC(=O)NCCCCN(CCCCCC(=O)OCC(CCCC)CCCCCC)CCCCCC(=O)OCC(CCCC)CCCCCC] | G |
| II-8 | 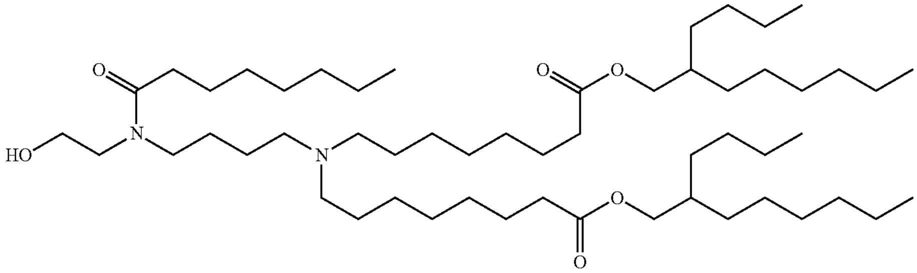 [SMILES: CCCCCCCC(=O)N(CCO)CCCCN(CCCCCCCC(=O)OCC(CCCC)CCCCCC)CCCCCCCC(=O)OCC(CCCC)CCCCCC] | G |
| II-9 | 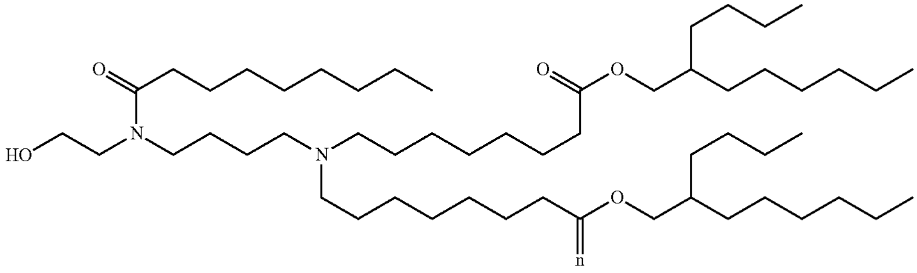 | G |
| II-10 | 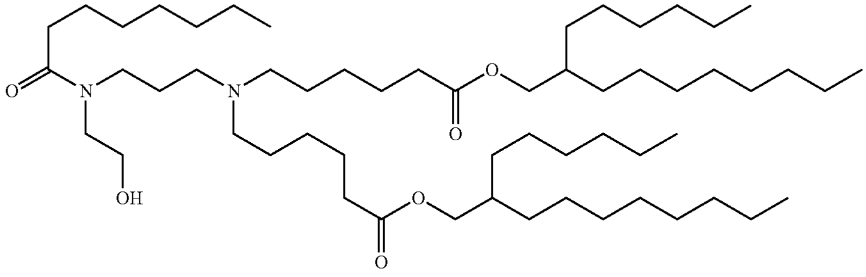 [SMILES: CCCCCCCCC(CCCCCC)COC(=O)CCCCCN(CCCCCC(=O)OCC(CCCCCC)CCCCCCCC)CCCN(CCO)C(=O)CCCCCCC] | G |

TABLE 2-continued
| Representative Compounds of Structure II | | |
|---|---|---|
| No. | Structure | Preparation Method |
| II-11 | 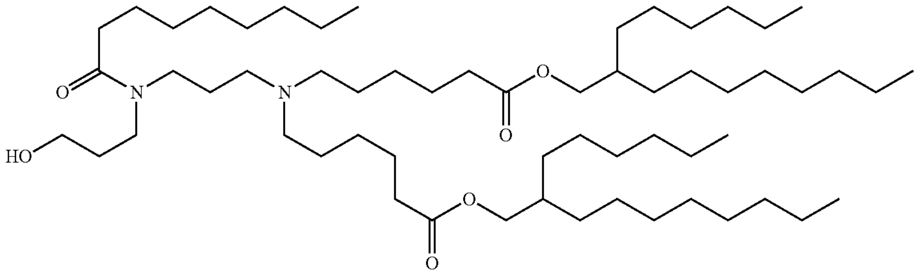 [SMILES: CCCCCCCCC(=O)N(CCCO)CCCN(CCCCCC(=O)OCC(CCCCCC)CCCCCCCC)CCCCCC(=O)OCC(CCCCCC)CCCCCCCC] | G |
| II-12 | 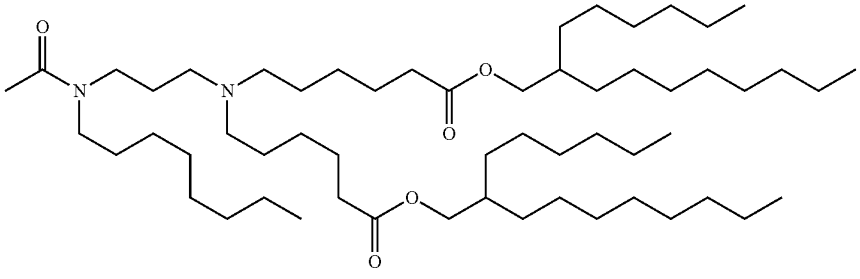 [SMILES: CCCCCCCCC(CCCCCC)COC(=O)CCCCCN(CCCCCC(=O)OCC(CCCCCC)CCCCCCCC)CCCN(CCCCCCCC)C(C)=O] | G |
| II-13 | 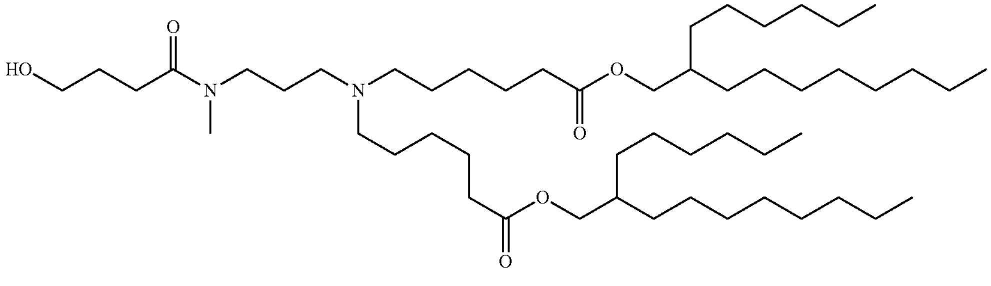 [SMILES: CCCCCCCCC(CCCCCC)COC(=O)CCCCCN(CCCCCC(=O)OCC(CCCCCC)CCCCCCCC)CCCN(C)C(=O)CCCO] | D |
| II-14 | 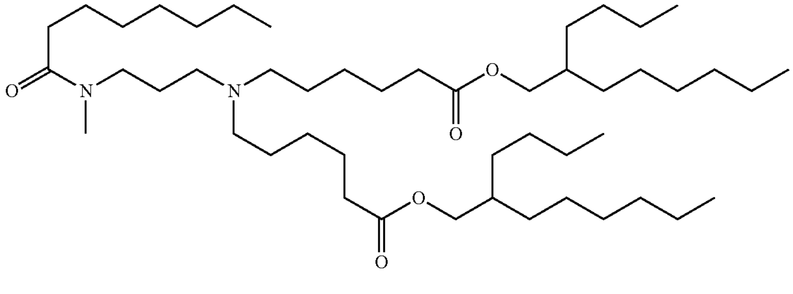 [SMILES: CCCCCCCC(=O)N(C)CCCN(CCCCCC(=O)OCC(CCCC)CCCCCC)CCCCCC(=O)OCC(CCCC)CCCCCC] | D |
| II-15 | 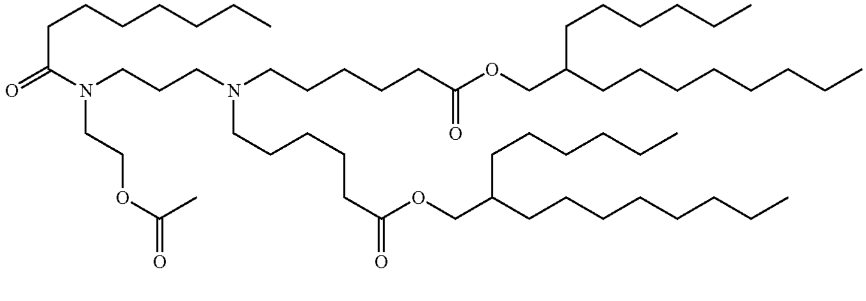 [SMILES: CCCCCCCCC(CCCCCC)COC(=O)CCCCCN(CCCCCC(=O)OCC(CCCCCC)CCCCCCCC)CCCN(CCOC(C)=O)C(=O)CCCCCCC] | G |

TABLE 2-continued
| Representative Compounds of Structure II | | |
|---|---|---|
| No. | Structure | Preparation Method |
| II-16 | 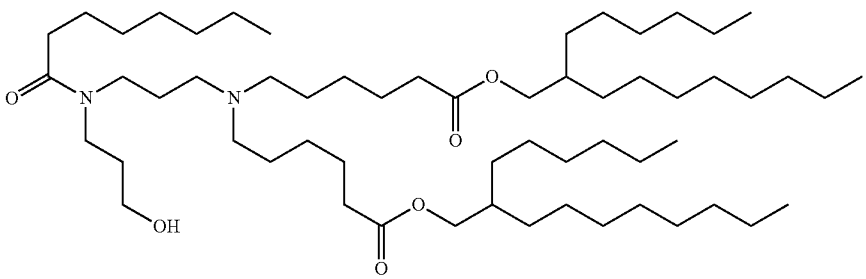 [SMILES: CCCCCCCCC(CCCCCC)COC(=O)CCCCCN(CCCCCC(=O)OCC(CCCCCC)CCCCCCCC)CCCN(CCCO)C(=O)CCCCCCC] | G |
| II-17 | 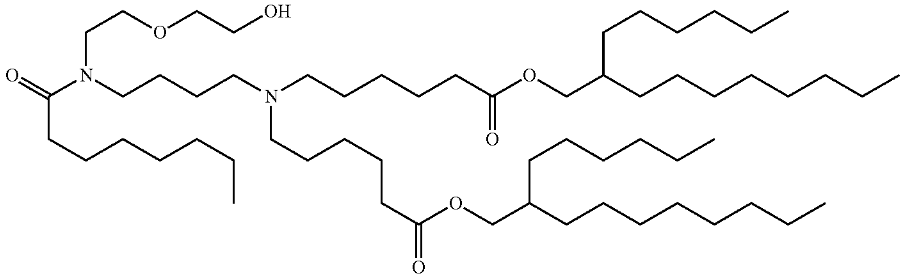 [SMILES: CCCCCCCCC(CCCCCC)COC(=O)CCCCCN(CCCCCC(=O)OCC(CCCCCC)CCCCCCCC)CCCCN(CCOCCO)C(=O)CCCCCCC] | G |
| II-18 | 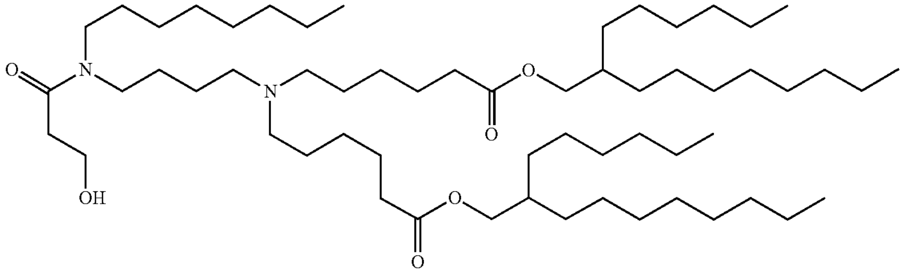 [SMILES: CCCCCCCCC(CCCCCC)COC(=O)CCCCCN(CCCCCC(=O)OCC(CCCCCC)CCCCCCCC)CCCCN(CCCCCCCC)C(=O)CCO] | G |
| II-19 | 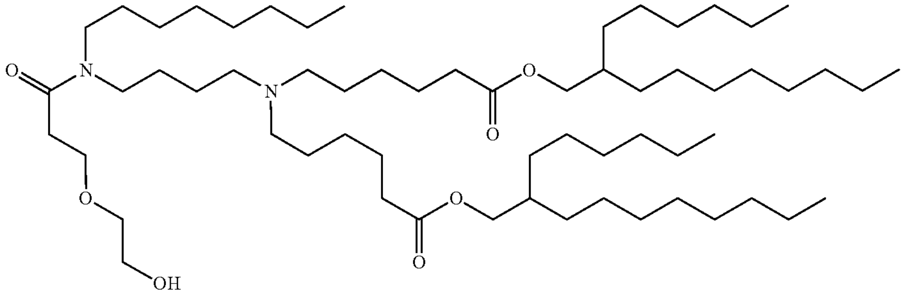 [SMILES: CCCCCCCCC(CCCCCC)COC(=O)CCCCCN(CCCCCC(=O)OCC(CCCCCC)CCCCCCCC)CCCCN(CCCCCCCC)C(=O)CCOCCO] | G |
| II-20 | 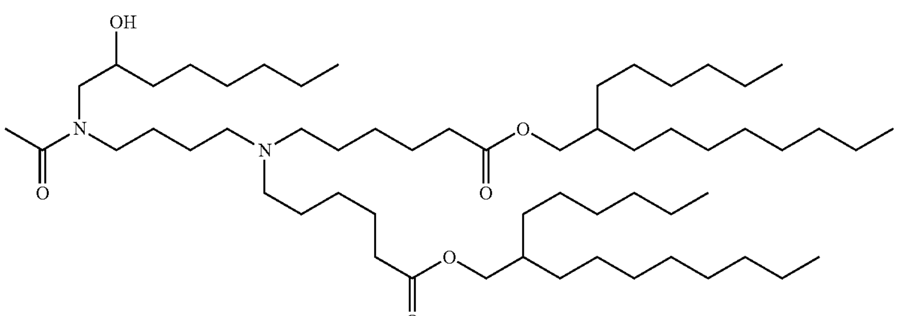 | G |

It is understood that any embodiment of the compounds of structure (I) or (II), as set forth above, and any specific substituent and/or variable in the compound structure (I) or (II), as set forth above, may be independently combined with other embodiments and/or substituents and/or variables of compounds of structure (I) or (II) to form embodiments of the inventions not specifically set forth above. In addition, in the event that a list of substituents and/or variables is listed for any particular R group, L group, G group, or variables a, x, y, or z in a particular embodiment and/or claim, it is understood that each individual substituent and/or variable may be deleted from the particular embodiment and/or claim and that the remaining list of substituents and/or variables will be considered to be within the scope of the invention.

It is understood that in the present description, combinations of substituents and/or variables of the depicted formulae are permissible only if such contributions result in stable compounds.

In some embodiments, compositions comprising any one or more of the compounds of structure (I) or (II) and a therapeutic agent are provided. For example, in some embodiments, the compositions comprise any of the compounds of structure (I) or (II) and a therapeutic agent and one or more excipient selected from neutral lipids, steroids and polymer conjugated lipids. Other pharmaceutically acceptable excipients and/or carriers are also included in various embodiments of the compositions.

In some embodiments, the neutral lipid is selected from DSPC, DPPC, DMPC, DOPC, POPC, DOPE and SM. In some embodiments, the neutral lipid is DSPC. In various embodiments, the molar ratio of the compound to the neutral lipid ranges from about 2:1 to about 8:1.

In various embodiments, the compositions further comprise a steroid or steroid analogue. In certain embodiments, the steroid or steroid analogue is cholesterol. In some of these embodiments, the molar ratio of the compound to cholesterol ranges from about 5:1 to 1:1.

In various embodiments, the polymer conjugated lipid is a pegylated lipid. For example, some embodiments include a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2',3'-di(tetradecanoyloxy)propyl-1-O-(ω-methoxy(polyethoxy)ethyl)butanedioate (PEG-S-DMG), a pegylated ceramide (PEG-cer), or a PEG dialkoxypropylcarbamate such as ω-methoxy(polyethoxy)ethyl-N-(2,3-di(tetradecanoxy)propyl)carbamate or 2,3-di(tetradecanoxy)propyl-N-(ω-methoxy(polyethoxy)ethyl)carbamate. In various embodiments, the molar ratio of the compound to the pegylated lipid ranges from about 100:1 to about 20:1.

In some embodiments, the composition comprises a pegylated lipid having the following structure (III):

(III)

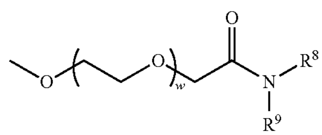

or a pharmaceutically acceptable salt, tautomer or stereoisomer thereof, wherein:

$R^8$ and $R^9$ are each independently a straight or branched, alkyl, alkenyl or alkynyl containing from 10 to 30 carbon atoms, wherein the alkyl, alkenyl or alkynyl is optionally interrupted by one or more ester bonds; and w has a mean value ranging from 30 to 60.

In some embodiments, $R^8$ and $R^9$ are each independently straight alkyl containing from 12 to 16 carbon atoms. In some embodiments, w has a mean value ranging from 43 to 53. In other embodiments, the average w is about 45. In other different embodiments, the average w is about 49.

In some embodiments, lipid nanoparticles (LNPs) comprising any one or more of the compounds of structure (I) or (II) and a therapeutic agent are provided. For example, in some embodiments, the LNPs comprise any of the compounds of structure (I) or (II) and a therapeutic agent and one or more excipient selected from neutral lipids, steroids and polymer conjugated lipids.

In some embodiments of the LNPs, the neutral lipid is selected from DSPC, DPPC, DMPC, DOPC, POPC, DOPE and SM. In some embodiments, the neutral lipid is DSPC. In various embodiments, the molar ratio of the compound to the neutral lipid ranges from about 2:1 to about 8:1.

In various embodiments of the LNPs, the compositions further comprise a steroid or steroid analogue. In certain embodiments, the steroid or steroid analogue is cholesterol. In some of these embodiments, the molar ratio of the compound to cholesterol ranges from about 5:1 to 1:1.

In various embodiments of the LNPs, the polymer conjugated lipid is a pegylated lipid. For example, some embodiments include a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2',3'-di(tetradecanoyloxy)propyl-1-O-(ω-methoxy(polyethoxy)ethyl)butanedioate (PEG-S-DMG), a pegylated ceramide (PEG-cer), or a PEG dialkoxypropylcarbamate such as ω-methoxy(polyethoxy)ethyl-N-(2,3-di(tetradecanoxy)propyl)carbamate or 2,3-di(tetradecanoxy)propyl-N-(ω-methoxy(polyethoxy)ethyl)carbamate. In various embodiments, the molar ratio of the compound to the pegylated lipid ranges from about 100:1 to about 20:1.

In some embodiments, the LNPs comprise a pegylated lipid having the following structure (III):

(III)

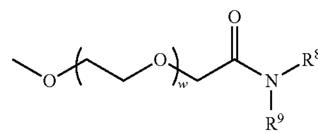

or a pharmaceutically acceptable salt, tautomer or stereoisomer thereof, wherein:

$R^8$ and $R^9$ are each independently a straight or branched, alkyl, alkenyl or alkynyl containing from 10 to 30 carbon atoms, wherein the alkyl, alkenyl or alkynyl is optionally interrupted by one or more ester bonds; and w has a mean value ranging from 30 to 60.

In some embodiments, $R^8$ and $R^9$ are each independently straight alkyl containing from 12 to 16 carbon atoms. In some embodiments, w has a mean value ranging from 43 to 53. In other embodiments, the average w is about 45. In other different embodiments, the average w is about 49.

Preparation methods for the above lipids, lipid nanoparticles and compositions are described herein below and/or known in the art, for example, in PCT Pub. No. WO 2015/199952 and WO 2017/004143, both of which are incorporated herein by reference in their entirety.

In some embodiments of the foregoing composition, the therapeutic agent comprises a nucleic acid. For example, in some embodiments, the nucleic acid is selected from antisense and messenger RNA.

In other different embodiments, the invention is directed to a method for administering a therapeutic agent to a patient in need thereof, the method comprising preparing or providing any of the foregoing compositions and administering the composition to the patient For the purposes of administration, the compounds of structure (I) or (II) (typically in the form of lipid nanoparticles in combination with a therapeutic agent) may be administered as a raw chemical or may be formulated as pharmaceutical compositions. Pharmaceutical compositions of embodiments of the present invention comprise a compound of structure (I) or (II) (e.g., as a component in an LNP) and one or more pharmaceutically acceptable carrier, diluent or excipient. The compound of structure (I) or (II) is present in the composition in an amount which is effective to form a lipid nanoparticle and deliver the therapeutic agent, e.g., for treating a particular disease or condition of interest. Appropriate concentrations and dosages can be readily determined by one skilled in the art.

Administration of the compositions and/or LNPs of embodiments of the invention can be carried out via any of the accepted modes of administration of agents for serving similar utilities. The pharmaceutical compositions of embodiments of the invention may be formulated into preparations in solid, semi-solid, liquid or gaseous forms, such as tablets, capsules, powders, granules, ointments, solutions, suspensions, suppositories, injections, inhalants, gels, microspheres, and aerosols. Typical routes of administering such pharmaceutical compositions include, without limitation, oral, topical, transdermal, inhalation, peritoneal, sublingual, buccal, rectal, vaginal, and intranasal. The term peritoneal as used herein includes subcutaneous injections, intravenous, intramuscular, intradermal, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of structure (I) or (II) in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of structure (I) or (II) (e.g., in the form of an LNP comprising a therapeutic agent), or a pharmaceutically acceptable salt thereof, for treatment of a disease or condition of interest in accordance with the teachings of embodiments of this invention.

A pharmaceutical composition of embodiments of the invention may be in the form of a solid or liquid. In one aspect, the carrier(s) are particulate, so that the compositions are, for example, in tablet or powder form. The carrier(s) may be liquid, with the compositions being, for example, oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds or LNPs, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of embodiments of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose; agents to act as cryoprotectants such as sucrose or trehalose. The peritoneal preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of embodiments of the invention intended for either peritoneal or oral administration should contain an amount of a compound of structure (I) or (II) such that a suitable LNP will be obtained.

The pharmaceutical composition of embodiments of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of embodiments of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of embodiments of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of embodiments of the invention in solid or liquid form may include an agent that binds to the compound of structure (I) or (II) and thereby assists in the delivery of the compound. Suitable agents that may act in this capacity include a monoclonal or polyclonal antibody, or a protein.

The pharmaceutical composition of embodiments of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols comprising compounds of structure (I) or (II) may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of embodiments of the invention may be prepared by methodology well known in the pharmaceutical art. For example, a pharmaceutical composition intended to be administered by injection can be prepared by combining the lipid nanoparticles of the invention with sterile, distilled water or other carrier so as to form a solution. A surfactant may be added to facilitate the formation of a homogeneous solution or suspension. Surfactants are compounds that non-covalently interact with the compound of structure (I) or (II) so as to facilitate dissolution or homogeneous suspension of the compound in the aqueous delivery system.

The compositions of embodiments of the invention, or their pharmaceutically acceptable salts, are administered in a therapeutically effective amount, which will vary depending upon a variety of factors including the activity of the specific therapeutic agent employed; the metabolic stability and length of action of the therapeutic agent; the age, body weight, general health, sex, and diet of the patient; the mode and time of administration; the rate of excretion; the drug combination; the severity of the particular disorder or condition; and the subject undergoing therapy.

Compositions of embodiments of the invention may also be administered simultaneously with, prior to, or after administration of one or more other therapeutic agents. Such combination therapy includes administration of a single pharmaceutical dosage formulation of a composition of embodiments of the invention and one or more additional active agents, as well as administration of the composition of the invention and each active agent in its own separate pharmaceutical dosage formulation. For example, a composition of embodiments of the invention and the other active agent can be administered to the patient together in a single oral dosage composition such as a tablet or capsule, or each agent administered in separate oral dosage formulations. Where separate dosage formulations are used, the compounds of structure (I) or (II) and one or more additional active agents can be administered at essentially the same time, i.e., concurrently, or at separately staggered times, i.e., sequentially; combination therapy is understood to include all these regimens.

Preparation methods for the above compounds and compositions are described herein below and/or known in the art.

It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of structure (I) or (II) which exist in free base or acid form can be converted to their pharmaceutically acceptable salts by treatment with the appropriate inorganic or organic base or acid by methods known to one skilled in the art. Salts of the compounds of structure (I) or (II) can be converted to their free base or acid form by standard techniques.

The following General Reaction Schemes illustrate methods to make compounds of structure (I) or (II):

(I)

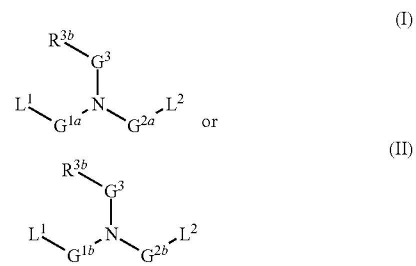

or (II)

or a pharmaceutically acceptable salt, tautomer or stereoisomer thereof, wherein $R^{3a}$, $R^{3b}$, $L^1$, $L^2$, $G^{1a}$, $G^{1b}$, $G^{2a}$, $G^{2b}$ and $G^3$ are as defined herein. It is understood that one skilled in the art may be able to make these compounds by similar methods or by combining other methods known to one skilled in the art. It is also understood that one skilled in the art would be able to make, in a similar manner as described below, other compounds of structure (I) or (II) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

GENERAL REACTION SCHEME 1

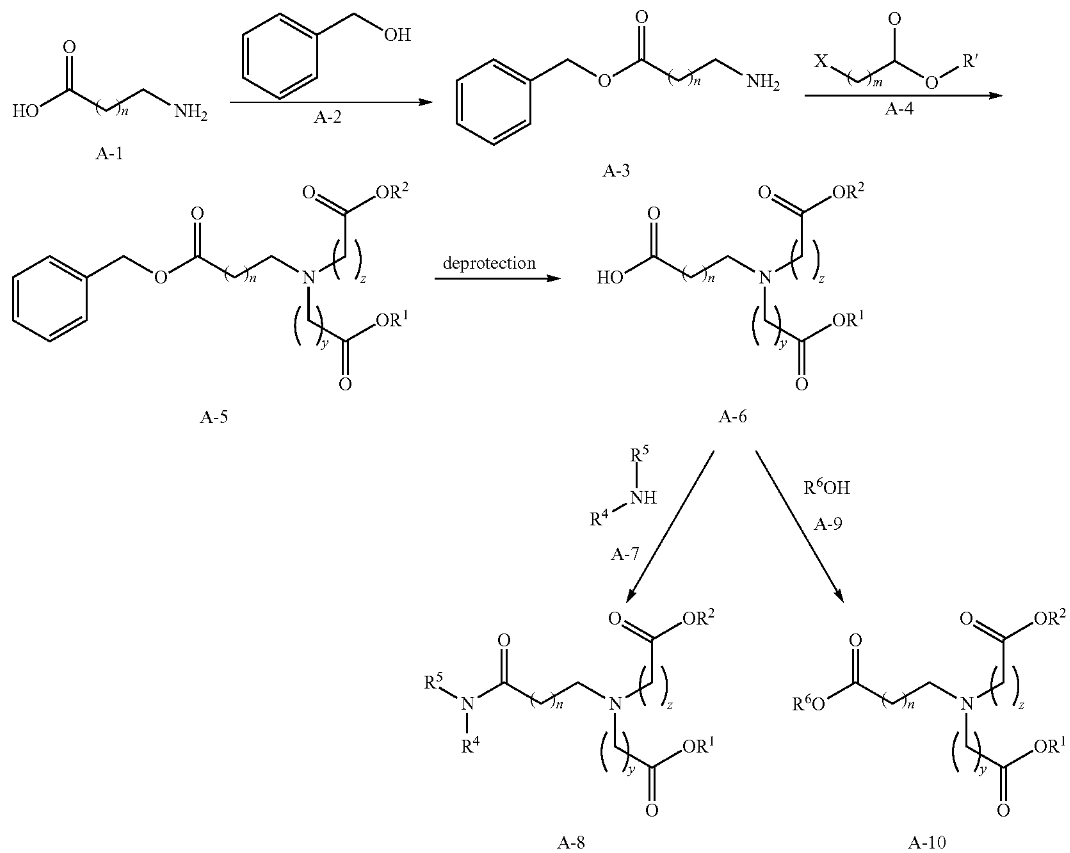

A-1 A-3 A-5 A-6 A-8 A-10

General Reaction Scheme 1 ("Method A") provides an exemplary method for preparation of compounds of structure (I). $R^1$, $R^2$, $R^4$, $R^5$, $R^6$, y and z in General Reaction Scheme 1 are as defined herein. $R^1$, X, m and n refer to variables selected such that A-5, A-6, A-8, and A-10 are compounds having a structure (I). For example, R' is $R^1$ or $R^2$, X is Br, m is y or z, and n is an integer ranging from 0 to 23. Compounds of structure A-1 are purchased or prepared according to methods known in the art. Amine/acid A-1 is protected with alcohol A-2 (e.g., benzyl alcohol) using suitable conditions and reagents (e.g., p-TSA) to obtain ester/amine A-3. Ester/amine A-3 is coupled with ester A-4 (e.g., using DIPEA) to afford benzyl ester A-5. Compound A-5 is optionally deprotected using appropriate conditions (e.g., Pd/C, $H_2$) to obtain acid A-6. The acid A-6 can be reacted with amine A-7 (e.g., using oxalyl chloride/DMF) to obtain amide A-8, or alternatively, reacted with alcohol A-9 (e.g., using DCC/DMAP) to yield ester A-10. Each of A-5, A-6, A-8, and A-10 are compounds of structure (I).

GENERAL REACTION SCHEME 2

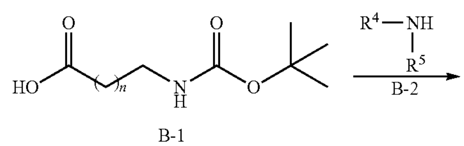

B-1

-continued

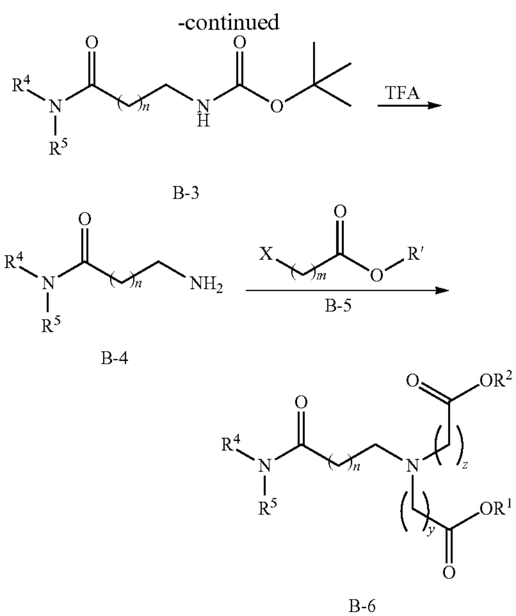

B-3 B-4 B-6

General Reaction Scheme 2 ("Method B") provides an exemplary method for preparation of compounds of structure (I). $R^1$, $R^2$, $R^4$, $R^5$, y and z in General reaction Scheme 2 are as defined herein. R', X, m and n refer to variables selected such that B-6 is a compound having a structure (I). For example, R' is $R^1$ or $R^2$, X is Br, m is y or z, and n is an integer ranging from 0 to 23. Compounds of structure B-1 are purchased or prepared according to methods known in the art. Reaction of protected amine/acid B-1 with amine B-2 is carried out under appropriate coupling conditions (e.g., NHS, DCC) to yield amide B-3. Following a deprotection step using acidic conditions (e.g., TFA), amine B-4 is coupled with ester B-5 under suitable conditions (e.g., DIPEA) to yield B-6, a compound of structure (I).

GENERAL REACTION SCHEME 4

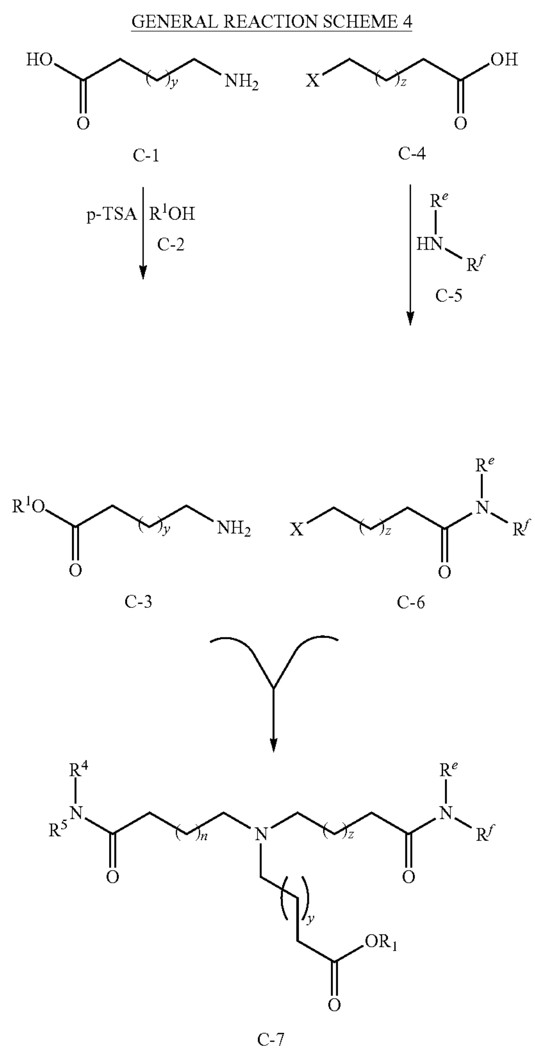

General Reaction Scheme 3 ("Method C") provides an exemplary method for preparation of compounds of structure (I). $R^1$, $R^4$, $R^5$, $R^e$, $R^f$, y and z in General reaction Scheme 3 are as defined herein. $R^1$, X, m and n refer to variables selected such that C-7 is a compound having a structure (I). For example, R' is $R^1$ or $R^2$, X is Br, m is y or z, and n is an integer ranging from 0 to 23. Compounds of structure C-1, C-2, C-4 and C-5 are purchased or prepared according to methods known in the art. Reaction of amine/acid C-1 with alcohol C-2 is carried out under appropriate coupling conditions (e.g., p-TSA) to yield amine/ester C-3. In parallel, amide C-6 is prepared by coupling acid C-4 with amine C-5 under suitable conditions (e.g., oxalyl chloride/DMF). C-3 and C-6 are combined under basic conditions (e.g., DIPEA) to afford C-7, a compound of structure (I).

GENERAL REACTION SCHEME 4

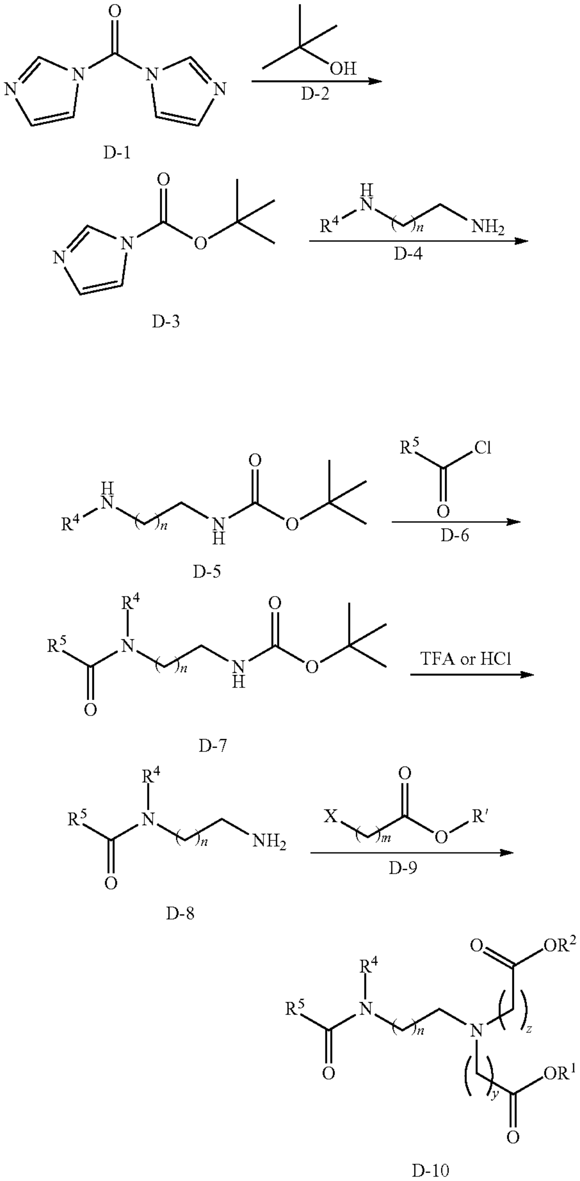

General Reaction Scheme 4 ("Method D") provides an exemplary method for preparation of compounds of structure (II). $R^1$, $R^2$, $R^4$, $R^5$, y and z in General Reaction Scheme 1 are as defined herein. R', X, m and n refer to variables selected such that D-10 is a compound having a structure (I). For example, R' is $R^1$ or $R^2$, X is Br, m is y or z, and n is an integer ranging from 0 to 23. Compounds of structure D-1 are purchased or prepared according to methods known in the art. Reaction of D-1 with alcohol D-2 under appropriate conditions (e.g., KOH/heat) yields ester D-3, which can then be coupled to amine D-4 to produce protected amine D-5. The protected amine D-5 can be coupled with the acid chloride D-6 using basic reagents (e.g., triethylamine/DMAP) to yield D-7 and deprotected using acid (e.g., TFA) to produce the de-protected amine D-8. The final coupling between D-8 and D-9 can proceed under basic conditions (e.g., DIPEA) to afford D-10, a compound of structure (II).

GENERAL REACTION SCHEME 5

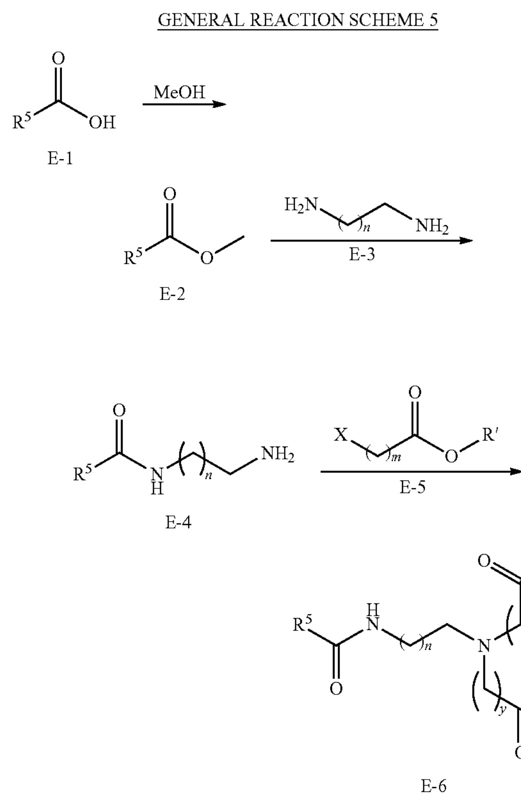

E-1 E-2 E-4 E-6

General Reaction Scheme 5 (“Method E”) provides an exemplary method for preparation of compounds of structure (II). $R^1$, $R^2$, $R^5$, y and z in General Reaction Scheme 2 are as defined herein. R', X, m and n refer to variables selected such that E-6 is a compound having a structure (I). For example, R' is $R^1$ or $R^2$, X is Br, m is y or z, and n is an integer ranging from 0 to 23. Compounds of structure E-1 are purchased or prepared according to methods known in the art. Reaction of E-1 with methanol to afford ester E-2 is carried out under appropriate conditions (e.g., acetyl chloride). Ester E-2 can be prepared by adding di-amine E-3 using, for example, methanol and heat. The resulting amide E-4 can be coupled to E-5 using basic conditions (e.g., DIPEA) to afford E-6, a compound of structure (II).

GENERAL REACTION SCHEME 6

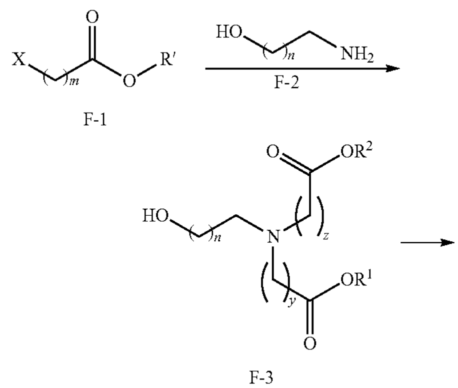

F-1 F-3

-continued

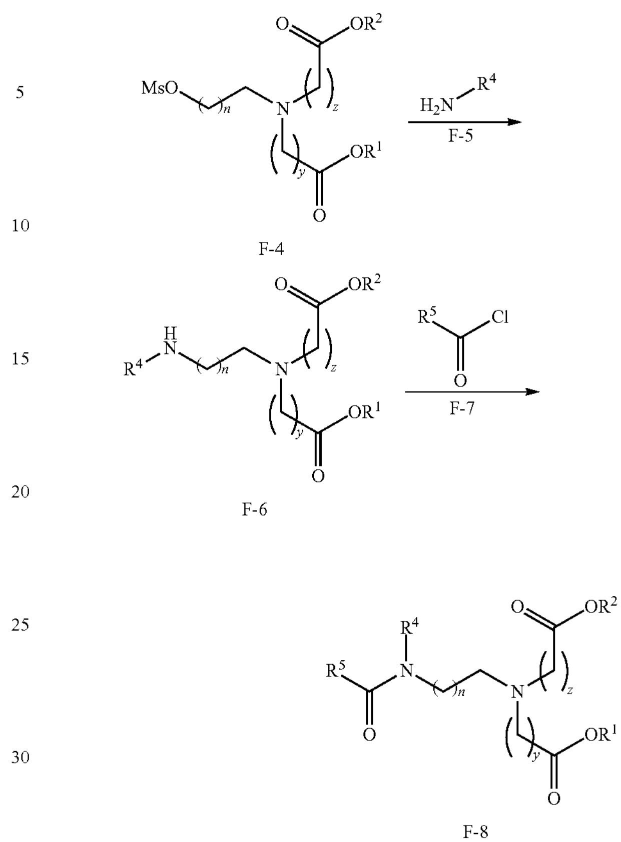

F-4 F-6 F-8

General Reaction Scheme 6 (“Method F”) provides an exemplary method for preparation of compounds of structure (II). $R^1$, $R^2$, $R^4$, $R^5$, y and z in General Reaction Scheme 3 are as defined herein. R', X, m and n refer to variables selected such that F-8 is a compound having a structure (I). For example, R' is $R^1$ or $R^2$, X is Br, m is y or z, and n is an integer ranging from 0 to 23. Compounds of structure F-1 are purchased or prepared according to methods known in the art. Reaction of F-1 alcohol/amine F-2 proceeds under appropriate conditions (e.g., $KCO_3$, $Ce_2CO_3$ and NaI) to yield di-ester/alcohol F-3. Mesylate F-4 is obtained (e.g., using MsCl, triethylamine and DMAP) and coupled with amine F-5 (e.g., using heat) to afford di-ester F-6. The final coupling between F-6 and acid chloride F-7 proceeds using basic coupling conditions (e.g., triethylamine, DMAP) to afford F-8, a compound of structure (II).

GENERAL REACTION SCHEME 7

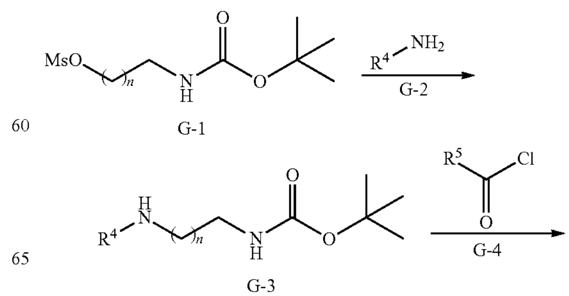

G-1 G-3

-continued

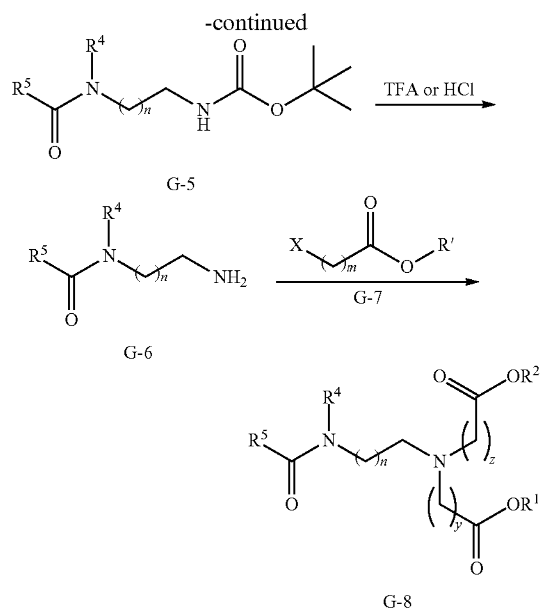

G-5

G-6

G-8

General Reaction Scheme 7 ("Method G") provides an exemplary method for preparation of compounds of structure (II). $R^1$, $R^2$, $R^4$, $R^5$, y and z in General Reaction Scheme 4 are as defined herein. $R^1$, X, m and n refer to variables selected such that G-8 is a compound having a structure (I). For example, R' is $R^1$ or $R^2$, X is Br, m is y or z, and n is an integer ranging from 0 to 23. Compounds of structure G-1 are purchased or prepared according to methods known in the art. Reaction of mesylate G-1 is coupled to amine G-2 (e.g., using heat to 75° C.) to yield protected amine G-3, which is reacted with acid chloride G-4 (e.g., using triethylamine/DMAP) to afford amide G-5. The protecting group is removed under acidic conditions (e.g., TFA) and amine G-6 is then coupled with G-7 under basic conditions (e.g., DIPEA) to afford G-8, a compound of structure (II).

It should be noted that various alternative strategies for preparation of compounds of structure (I) or (II) are available to those of ordinary skill in the art. The use of protecting groups as needed and other modification to the above General Reaction Schemes 1-7 will be readily apparent to one of ordinary skill in the art. The following examples are provided for purpose of illustration and not limitation.

Example 1

Luciferase mRNA In Vivo Evaluation Using Lipid Nanoparticle Compositions

A lipid of structure (I) or (II), DSPC, cholesterol and PEG-lipid were solubilized in ethanol at a molar ratio of 50:10:38.5:1.5 or 47.5:10:40.8:1.7. Lipid nanoparticles (LNP) were prepared at a total lipid to mRNA weight ratio of approximately 10:1 to 30:1. Briefly, the mRNA was diluted to 0.2 mg/mL in 10 to 50 mM citrate buffer, pH 4. Syringe pumps were used to mix the ethanolic lipid solution with the mRNA aqueous solution at a ratio of about 1:5 to 1:3 (vol/vol) with total flow rates above 15 mL/min. The ethanol was then removed and the external buffer replaced with PBS by dialysis. Finally, the lipid nanoparticles were filtered through a 0.2 μm pore sterile filter.

Studies were performed in 6-8 week old female C57BL/6 mice (Charles River) 8-10 week old CD-1 (Harlan) mice (Charles River) according to guidelines established by an institutional animal care committee (ACC) and the Canadian Council on Animal Care (CCAC). Varying doses of mRNA-lipid nanoparticle were systemically administered by tail vein injection and animals euthanized at a specific time point (e.g., 4 hours) post-administration. Liver and spleen were collected in pre-weighed tubes, weights determined, immediately snap frozen in liquid nitrogen and stored at −80° C. until processing for analysis.

For liver, approximately 50 mg was dissected for analyses in a 2 mL FastPrep tubes (MP Biomedicals, Solon OH). ¼" ceramic sphere (MP Biomedicals) was added to each tube and 500 μL of Glo Lysis Buffer—GLB (Promega, Madison WI) equilibrated to room temperature was added to liver tissue. Liver tissues were homogenized with the FastPrep24 instrument (MP Biomedicals) at 2×6.0 m/s for 15 seconds. Homogenate was incubated at room temperature for 5 minutes prior to a 1:4 dilution in GLB and assessed using SteadyGlo Luciferase assay system (Promega). Specifically, 50 μL of diluted tissue homogenate was reacted with 50 μL of SteadyGlo substrate, shaken for 10 seconds followed by 5 minute incubation and then quantitated using a CentroXS$^3$ LB 960 luminometer (Berthold Technologies, Germany). The amount of protein assayed was determined by using the BCA protein assay kit (Pierce, Rockford, IL). Relative luminescence units (RLU) were then normalized to total μg protein assayed. To convert RLU to ng luciferase a standard curve was generated with QuantiLum Recombinant Luciferase (Promega).

The FLuc mRNA (L-6107) from Trilink Biotechnologies will express a luciferase protein, originally isolated from the firefly, *Photinus pyralis*. FLuc is commonly used in mammalian cell culture to measure both gene expression and cell viability. It emits bioluminescence in the presence of the substrate, luciferin. This capped and polyadenylated mRNA is fully substituted with 5-methylcytidine and pseudouridine.

Example 2

Determination of $pK_A$ of Formulated Lipids

As described elsewhere, the pKa of formulated lipids is correlated with the effectiveness of LNPs for delivery of nucleic acids (see Jayaraman et al, Angewandte Chemie, International Edition (2012), 51(34), 8529-8533; Semple et al, Nature Biotechnology 28, 172-176 (2010)). The preferred range of pKa is ~5 to ~7. The $pK_a$ of each lipid was determined in lipid nanoparticles using an assay based on fluorescence of 2-(p-toluidino)-6-napthalene sulfonic acid (TNS). Lipid nanoparticles comprising novel lipid or structure (I) or (II)/DSPC/cholesterol/PEG-lipid (50/10/38.5/1.5 or 47.5:10:40.8:1.7 mol %) in PBS at a concentration of 0.4 mM total lipid are prepared using the in-line process as described in Example 1. TNS was prepared as a 100 μM stock solution in distilled water. Vesicles were diluted to 24 μM lipid in 2 mL of buffered solutions containing 10 mM HEPES, 10 mM IVIES, 10 mM ammonium acetate, and 130 mM NaCl, where the pH ranged from 2.5 to 11. An aliquot of the TNS solution was added to give a final concentration of 1 μM and following vortex mixing fluorescence intensity was measured at room temperature in a SLM Aminco Series 2 Luminescence Spectrophotometer using excitation and emission wavelengths of 321 nm and 445 nm. A sigmoidal best fit analysis was applied to the fluorescence data and the $pK_a$ was measured as the pH giving rise to half-maximal fluorescence intensity.

Lipid nanoparticle particle size was approximately 55-95 nm diameter, and in some instances approximately70-90 nm diameter as determined by quasi-elastic light scattering using a Malvern Zetasizer Nano ZS (Malvern, UK). The diameters given are intensity weighted means. Encapsulation was determined using a fluorescent intercalating dye based assay (Ribogreen).

Tables 3 and 4 provide properties of representative compounds of structure (I) and (II), respectively, which were formulated using the following molar ratio: 47.5% cationic lipid/10% distearoylphosphatidylcholine (DSPC)/40.8% Cholesterol/1.7% PEG lipid ("PEG-DMA" 2-[2-(ω-methoxy(polyethyleneglycol$_{2000}$)ethoxy]-N,N-ditetradecylacetamide). Relative activity was determined by measuring luciferase expression in the liver 4 hours following administration via tail vein injection as described in Example 1. The activity was compared at a dose of 0.3 and 1.0 mg mRNA/kg and expressed as ng luciferase/g liver measured 4 hours after administration, as described in Example 1.

TABLE 3

Properties of Representative Compounds of Structure (I)

| No. | pK$_a$ | Liver Luc @ 0.3 mg/kg (ng luc/g liver) | Liver Luc @ 1.0 mg/kg (ng luc/g liver) | Structure |
|---|---|---|---|---|
| I-2 | 5.57 | Not determined | Not determined | 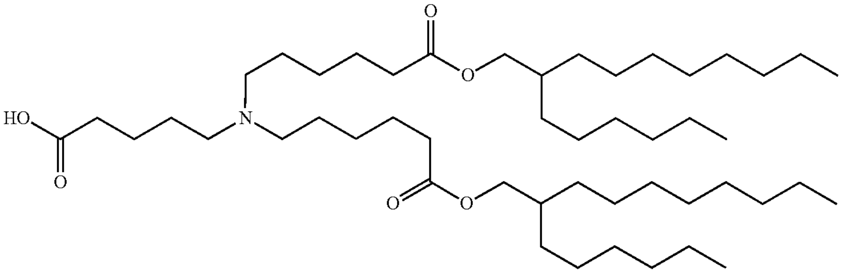 [SMILES: CCCCCCCCC(CCCCCC)COC(=O)CCCCCN(CCCCCC(=O)OCC(CCCCCC)CCCCCCCC)CCCCC(=O)O] |
| I-3 | 5.99 | 139 ± 43 | 1711 ± 507 | 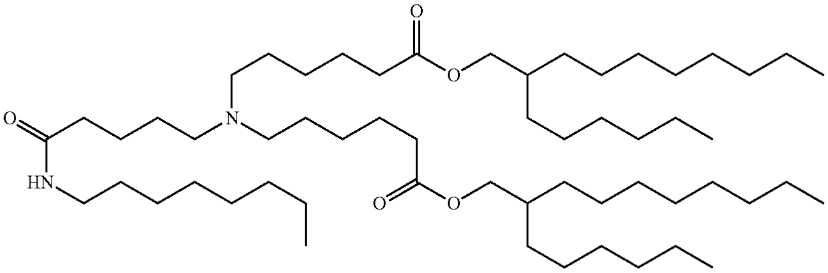 [SMILES: CCCCCCCCNC(=O)CCCCN(CCCCCC(=O)OCC(CCCCCC)CCCCCCCC)CCCCCC(=O)OCC(CCCCCC)CCCCCCCC] |
| I-6 | 6.32 | 580 ± 209 | 3290 ± 582 | 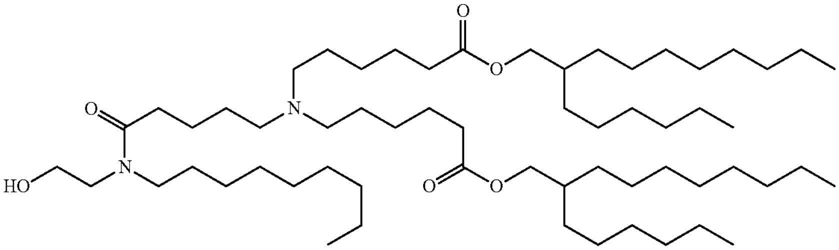 [SMILES: CCCCCCCCCN(CCO)C(=O)CCCCN(CCCCCC(=O)OCC(CCCCCC)CCCCCCCC)CCCCCC(=O)OCC(CCCCCC)CCCCCCCC] |
| I-11 | 5.89 | 228 ± 101 | 910 ± 454 | 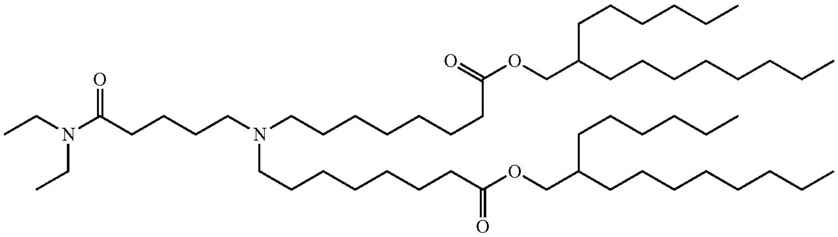 [SMILES: CCCCCCCCC(CCCCCC)COC(=O)CCCCCCCN(CCCCCCCC(=O)OCC(CCCCCC)CCCCCCCC)CCCCC(=O)N(CC)CC] |

TABLE 3-continued
| Properties of Representative Compounds of Structure (I) | | | | |
|---|---|---|---|---|
| No. | $pK_a$ | Liver Luc @ 0.3 mg/kg (ng luc/g liver) | Liver Luc @ 1.0 mg/kg (ng luc/g liver) | Structure |
| I-12 | 6.01 | 413 ± 143 | 4002 ± 1573 | 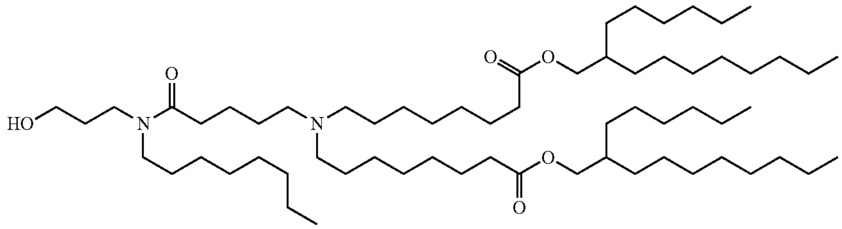 [SMILES: CCCCCCCCC(CCCCCC)COC(=O)CCCCCCCN(CCCCCCCC(=O)OCC(CCCCCC)CCCCCCCC)CCCCC(=O)N(CCCO)CCCCCCCC] |
TABLE 4
| Properties of Representative Compounds of Structure (II) | | | | |
|---|---|---|---|---|
| No. | $pK_a$ | Liver Luc @ 0.3 mg/kg (ng luc/g liver) | Liver Luc @ 1.0 mg/kg (ng luc/g liver) | Structure |
| II-4 | 5.95 | 150 ± 59 | 1405 ± 306 | 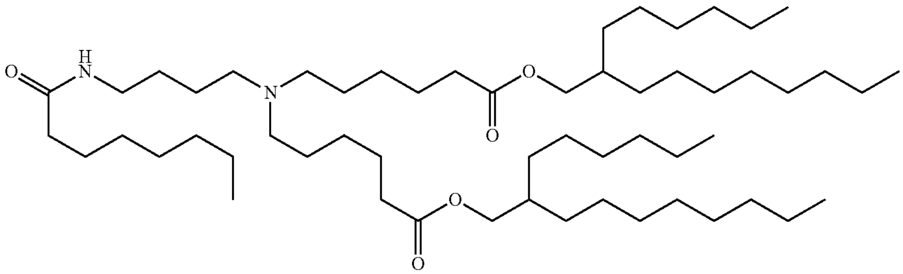 [SMILES: CCCCCCCCC(CCCCCC)COC(=O)CCCCCN(CCCCCC(=O)OCC(CCCCCC)CCCCCCCC)CCCCNC(=O)CCCCCCC] |
| II-5 | 6.80 | 146 ± 16 | 695 ± 278 | 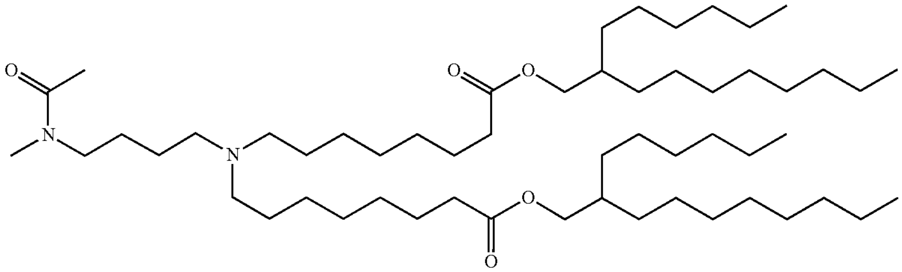 [SMILES: CCCCCCCCC(CCCCCC)COC(=O)CCCCCCCN(CCCCCCCC(=O)OCC(CCCCCC)CCCCCCCC)CCCCN(C)C(C)=O] |
| II-14 | 5.63 | 128 ± 17 | 827 ± 537 | 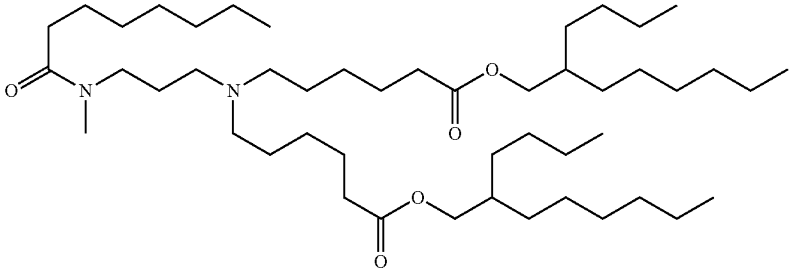 [SMILES: CCCCCCCC(=O)N(C)CCCN(CCCCCC(=O)OCC(CCCC)CCCCCC)CCCCCC(=O)OCC(CCCC)CCCCCC] |

TABLE 4-continued

| Properties of Representative Compounds of Structure (II) | | | | |
|---|---|---|---|---|
| No. | $pK_a$ | Liver Luc @ 0.3 mg/kg (ng luc/g liver) | Liver Luc @ 1.0 mg/kg (ng luc/g liver) | Structure |
| II-16 | 6.08 | 93 ± 38 | 1312 ± 569 | 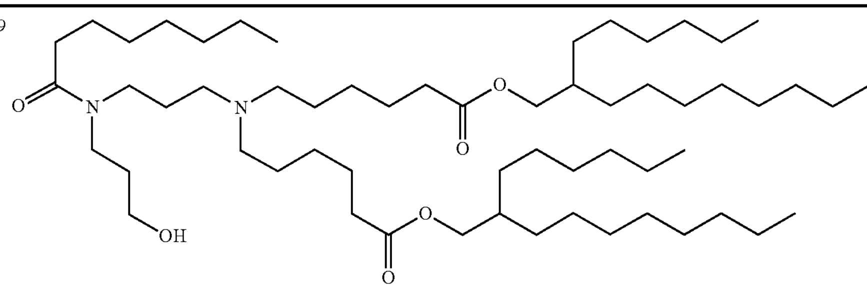 |

Example 3

Synthesis of Compound I-1

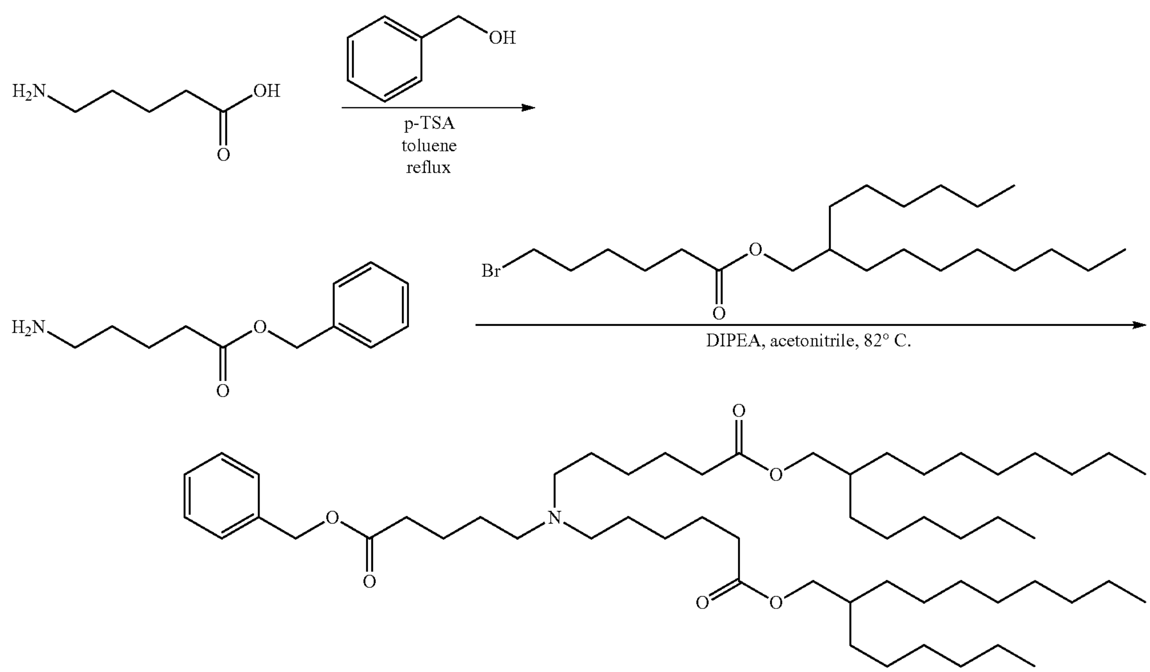

A mixture of 5-aminovaleric acid (1 eq. 2.5 g, 21.3 mmol), benzyl alcohol (3 eq, 64 mmol, 6.92 g, 6.63 mL), toluene (60 mL) and p-toluenesulfonic acid monohydrate (1.1 eq, 23.4 mmol, 4.45 g) was heated to reflux for 16 hours under Dean-Stark conditions. The reaction mixture was cooled to room temperature and filtered. The white solid was washed with toluene (40 mL) to afford the desired product as white solid is 6.06 g (16 mmol, 75%, sulfonic acid salt).

Compound I-1

A mixture of 2-hexyldecyl 6-bromohexanoate (1.6 eq, 6.31 mmol, 2.646 g), benzyl 5-aminopentanoate (1.5 g, 3.94 mmol), N,N-diisopropylethylamine (3.5 eq, 13.8 mmol, 1.78 g, 2.40 mL) and anhydrous acetonitrile (20 mL) was heated at 82° C. in an oil bath for 3 days in a sealed pressure flask. The reaction mixture was concentrated and the residue was taken up in a hexane (40 mL). The mixture was filtered through a pad of silica gel, and washed with a hexane/ethyl acetate gradient (1:0 to 49:1) until all unreacted 2-hexyldecyl 6-bromohexanoate was removed. Then the pad was washed with a mixture of hexane/ethyl acetate/triethylamine (400 mL, 4:1:0.1) and concentrated to yield the crude product as yellow oil (870 mg). The crude product was purified by flash column chromatography on silica gel (230-400 mesh silica gel, 40 g, gradient from 4 to 5% methanol in dichloromethane). The desired product was afforded as slightly yellow oil (704, 0.8 mmol, 25%).

$^1H$ NMR (400 MHz, $CDCl_3$) δ: 7.39-7.30 (m, 5H), 5.12 (s, 2H), 3.97 (d, 5.8 Hz, 4H), 2.41-2.33 (m, 8H), 2.30 (t, 7.5 Hz, 4H), 1.68-1.59 (m, 8H), 1.49-1.38 (m, 6H), 1.39-1.17 (m, 52H), 0.89 (t-like, 6.8 Hz, 12H).

Example 4

Synthesis of Compound I-2

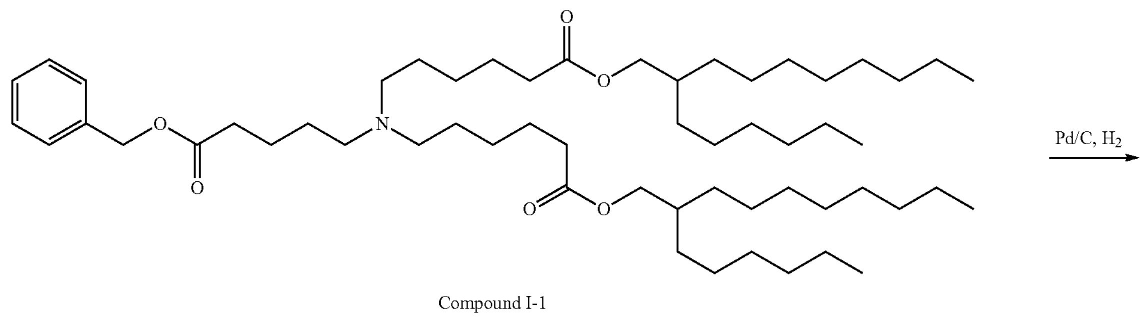

Compound I-1

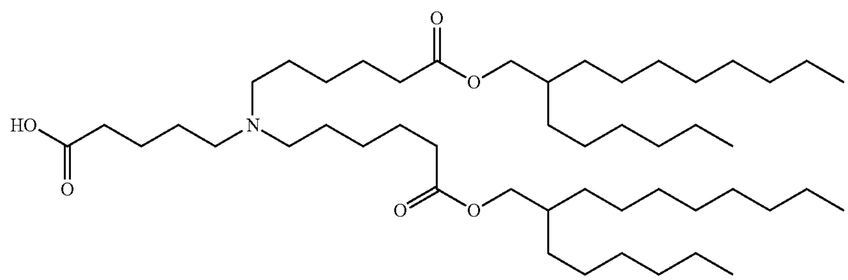

A solution of compound I-1 (640 mg, 0.72 mmol) containing 10% Pd/C (0.026 eq, 0.019 mmol, 20 mg) in ethanol/ethyl acetate (1:10 mL) was stirred under hydrogen for 16 hours. The reaction mixture was diluted with a mixture of hexane/ethyl acetate (98:2) and filtered through a pad of Celite. The filtrate was concentrated (>500 mg, slightly yellow oil). The resultant residue was purified by flash column chromatography on silica gel (gradient from 1% to 12.5% methanol in chloroform) to afford the desired product as colorless oil (403 mg, 0.51 mmol, 70%).

$^1H$ NMR (400 MHz, $CDCl_3$) δ: 3.97 (d, 5.8 Hz, 4H), 2.83-2.71 (m, 6H), 2.34-2.26 (m, 6H), 1.75-1.56 (m, 12H), 1.39-1.19 (m, 52H), 0.89 (t-like, 6.7 Hz, 12H).

Example 5

Synthesis of Compound I-3

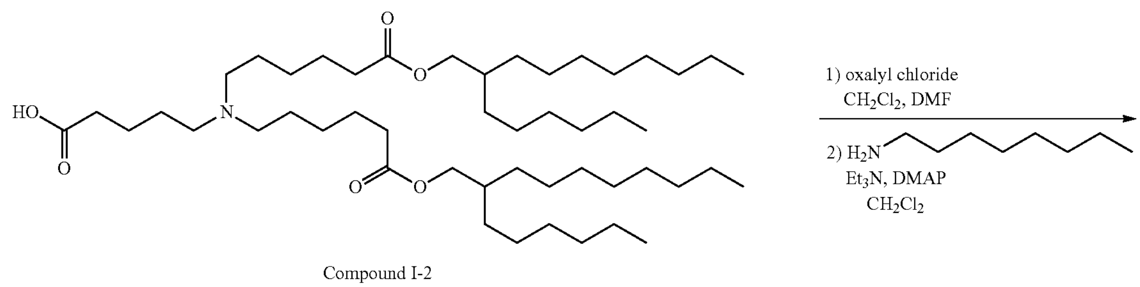

Compound I-2

-continued

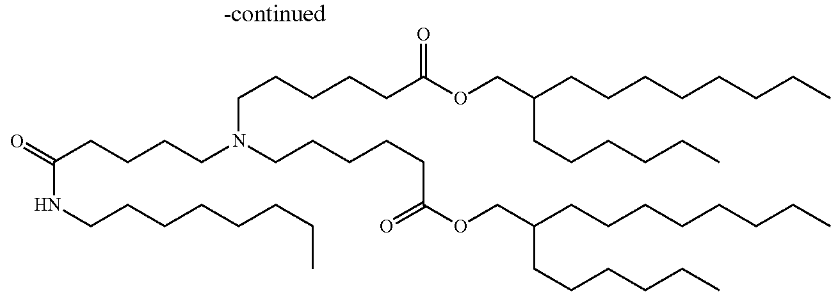

To a solution of compound I-2 (403 mg, 0.51 mmol) in dichloromethane (5 mL) and DMF (8 mg) was added via syringe oxalyl chloride (5 eq, 2.54 mmol, 322 mg, 221 μL) at room temperature under argon atmosphere. The mixture was stirred at room temperature for 2 hours. The mixture was concentrated and the resulting residue was taken up in dichloromethane (5 mL) and concentrated to dryness again. The residual yellow oil was dissolved in 8 mL of dichloromethane and half of it (4 mL) added via syringe to a solution of octylamine (0.5 mmol, 65 mg, 83 μL) and triethylamine (250 μL) and 4-dimethylaminopyridine (DMAP, 10 mg) in dichloromethane (5 mL) at room temperature. After addition, the mixture was stirred at room temperature overnight. The mixture was concentrated and the residue was taken up in a mixture of hexane/ethyl acetate/triethylamine. The mixture was filtered through a pad of silica gel and the pad was washed with a mixture of hexane/ethyl acetate/triethylamine (100 mL 70:30:1). The filtrate and washing was combined and concentrated to yield yellow oil (210 mg). The crude product (210 mg) was purified by flash dry column chromatography on silica gel (gradient from 0 to 5% methanol in chloroform) to afford the desired product as colorless oil (178 mg, 0.20 mmol, 78%).

$^1$H NMR (400 MHz, $CDCl_3$) δ: 5.55 (broad, t-like, 1H), 3.97 (d, 5.8 Hz, 4H), 3.25-3.21 (m, 2H), 2.44-2.34 (m, 6H), 2.31 (t, 7.5 Hz, 4H), 2.18 (t, 7.5 Hz, 2H), 1.68-1.58 (m, 8H), 1.53-1.38 (m, 8H), 1.32-1.19 (62H), 0.91-0.87 (m, 15H).

Example 6

Synthesis of Compound I-6

Compound I-6 was prepared according to method A to yield 84 mg of colorless oil.

$^1$H NMR (400 MHz, $CDCl_3$) δ: 3.97 (d, 5.8 Hz, 4H), 3.77 (t-like, 4.9 Hz, 2H), 3.73-3.61 (br. 1H), 3.53, 3.45 (sets of triplet-like, 4.8 Hz, 5.5 Hz, ratio 1.5/0.5, 2H), 3.34, 3.29 (two sets of triplet-like, 7.7 Hz, 7.7 Hz, ratio 0.5/1.5, 2H), 3.09-3.83 (br, 2H), 2.57-2.34 (br, 6H), 2.32 (t, 7.4 Hz, 4H), 1.95-1.51 (br, 12H), 1.51-1.38 (br, 4H), 1.38-1.08 (64H), 0.91-0.86 (m, 15H).

Example 7

Synthesis Compound I-7

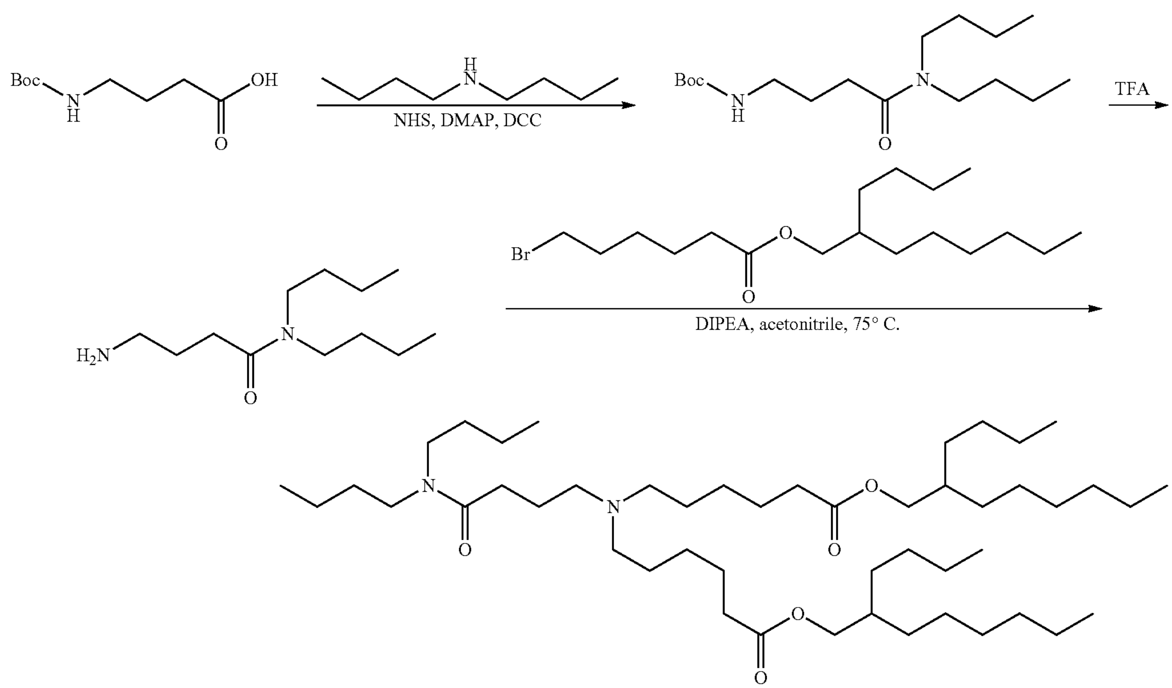

Compound I-7 was prepared according to method B as follows:

Synthesis of tert-Butyl (4-(dibutylamino)-4-oxobutyl)carbamate

To a solution of 4-((tert-butoxycarbonyl)amino)butyric acid (1.0 eq, 2 mmol, 406 mg), N-hydroxysuccinimide (1.0 eq, 2 mmol, 230 mg) and DMAP (20 mg) in 20 mL of dichloromethane was added N,N'-Dicyclohexylcarbodiimide (DCC, 1.2 eq, 2.4 mmol, 494 mg) and the mixture stirred at room temperature for 1 hour. The reaction mixture was filtered. To the filtrate was added dibutylamine (1.5 eq, 3 mmol, 387 mg, 504 μL). After 8 hours of stirring at room temperature, the mixture was filtered and diluted with dichloromethane and washed with dilute ammonium chloride solution (pH 6-7) and saturated aqueous sodium bicarbonate. The organic layer was dried over sodium sulfate overnight at room temperature.

The extract was concentrated (0.8 g oil/solid) and the crude product was purified by flash column chromatography on silica gel (gradient from 10 to 35% ethyl acetate in hexane). The desired product was afforded as colorless oil (630 mg, 2 mmol, 100%).

Synthesis of 4-Amino-N,N-dibutylbutanamide

In a round-bottomed flask equipped with a stir bar and a rubber septum under an argon atmosphere was placed crude tert-butyl (4-(dibutylamino)-4-oxobutyl) carbamate (630 mg, 2 mmol) in dichloromethane (10 mL). Trifluoroacetic acid (TFA, 40 mmol, 3 mL, 4.56 g) was added at room temperature during stirring. The reaction mixture was stirred at room temperature for 16 hours.

The mixture was diluted with dichloromethane and saturated sodium bicarbonate was slowly added with stirring. Two phases were separated and the aqueous phase was extracted with dichloromethane (4×). Anhydrous sodium carbonate and brine were added to the aqueous phase. The aqueous phase was extracted further with dichloromethane (2×). The combined extracts were dried over anhydrous sodium carbonate and sodium sulfate, filtered and concentrated. The resultant residue was taken up in dichloromethane (4 mL), filtered through a pad of silica gel and washed with a mixture of chloroform/ethanol/water/ammonium hydroxide (40:24:1.5:1). The filtrate and washings were combined and concentrated to dryness (517 mg, 2.4 mmol) to yield brownish oil/solid. The residue was taken up in acetonitrile (15 mL) and filtered through cotton, washed with acetonitrile (5 mL×3). The filtrate was concentrated to dryness (467 mg, 2.17 mmol). The product was used in the following synthetic step without further purification.

Synthesis of Compound I-7

A solution of 2-butyloctyl 6-bromohexanoate (1.85 eq, 450 mg, 1.24 mmol), 4-amino-N,N-dibutylbutanamide (143 mg, 0.67 mmol), N,N-diisopropylethylamine (2.5 mmol, 323 mg, 0.435 mL) and anhydrous acetonitrile (15 mL) was heated at 75° C. in an oil bath for 16 hours in a sealed pressure flask. The reaction mixture was cooled and concentrated to yield brown oil/solid. The crude was taken up in a mixture of hexane/ethyl acetate/triethylamine (20 mL, ~85:15:1), filtered through a pad of silica gel, and washed with a mixture of hexane/ethyl acetate/triethylamine (100 mL, 4:1:0.1). The filtrate was concentrated and the crude product was afforded as yellow oil/solid, 400 mg. The crude product was purified again by flash dry column chromatography on silica gel (gradient from 0 to 4% methanol in chloroform, 0 to 4%) to afford the desired product as slightly yellow oil (213 mg, 0.27 mmol, 44%).

$^1H$ NMR (400 MHz, $CDCl_3$) δ: 3.97 (d, 5.8 Hz, 4H), 3.31 (t-like, 7.6 Hz, 2H), 3.22 (t-like, 7.8 Hz, 2H), 2.45-2.36 (m, 6H), 2.30 (t, 7.5 Hz, 6H), 1.76 (quintet, 7.2 Hz, 2H), 1.63 (quintet-like, 7.6 Hz, 6H), 1.56-1.47 (m, 4H), 1.47-1.36 (m, 4H), 1.36-1.20 (40H), 0.96 (t, 7.2 Hz, 3H), 0.93 (t, 7.2 Hz, 3H), 0.93-0.87 (m, 12H).

Example 8

Synthesis of Compound I-8

Compound I-8 was prepared according to method B (in a similar manner to compound 7) to yield 207 mg (0.25 mmol, 40%) of slightly yellow oil.

$^1H$ NMR (400 MHz, $CDCl_3$) δ: 3.97 (d, 5.8 Hz, 4H), 3.31 (t-like, 7.6 Hz, 2H), 3.22 (t-like, 7.8 Hz, 2H), 2.43 (t-like, 7.1 Hz, 2H), 2.37 (t-like, 7.5 Hz, 4H), 2.31 (t, 7.4 Hz, 2H), 2.30 (t, 7.5 Hz, 4H), 1.76 (quintet, 7.3 Hz, 2H), 1.66-1.57 (m, 6H), 1.56-1.46 (m, 4H), 1.45-1.36 (m, 4H), 1.36-1.20 (48H), 0.96 (t, 7.3 Hz, 3H), 0.93 (t, 7.2 Hz, 3H), 0.93-0.87 (m, 12H).

Example 9

Synthesis of Compound I-10

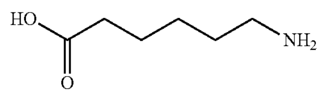

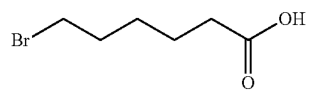

p-TSA
toluene
reflux

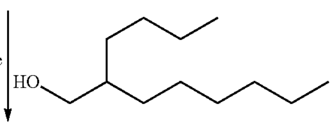

1) oxalyl chloride
$CH_2Cl_2$/DMF

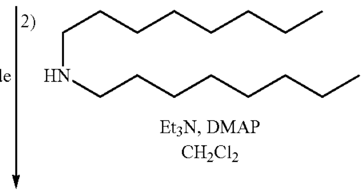

-continued

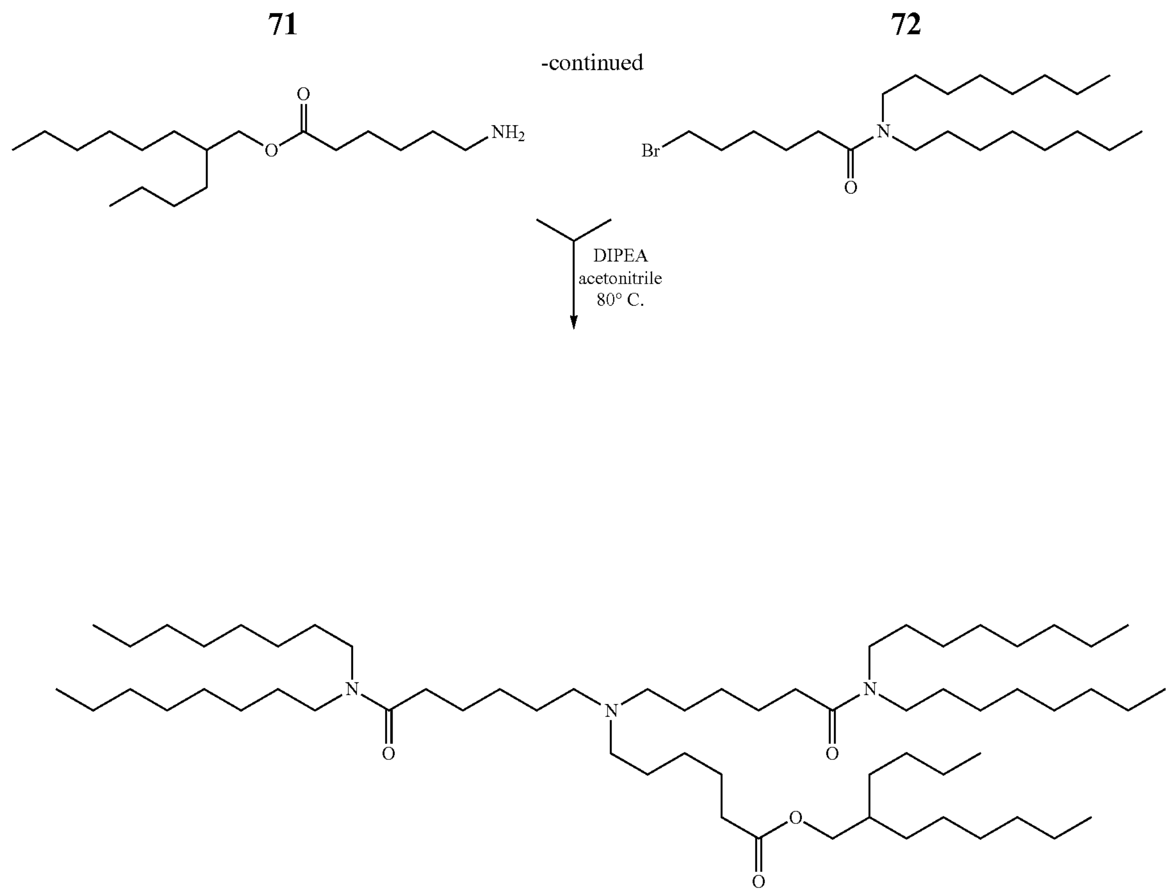

Compound I-10 was prepared according to method C as follows:

Synthesis of 2-Butyloctyl 6-aminohexanoate

A solution of 2-butyl-1-octanol (1.25 eq, 4.65 g, 25 mmol), 6-aminocaproic acid (2.62 g, 20 mmol), and p-toluenesulfonic acid monohydrate (1.1 eq, 22 mmol, 4.18 g) in toluene (70 mL) was heated to reflux for 16 hours under Dean-Stark conditions. The reaction mixture was allowed to cool. To reaction mixture was added saturated aqueous sodium bicarbonate solution until the pH of the aqueous layer was above 9. The two layers were separated and the organic layer was washed with brine and dried over anhydrous sodium sulfate.

Concentration of the filtered organic layer yielded cloudy oil. The crude product was taken up in a mixture of hexane/ethyl acetate (100 mL, 19:1) and filtered through a silica gel pad. The pad was washed with the mixture of hexane/ethyl acetate (200 mL) followed by washing with hexane/ethyl acetate/triethylamine (200 mL, ~80:20:1). Finally the pad was washed with a mixture of dichloromethane/methanol/ammonium hydroxide (400 mL, 95:5:0.13). The final washing was concentrated to dryness and the desired product was afforded as colorless oil (7.19 g) which contained about 1.2 g of p-TSA and was used without further purification.

Synthesis of 6-Bromo-N,N-dioctylhexanamide

To a solution of 6-bromohexanoic acid (2.93 g, 15 mmol) in dichloromethane (25 mL) and DMF (0.1 mL) was added oxalyl chloride (3 eq, 45 mmol, 5.7 g, 3.93 mL) at room temperature under argon atmosphere. The resulting mixture was stirred at room temperature overnight. The mixture was concentrated under reduced pressure for about 2 hours. The residual liquid/solid (yellow) was dissolved in 20 mL of dichloromethane and added to a solution of dioctylamine (1.1 eq, 16.5 mmol, 3.98 g, 4.98 mL), triethylamine (90 mmol, 9.09 g, 12.5 mL) and DMAP (10 mg) in dichloromethane (20 mL) at room temperature. The resulting mixture was concentrated after stirring for 2.5 hours. The concentrated yellow oil/solid was taken up in a mixture of hexane and ethyl acetate (~75:25) and 1M hydrochloric acid was added. The mixture was filtered and two layers were separated. The aqueous layer was extracted with dichloromethane (×3) and the combined extracts were dried over anhydrous sodium sulfate and concentrated to afford the crude product as yellow oil. The crude oil was purified by flash dry column chromatography on silica gel (gradient from 1:0 to 4:1, hexane/ethyl acetate). The desired was afforded as slightly yellow oil (5.09 g, 12.2 mmol, 81%).

Synthesis of Compound I-10

To 2-butyloctyl 6-aminohexanoate (0.76 mmol, 228 mg) was added 6-bromo-N,N-dioctylhexanamide (1.89 eq, 1.44 mmol, 603 mg), followed by anhydrous acetonitrile (15 mL) and N,N-diisopropylethylamine (3.2 eq, 2.4 mmol, 310 mg, 0.417 mL). The mixture was heated at 80° C. using a hot oil bath for 16 hours in a sealed pressure flask. The mixture was allowed to cool and concentrated. The resultant residue was purified by flash column chromatography on silica gel (40 g silica gel, gradient from 0 to 5% methanol in chloroform) to afford the desired product as colorless oil (198 mg, 0.20 mmol, 28%).

Example 10
Synthesis of Compound I-12
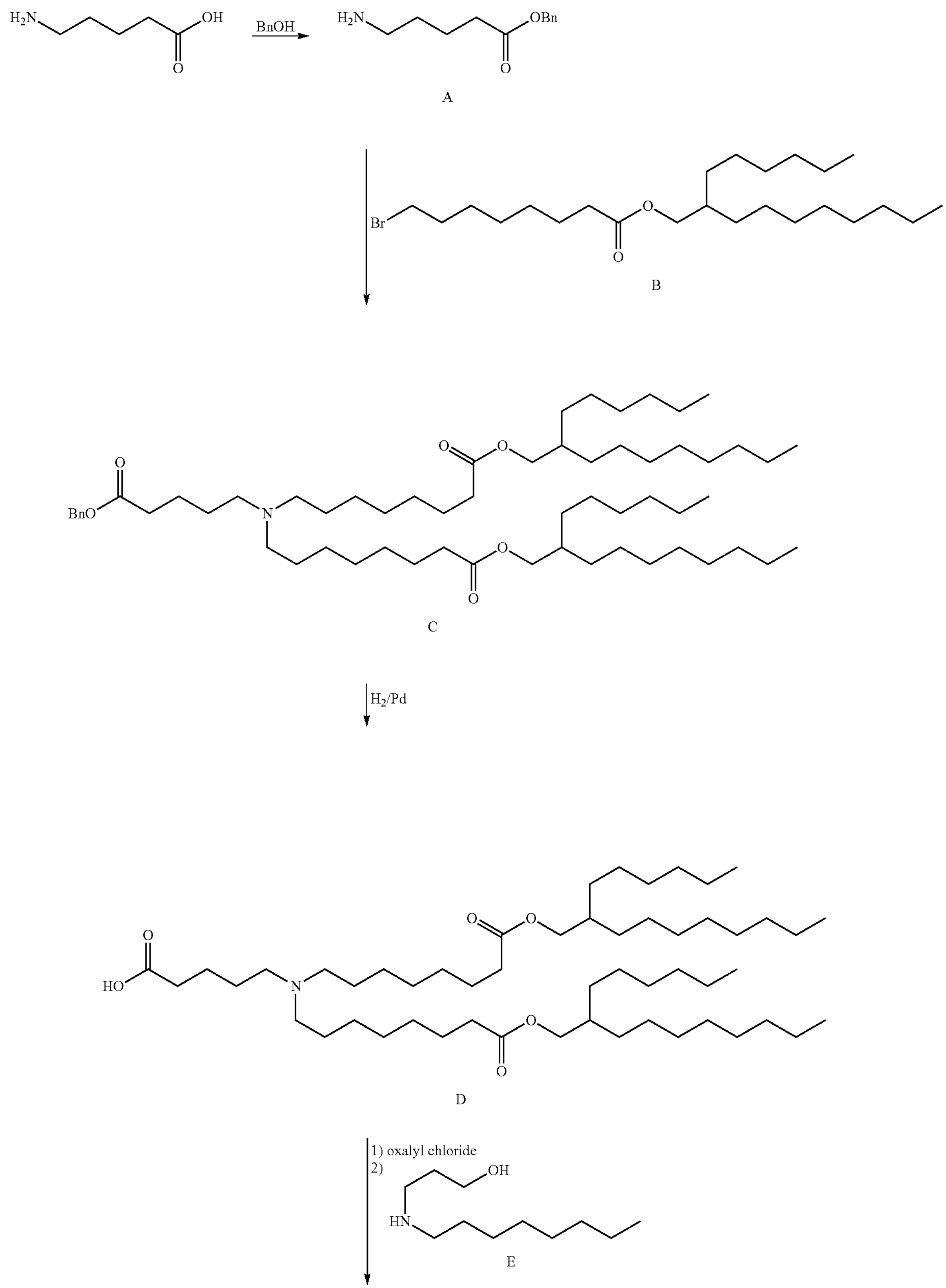

-continued

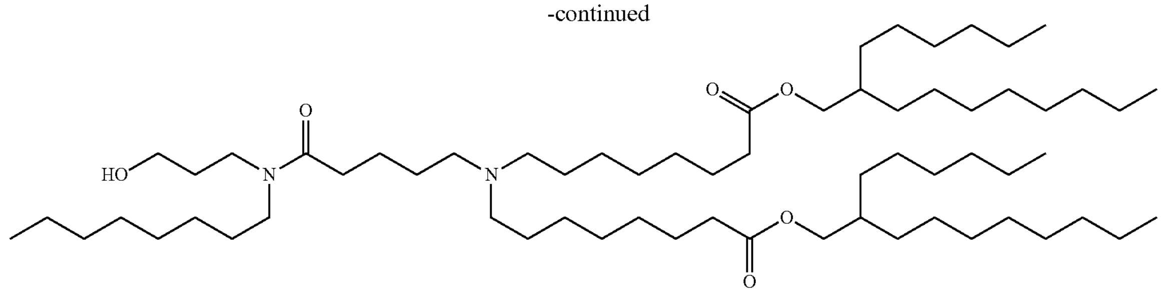

I-12

Compound I-12 was prepared as follows:

Synthesis of A

A mixture of 5-aminovaleric acid (1 eq. 2.9 g, 24.8 mmol), benzyl alcohol (2.3 eq, 58 mmol, 6.26 g, 6 mL), toluene (70 mL) and p-toluenesulfonic acid monohydrate (1.1 eq, 23.4 mmol, 4.45 g) was heated to reflux for 20 hours under Dean-Stark conditions. The mixture was cooled to RT. The solid was collected by filtration and was washed with toluene (20 mL×2) and diethyl ether (20 mL). The desired product (as t-TsOH salt) was obtained as a white solid (7.503 g, 19.8 mmol, 80%).

Synthesis of C

A mixture of A (1 eq, 5.59 mmol, 2.5 g), B (salt form, 1.4 eq., 3 g, 7.9 mmol, MW 379.47), N,N-diisopropylethylamine (3.5 equiv., 27.67 mmol, 3.58 g, 4.82 mL) and anhydrous acetonitrile (20 mL) was heated for 16 h in a sealed pressure flask (oil bath 83 C). The crude product was purified by column chromatography on silica gel (hexane-EtOAc-Et3N, from 95:5:0 to 75:25:1). This gave the desired product C as a yellow oil, 912 mg, 0.97 mmol, 35%).

Synthesis of D

To a solution of C (912 mg, 0.97 mmol) in EtOH-EtOAc (1:10 mL) was added 10% Pd/C (25 mg), and the mixture was stirred under hydrogen for 16 h. The reaction mixture was filtered through a pad of Celite© and washed with ethyl acetate (100 mL). The filtrate was concentrated to give the crude product as a slightly yellow oil (902 mg). The crude product was purified by column chromatography on silica gel (0 to 10% methanol in chloroform). This gave the desired product D as a pale wax (492 mg, 0.58 mmol, 60%).

Synthesis of 1-12

To a solution of D (492 mg, 0.58 mmol) in DCM (5 mL) and DMF (8 mg) was added oxalyl chloride (3.2 mmol, 406 mg) at RT under Ar. This mixture was stirred at RT overnight and concentrated. The residue was taken up in DCM (5 mL) and concentrated again to remove any oxalyl chloride. The residual oil (viscous yellow oil) was dissolved in 10 mL of DCM was added via syringe to a solution of E (1.9 mmol, 356 mg) and triethylamine (750 uL) and DMAP (5 mg) in DCM (10 mL) at −15 C in 5 min. After addition, the mixture was allowed to rise to RT slowly and stirred overnight. After purification by column chromatography (0 to 5% methanol in chloroform), the desired compound 12 was obtained as a colorless oil (100 mg). $^1$HNMR (400 MHz, CDCl3) δ: 4.08 (t-like, 7.1 Hz, 1H), 3.97 (d, 5.8 Hz, 4H), 3.54-3.44 (m, 4H), 3.23-3.17 (m, 2H), 2.44-2.33 (m, 8H), 2.30 (t, 7.5 Hz, 4H), 1.71-1.55 (m, 12H), 1.52-1.36 (m, 6H), 1.36-1.08 (70H), 0.92-0.86 (m, 15H).

Example 11

Synthesis of Compound I-11

Compound I-11 was prepared in a similar manner to compound I-12 to yield 60 mg of colorless oil. 1HNMR (400 MHz, $CDCl_3$) δ: 3.97 (d, 5.8 Hz, 4H), 3.38 (q, 7.1 Hz, 2H), 3.21 (q, 7.1 Hz, 2H), 2.44-2.27 (m, 12H), 1.68-1.54 (m, 8H), 1.52-1.36 (m, 6H), 1.36-1.20 (56H), 1.18 (t, 7.1 Hz, 3H), 1.11 (t, 7.1 Hz, 3H), 0.89 (t-like, 6.8 Hz, 12H).

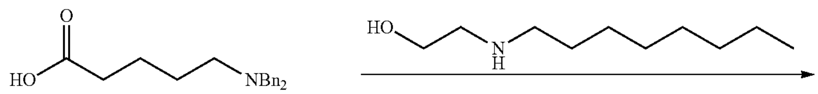

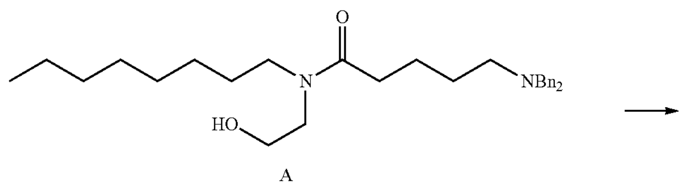

A

-continued

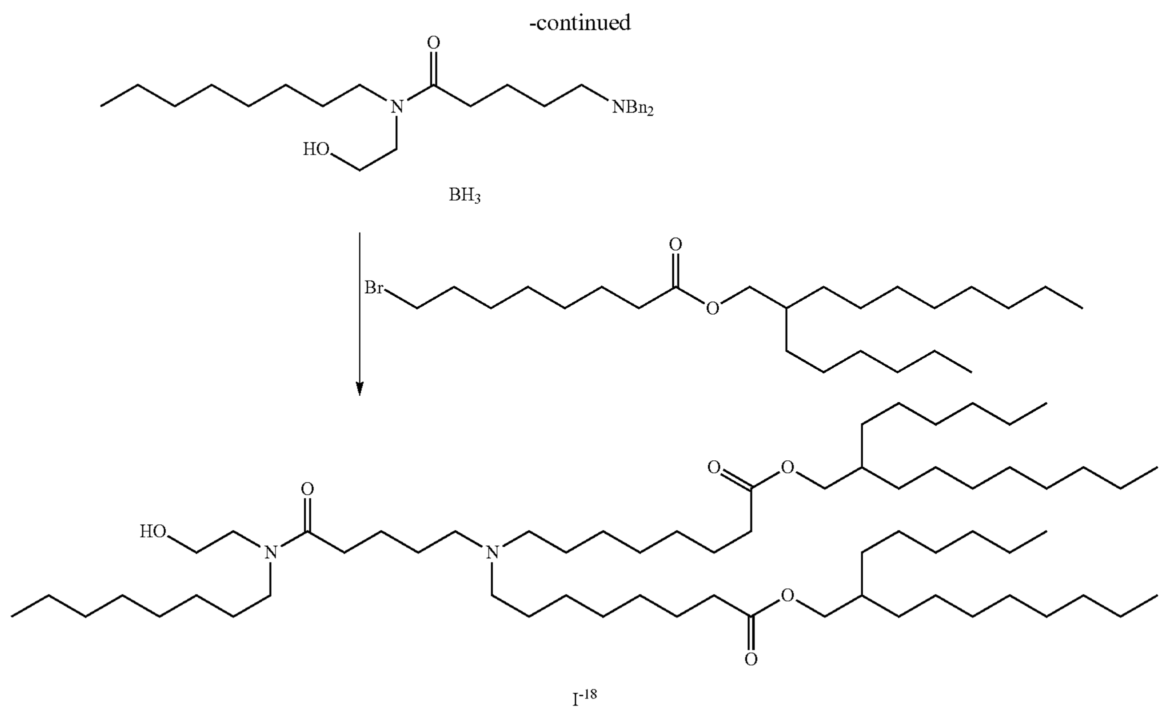

I-18

Example 12

Synthesis of Compound I-18

Synthesis of A

To a mixture of 5-(dibenzylamino)pentanoic acid (1.0 equiv, 1.32 g, 4.4 mmol, prepared from 5-aminovaleric acid and benzyl bromide), N-hydroxysuccinimide (1.0 equiv, 4.4 mmol, 506 mg, MW115.09) and 4-dimethylaminopyridine (4.4 mmol, 537 mg was added) in 20 mL of CH2Cl2 was added DCC (1 equiv, 4.4 mmol, 906 mg) and the mixture stirred at room temperature for 2.5 h. The mixture was filtered into a flask that contains 2-(octylamino)ethanol (1.5 equiv, 6.6 mmol, 1.14 g, prepared from 2-aminoethanol and octylamine). After 2 days of stirring at room temperature, the mixture was filtered and diluted with DCM and washed with dilute HCl solution (1M) and saturated aqueous NaHCO3. The organic layer was dried over Na2SO4. The extract was concentrated in vacuo (0.8 g oil/solid). The crude product was purified by column chromatography (a mixture of hexane, ethyl acetate and triethylamine, 90:10:0 to 60:40:1). This gave the desired product as colorless oil (pale oil, 0.98 g, 2.16 mmol, 49%).

Synthesis of B

A solution of A (0.98 g, 2.2 mmol) containing 10% Pd/C (100 mg) in methanol (20 mL) was stirred under hydrogen for 4 days. The mixture was filtered through a pad of Celite© and washed the methanol. The filtrate was concentrated (643 mg colorless oil). The product was used for the next step without further purification.

Synthesis of compound I-18

To B (0.7 mmol, 191 mg) was added 2-hexyldecyl 8-bromooctanoate (1.9 eq, 1.33 mmol, 558 mg, prepared from 8-bromooctanoic acid and 2-hexyl-1-decanol), followed by anhydrous acetonitrile (15 mL) and N,N-diisopropylethylamine (3 equiv., 2.1 mmol, 271 mg). The mixture was heated to for 16 h in a sealed pressure flask at 84 C. The mixture was cooled and concentrated. The crude product was purified by column chromatography (a mixture of chloroform and methanol, 100:0 to 95:5). This gave the desired product as slightly yellow oil (251 mg). $^1$HNMR (400 MHz, $CDCl_3$) δ:

Example 13

Synthesis of Compound I-19

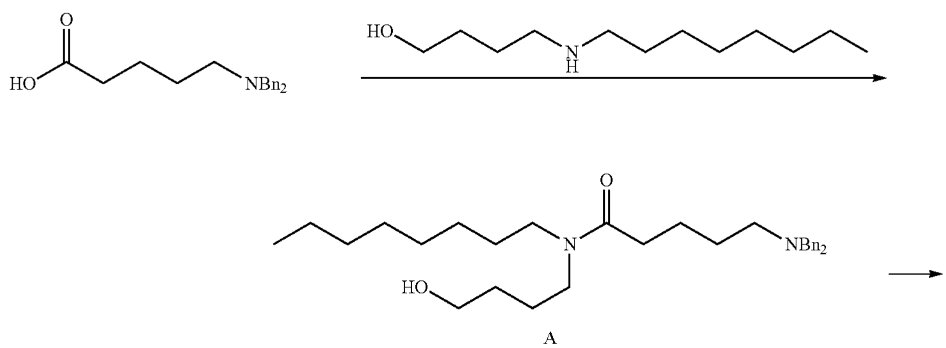

A

-continued

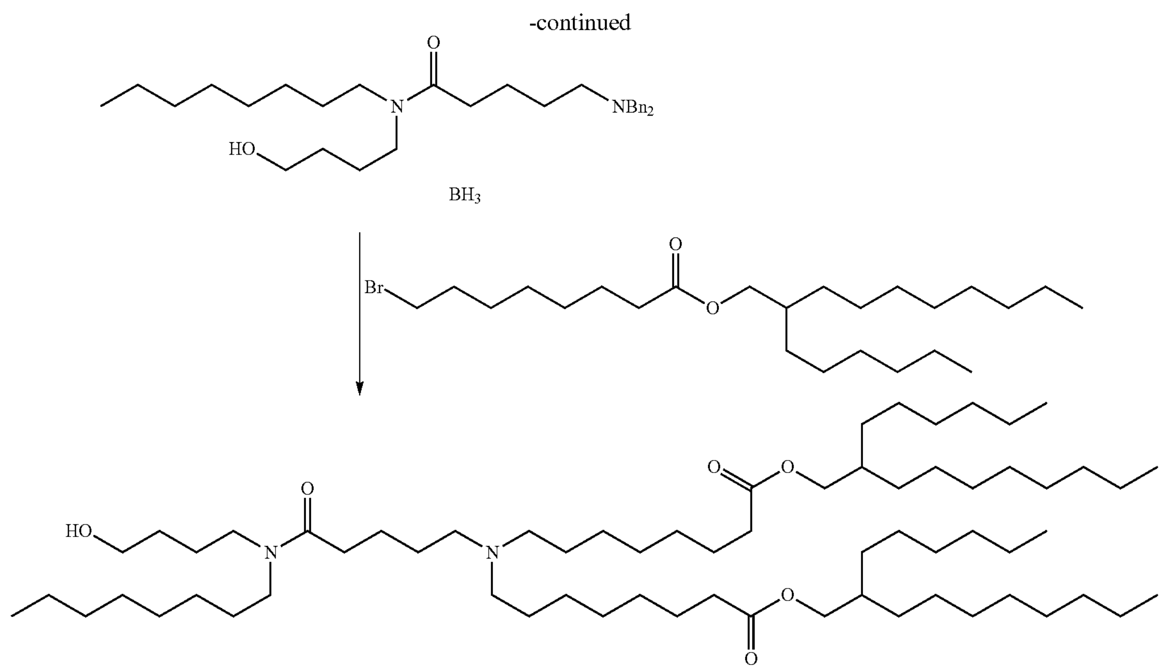

Synthesis of A

To a mixture of 5-(dibenzylamino)pentanoic acid (1.0 equiv, 1.32 g, 4.4 mmol, prepared from 5-aminovaleric acid and benzyl bromide), and 4-dimethylaminopyridine (4.4 mmol, 537 mg) in 20 mL of CH2Cl2 was added N-hydroxysuccinimide (1.0 equiv, 4.4 mmol, 506 mg), followed by addition of DCC (1 equiv, 4.4 mmol, 906 mg) and the mixture stirred at room temperature for 2.5 h. The reaction mixture was filtered into a flask that contains 4-(octylamino) butan-1-ol (2.0 g, prepared from γ-Butyrolactone and Octylamine in two steps). After 4 days of stirring at room temperature, the mixture was diluted with DCM and washed with dilute HCl solution (0.5 M, 100 mL) and saturated aqueous $NaHCO_3$. The organic layer was dried over Na2SO4. The extract was concentrated in vacuo (0.8 g oil/solid). The crude product was purified by column chromatography (a mixture of hexane, ethyl acetate and triethylamine, 90:10:0 to 60:40:1). This gave the desired product as colorless oil (pale oil, 0.554 g).

Synthesis of B

A solution of A (0.554 g, 1.15 mmol) containing 10% Pd/C (50 mg) in methanol (10 mL) was stirred under hydrogen for 2 days. The mixture was filtered through a pad of Celite© and washed the methanol. The filtrate was concentrated (mg colorless oil, mmol).

Synthesis of compound I-19

To B (180 mg, 0.6 mmol) was added 2-hexyldecyl 8-bromooctanoate (1.9 eq, 1.14 mmol, 509 mg), followed by anhydrous acetonitrile (15 mL) and N,N-diisopropylethylamine (3 equiv., 1.8 mmol, 233 mg). The mixture was heated to for 16 h in a sealed pressure flask at 84 C. The mixture was cooled and concentrated. The crude product was purified by column chromatography (a mixture of chloroform and methanol, 100:0 to 95:5). This gave the desired product as slightly yellow oil (117 mg).

Example 14

Synthesis of Compound II-3

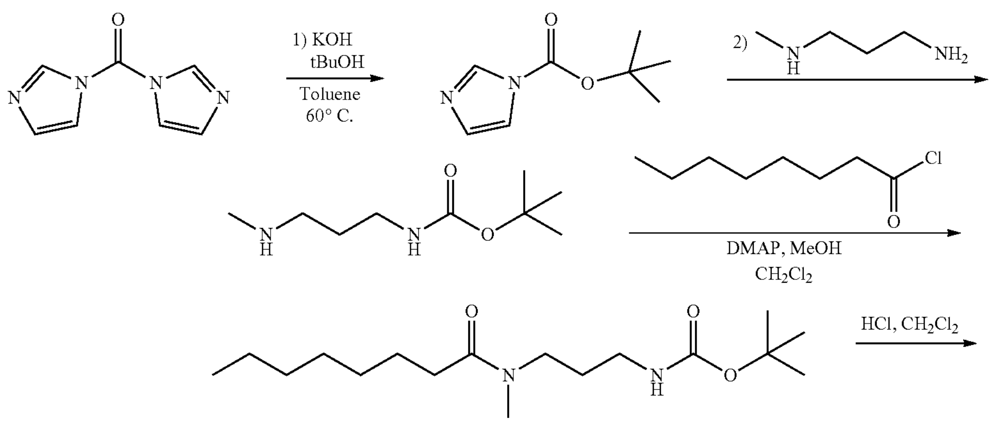

-continued

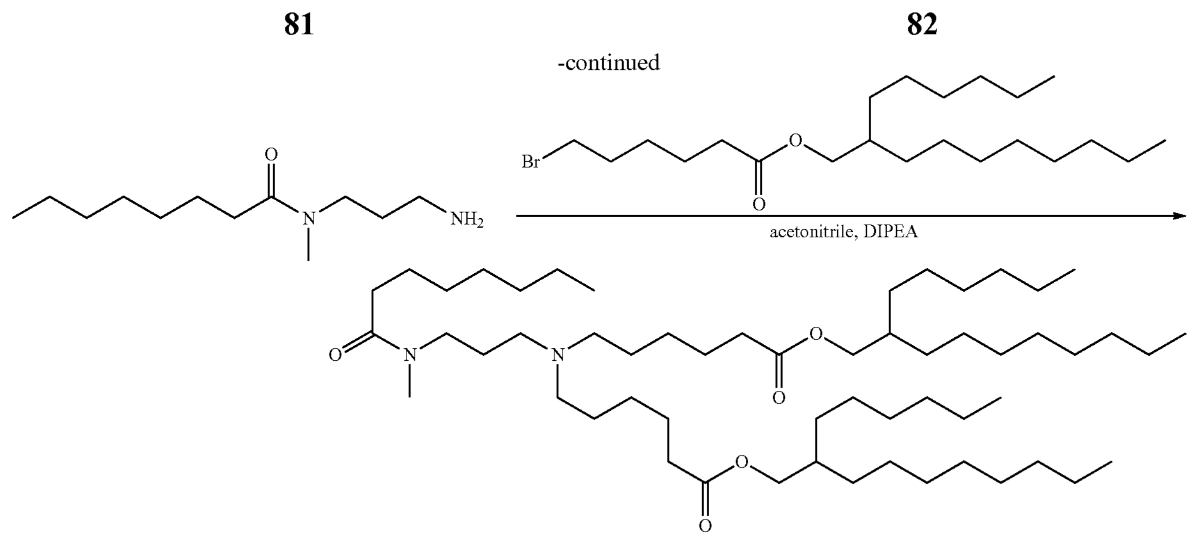

Compound II-3 was prepared according to method D as follows:

Synthesis of tert-Butyl (3-(methylamino)propyl)carbamate

A mixture of potassium hydroxide powder (20 mol %, 168 mg, 3 mmol), di(1H-imidazol-1-yl)methanone (2.43 g, 15 mmol,), and tert-butyl alcohol (15 mmol, 1.112 g) in dry toluene (76 mL) was heated at 60° C. (oil bath) with stirring for 3 hours under argon atmosphere. Then N-methyl-1,3-diaminopropane (15 mmol, 1.322 g, 1.566 mL) was added dropwise. The resulting mixture was heated at 60° C. for another 3 hours. After allowing the reaction mixture to cool to room temperature, water was added to the mixture. Two layers were separated and the organic layer was washed with brine, dried over sodium sulfate and concentrated to dryness, affording slightly yellow oil (0.966 g). The aqueous phase was extracted with dichloromethane (3×30 mL). The combined organic extracts were dried over sodium sulfate, filtered, and concentrated to afford slightly yellow oil (0.941 g). The two fractions were combined to afford 1.9 g of desired product (10 mmol, 67%). The product was used in the next synthetic step without further purification.

Synthesis of tert-Butyl (3-(N-methyloctanamido)propyl)carbamate

A solution of octanoyl chloride (1.3 eq, 2.08 mmol, 338 mg, 355 μL) in dichloromethane (10 mL) was added via syringe to a solution of compound tert-butyl (3-(methylamino)propyl)carbamate (1.6 mmol, 301 mg) and triethylamine (5 eq, 8 mmol, 810 mg, 1.11 mL) and DMAP (10 mg) in dichloromethane (15 mL) at room temperature over 5 minutes. The resulting mixture was stirred overnight at room temperature, followed by the addition of methanol (1 mL). The reaction mixture was left to stir for 1 hour. After stirring, the mixture was filtered through a pad of silica gel (3 cm width and 2 cm height) and washed with dichloromethane. The filtrate was diluted with dichloromethane and washed with water. The organic phase was separated and dried over sodium sulfate, filtered and concentrated to afford the desired product as yellow oil (460 mg, 1.46 mmol, 91%). The product was used in the next synthetic step without further purification.

Synthesis of N-(3-aminopropyl)-N-methyloctanamide

In a round-bottomed flask equipped with a stir bar and a rubber septum under an argon atmosphere was placed crude tert-butyl (3-(N-methyloctanamido)propyl)carbamate (1.46 mmol, 460 mg) in dichloromethane (10 mL). Trifluoroacetic acid (2.9 mL) was added at room temperature. The reaction mixture was stirred at room temperature for 3.5 hours, followed by the addition of 1.5 M hydrochloric acid (100 mL). The aqueous layer was extracted with dichloromethane (2×). The combined organic extracts were washed with 2 M hydrochloric acid (50 mL). The combined acid fractions were pooled and basified with concentrated aqueous sodium hydroxide (50% NaOH), and extracted with dichloromethane (3×). The combined organic layers were dried over sodium sulfate, filtered and concentrated. The desired product was afforded as colorless oil (160 mg, 0.75 mmol). The product was used in the next synthetic step without further purification.

Synthesis of Compound II-3

To N-(3-aminopropyl)-N-methyloctanamide (0.75 mmol, 160 mg) was added 2-hexyldecyl 6-bromohexanoate (1.9 eq, 1.43 mmol, 598 mg), followed by anhydrous acetonitrile (15 mL) and N,N-diisopropylethylamine (3 eq, 2.25 mmol, 290 mg, 0.391 mL). The mixture was heated to 80° C. using an oil bath for 2 days in a sealed pressure flask. The reaction mixture was concentrated, and the residue was taken up in a mixture of hexane/ethyl acetate (ca 5:1, 100 mL), washed with water, brine, dried over sodium sulfate, filtered and concentrated. The crude product was afforded as slightly yellow oil (~0.6 g). The crude product was diluted in hexane (10 mL) and filtered through a pad of silica gel. The pad was washed with a mixture of hexane/ethyl acetate/triethylamine (200 mL, 4:1:0.1). Concentration of the filtrate afforded the crude product as slightly yellow oil. The crude product was purified by flash column chromatography on silica gel (40 g of silica gel; gradient from 0 to 6% methanol in chloroform) to afford the desired product as colorless oil (216 mg, 0.24 mmol, 34%).

$^1$H NMR (400 MHz, $CDCl_3$) δ: 3.97 (dd, 5.8 Hz, 1.2 Hz, 4H), 3.37 (t-like, 7.5 Hz, 1H), 3.30 (t-like, 7.5 Hz, 1H), 2.98 (s, 1.5H), 2.91 (s, 1.5H), 2.41-2.35 (m, 6H), 2.34-2.26 (m, 6H), 1.71-1.58 (m, 10H), 1.48-1.38 (m, 4H), 1.37-1.18 (m, 60H), 0.92-0.86 (m, 15H).

Example 15

Synthesis of Compound II-4

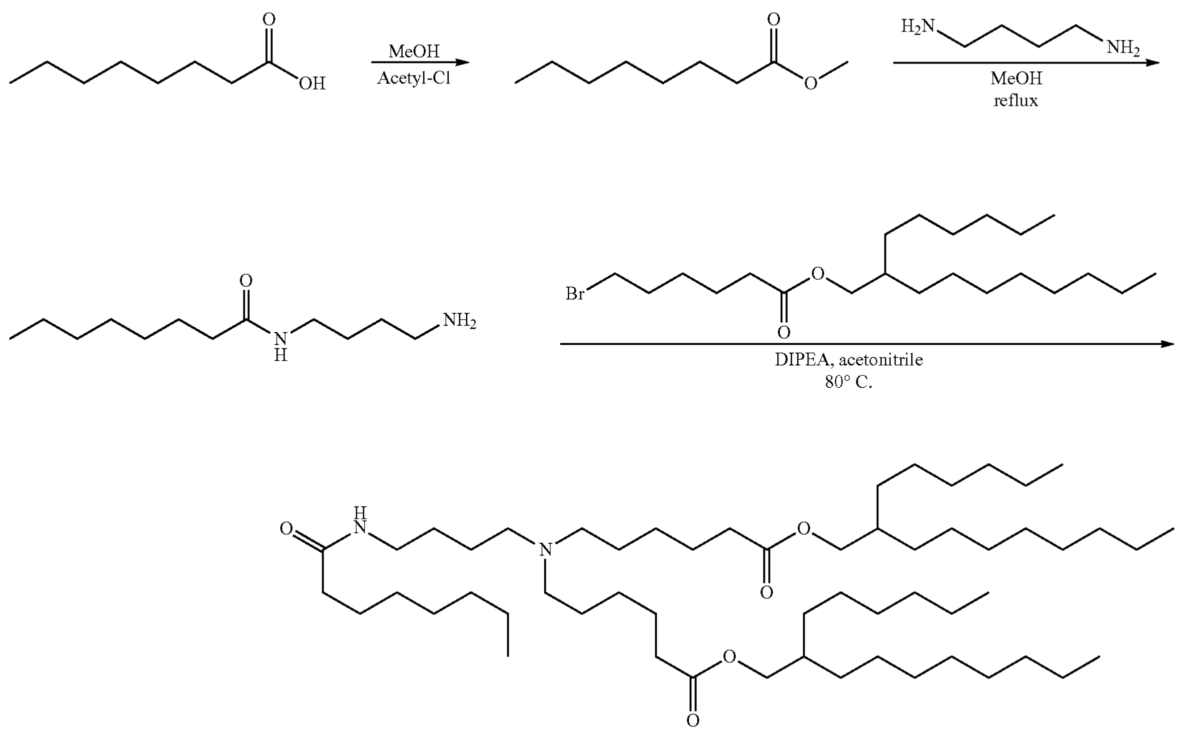

Compound II-4 was prepared according to method E as follows:

Synthesis of Methyl Octanoate

To an ice-salt-cooled solution of octanoic acid (50 mmol, 7.21 g) in 200 mL of methanol was added slowly acetyl chloride (10 mL) under argon atmosphere. The resulting solution was stirred for 20 minutes before removing the cooling bath. The solution was stirred overnight at room temperature. Solvent was removed under reduced pressure at 32° C. (two layers). To the residue was added saturated aqueous sodium bicarbonate (100 mL) and hexanes (200 mL). The hexane extract was washed with brine (70 mL), dried over sodium sulfate, filtered and concentrated to afford colorless oil. The oil was dried on high vacuum line overnight (6.439 g, 40.7 mmol, 93%).

Synthesis of N-(4-aminobutyl)octanamide

To a solution of 1,4-butanediamine (5 eq, 100 mmol, 8.8 g) in 50 mL of methanol at reflux was slowly (over 15 minutes) added methyl octanoate (20 mmol, 3.16 g) in methanol (20 mL). The reaction mixture was maintained under reflux for 48 hours. The solvent was then evaporated under reduced pressure and the residue was taken up in a mixture of water (70 mL) and ethyl acetate (100 mL). The phases were separated and the aqueous layer was extracted with ethyl acetate (2×). The combined organic extracts were washed with water, brine, dried over sodium sulfate and filtered. Concentration afforded a mixture of oil and white solid. The crude residue was dissolved in a mixture of dichloromethane and methanol. The solution was filtered through a pad of silica gel (1.5 cm height×6.5 cm width) and washed with a mixture of 5% methanol in dichloromethane until thin layer chromatography analysis showed all di-acylated product was removed. The pad was then washed a mixture of chloroform/ethanol/water/ammonia (30/25/3/2, 225 mL). The filtrate containing the desired product was concentrated to dryness (white solid, 2.52 g, 11.8 mmol, 59%).

Synthesis of Compound II-4

To a suspension of 2-hexyldecyl 6-bromohexanoate (1.9 eq, 1.00 g, 2.38 mmol) in anhydrous acetonitrile (15 mL) was added N-(4-aminobutyl)octanamide (1.25 mmol, 269 mg) and N,N-diisopropylethylamine (2 eq, 2.5 mmol, 323 mg, 0.435 mL). The mixture was heated to 80° C. using an oil bath for 32 hours in a sealed pressure flask. The reaction mixture was concentrated and the residue was taken up in a mixture of hexane/ethyl acetate (~5:1, 100 mL), washed with water, brine, dried over sodium sulfate, filtered and concentrated. The crude product was afforded as slightly yellow oil (~1.2 g). The crude product was diluted in hexane (10 mL) filtered through a pad of silica gel and washed with a mixture of hexane/ethyl acetate (1:0 to 49:1) until all unreacted 2-hexyldecyl 6-bromohexanoate was removed. Then the pad was washed with a mixture of hexane/ethyl acetate/triethylamine (200 mL, 4:1:0.1) and concentrated to afford brownish oil (~650 mg). The crude product (650 mg) was purified by flash column chromatography on silica gel (230-400 mesh silica gel, 40 g, gradient from 0 to 6% methanol in chloroform). The desired product was obtained as colorless oil (438 mg, 0.49 mmol, 41%).

$^1$H NMR (400 MHz, $CDCl_3$) δ: 5.95 (t-like, not well resolved, 5.3 Hz, 1H, NH), 3.98 (d, 5.8 Hz, 4H), 3.25 (q-like, 6.3 Hz, 2H), 2.42-2.35 (m, 6H), 2.31 (t, 7.5 Hz, 4H), 2.15 (t-like, 7.7 Hz, 2H), 1.68-1.58 (m, 8H), 1.54-1.38 (m, 8H), 1.36-1.18 (m, 60H), 0.92-0.86 (m, 15H).

Example 16

Synthesis of Compound II-5

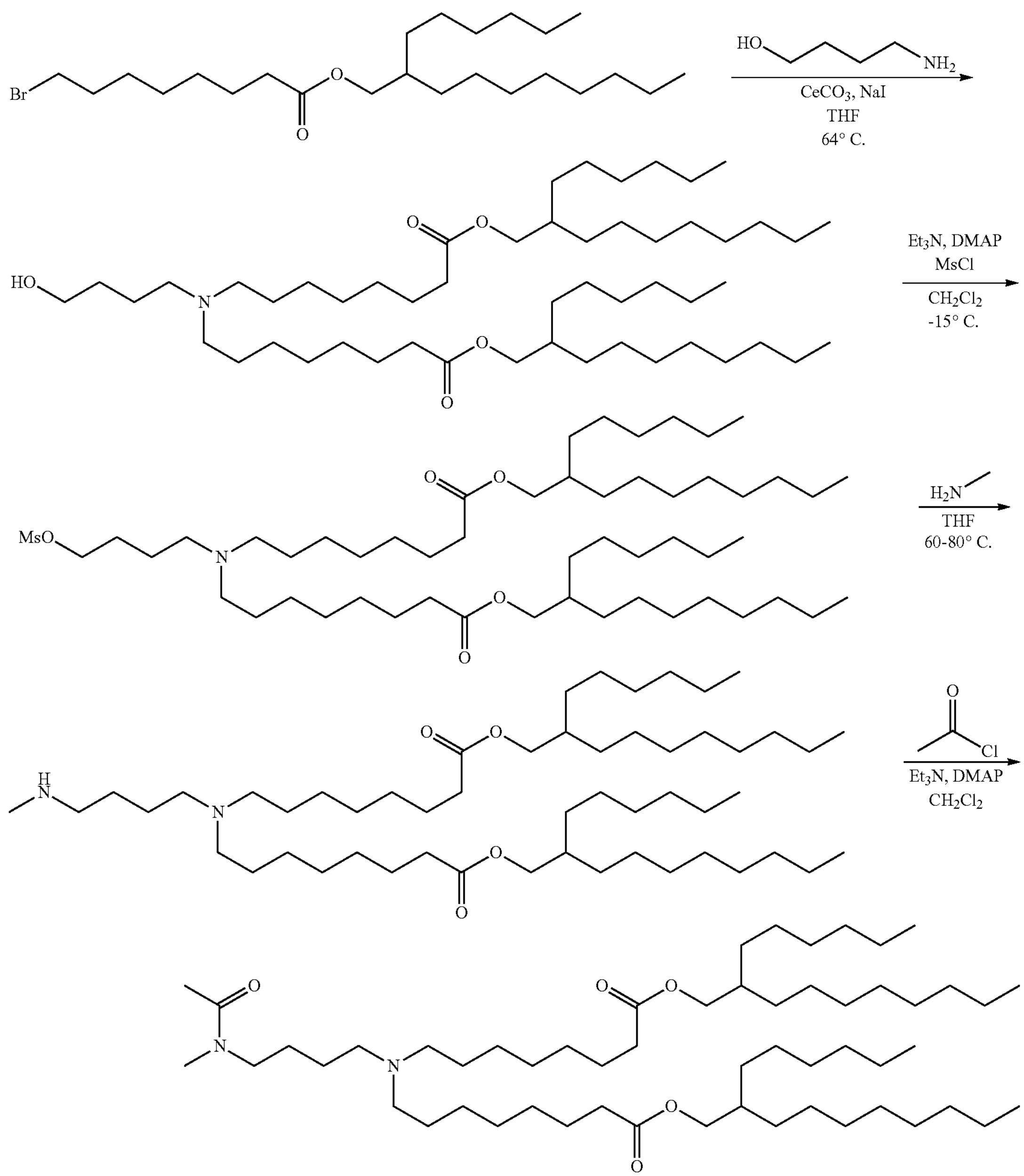

Compound II-5 was prepared according to method F as follows:

Synthesis of bis(2-Hexyldecyl) 8,8'((4-hydroxybutyl)azanediyl)dioctanoate

To a solution of 2-hexyldecyl 8-bromooctanoate (2 eq, 3.09 g, 6.9 mmol) in 30 mL of anhydrous tetrahydrofuran, were added 4-amino-1-butanol (1 eq, 3.45 mmol, 308 mg, 318 μL) potassium carbonate (2 eq, 6.9 mmol, 954 mg), cesium carbonate (0.3 eq, 1.04 mmol, 337 mg) and sodium iodide (10 mg). The mixture was heated to 64° C. using an oil bath in a pressure round-bottom flask under argon atmosphere for 6 days. The resultant crude product was dissolved in hexane (50 mL) and loaded on a short column of silica gel (1 cm height×6.5 cm width). The column was eluted with hexane (50 mL, fraction 1), a mixture of ethyl acetate/hexane (0 to 3% ethyl acetate). The unreacted 2-hexyldecyl 8-bromooctanoate (1.27 g, 2.84 mmol, 41%, colorless oil) was recovered. The column was eluted with a mixture of hexane/ethyl acetate/triethylamine (~4:1:0.1) to afford the crude product as slightly yellow oil (1.2 g). The crude product was further purified by flash dry column chromatography on silica gel (gradient from 0 to 4.2% methanol in chloroform) to afford the desired product (1.28 g, 1.56 mmol, 45%).

$^1$H NMR (400 MHz, $CDCl_3$) δ: 6.64-6.45 (br. s, 1H), 3.97 (d, 5.8 Hz, 4H), 3.62-3.51 (br. 2H), 3.07-2.34 (br. 6H), 2.30 (t, 7.5 Hz, 4H), 1.71-1.40 (m, 14H), 1.39-1.19 (m, 60H), 0.89 (t-like, 6.8 Hz, 12H).

Synthesis of bis(2-Hexyldecyl) 8,8'-((4-((methylsulfonyl)oxy)butyl)azanediyl)dioctanoate To a cooled (−15° C.) solution of bis(2-hexyldecyl) 8,8'-((4-hydroxybutyl)azanediyl)dioctanoate (542 mg, 0.66 mmol) in dichloromethane (15 mL) was added triethylamine (0.23 mL, 2.5 eq) and 4-dimethylaminopyridine (10 mg, 0.1 eq), followed by methanesulfonyl chloride (1.2 e., 0.79 mmol, 91 mg, 62 μL) in one portion. Upon completion of addition, the mixture was stirred at −15° C. for 30 minutes and at room temperature for 2 hours. The reaction mixture was then poured into a solution of saturated aqueous sodium bicarbonate. Two layers were separated and the aqueous layer was extracted with dichloromethane. The combined organic layers (100 mL) were washed with brine and dried over sodium sulfate. Triethylamine (2 mL) was added to the extracts, followed by filtration through a pad of silica gel (0.3 cm). The pad was washed with a mixture of dichloromethane/methanol/triethylamine (200 mL, ~85:15:1) followed by concentration to afford slightly yellow solid (~600 mg). The resultant solid was taken up in a mixture of hexane/ethyl acetate/triethylamine (80:20:1) and filtered to remove solids. The filtrate was concentrated and the desired product was afforded as yellow oil (501 mg, 0.55 mmol, 84%).

Synthesis of bis(2-Hexyldecyl) 8,8'-((4-(methylamino)butyl)azanediyl)dioctanoate The bis(2-hexyldecyl) 8,8'-((4-((methylsulfonyl)oxy)butyl)azanediyl)dioctanoate (501 mg, 0.55 mmol) was dissolved in a tetrahydrofuran solution of methylamine (2 M, 10 mL, 20 mmol). The resultant solution was stirred at 60-80° C. in a sealed pressure tube for 6 days. The mixture was concentrated under reduced pressure. The resultant residue was taken up in a mixture of dichloromethane and methanol (~85:15) and filtered through a pad of silica gel (0.5 cm) and concentrated to afford yellow oil (480 mg). The crude product was used in the next synthetic step without further purification.

Synthesis of Compound II-5

Acetyl chloride (1 mmol, 40 mg, 71 μL) in dichloromethane (10 mL) was added to a solution of bis(2-hexyldecyl) 8,8'-((4-((methylsulfonyl)oxy)butyl)azanediyl) dioctanoate (480 mg, ca 0.55 mmol) and triethylamine (350 μL) and DMAP (10 mg) in dichloromethane (10 mL) at room temperature over 10 minutes. After addition, the resulting mixture was stirred at room temperature overnight. The solvent was removed under reduced pressure and the residue was taken up in hexane and filtered through a pad of Celite. The filtrate was concentrated and the resultant residue (600 mg, yellow oil) was taken up hexane and filtered through a pad of silica gel. The pad was washed with ~0-3% ethyl acetate in hexane (discarded) followed by a mixture of hexane/ethyl acetate/triethylamine (100 mL, ~4:1:0.1). The filtrate was concentrated to afford slightly yellow oil (170 mg). The crude oil (170 mg) was purified by flash dry column chromatography on silica gel (gradient from 1 to 4% methanol in chloroform) to afford the desired product as colorless oil (46 mg).

$^1$H NMR (400 MHz, $CDCl_3$) δ: 3.97 (d, 5.8 Hz, 4H), 3.37 (t-like, 7.5 Hz, 1H), 3.27 (t-like, 7.5 Hz, 1H), 2.98 (s, 1.5H), 2.92 (s, 1.5H), 2.42-2.33 (m, 6H), 2.30 (t, 7.5 Hz, 4H), 2.10, 2.08 (two sets of singlet, 1:1, 3H), 1.68-1.57 (m, 8H), 1.45-1.36 (m, 6H), 1.35-1.21 (m, 60H), 0.89 (t-like, 6.8 Hz, 12H).

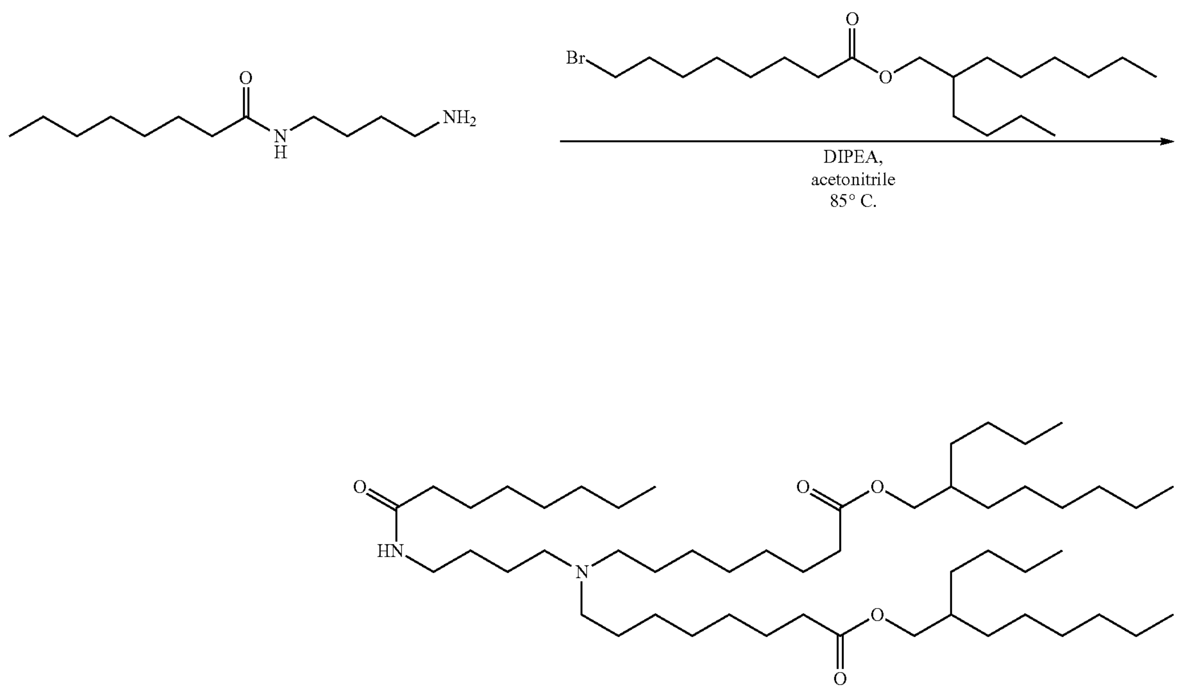

Example 17

Synthesis of Compound II-6

A mixture of 2-butyloctyl 8-bromooctanoate (1.6 eq, 783 mg, 2.0 mmol), N-(4-aminobutyl)octanamide (1.25 mmol, 269 mg), N,N-diisopropylethylamine (2 eq, 2.5 mmol, 323 mg) and anhydrous acetonitrile (15 mL) was heated to 85° C. using an oil bath for 16 hours in a sealed pressure flask. Following heating, the solvent was removed under reduced pressure. The resulting residue was taken up in a mixture of hexane/ethyl acetate (~49:1, 150 mL), washed with dilute aqueous ammonium chloride (pH 6-7), brine, dried over sodium sulfate, filtered and concentrated to afford brown viscous oil. The crude product was purified by column chromatography on silica gel (gradient from 0% to 5% methanol in chloroform) to afford the desired product as colorless oil (320 mg, 0.38 mmol, 38%).

$^1$H NMR (400 MHz, $CDCl_3$) δ: 6.11-6.03 (br. 1H, NH), 3.98 (d, 5.8 Hz, 4H), 3.25 (q-like, 6.3 Hz, 2H), 2.43-2.34 (m, 6H), 2.31 (t, 7.5 Hz, 4H), 2.14 (t-like, 7.6 Hz, 2H), 1.67-1.57 (m, 8H), 1.56-1.46 (m, 4H), 1.46-1.36 (m, 4H), 1.36-1.20 (m, 52H), 0.92-0.86 (m, 15H).

Example 18

Synthesis of Compound II-7

Compound II-7 was prepared according to method D to yield 235 mg of colorless oil (0.30 mmol, 30% for the last step).

$^1$H NMR (400 MHz, $CDCl_3$) δ: 5.95 (t-like, not well resolved, 5.3 Hz, 1H, NH), 3.98 (d, 5.8 Hz, 4H), 3.25 (q-like, 6.3 Hz, 2H), 2.42-2.35 (m, 6H), 2.31 (t, 7.5 Hz, 4H), 2.15 (t-like, 7.7 Hz, 2H), 1.68-1.58 (m, 8H), 1.54-1.38 (m, 8H), 1.36-1.18 (m, 44H), 0.92-0.86 (m, 15H).

Example 19

Synthesis of Compounds II-10 and II-15

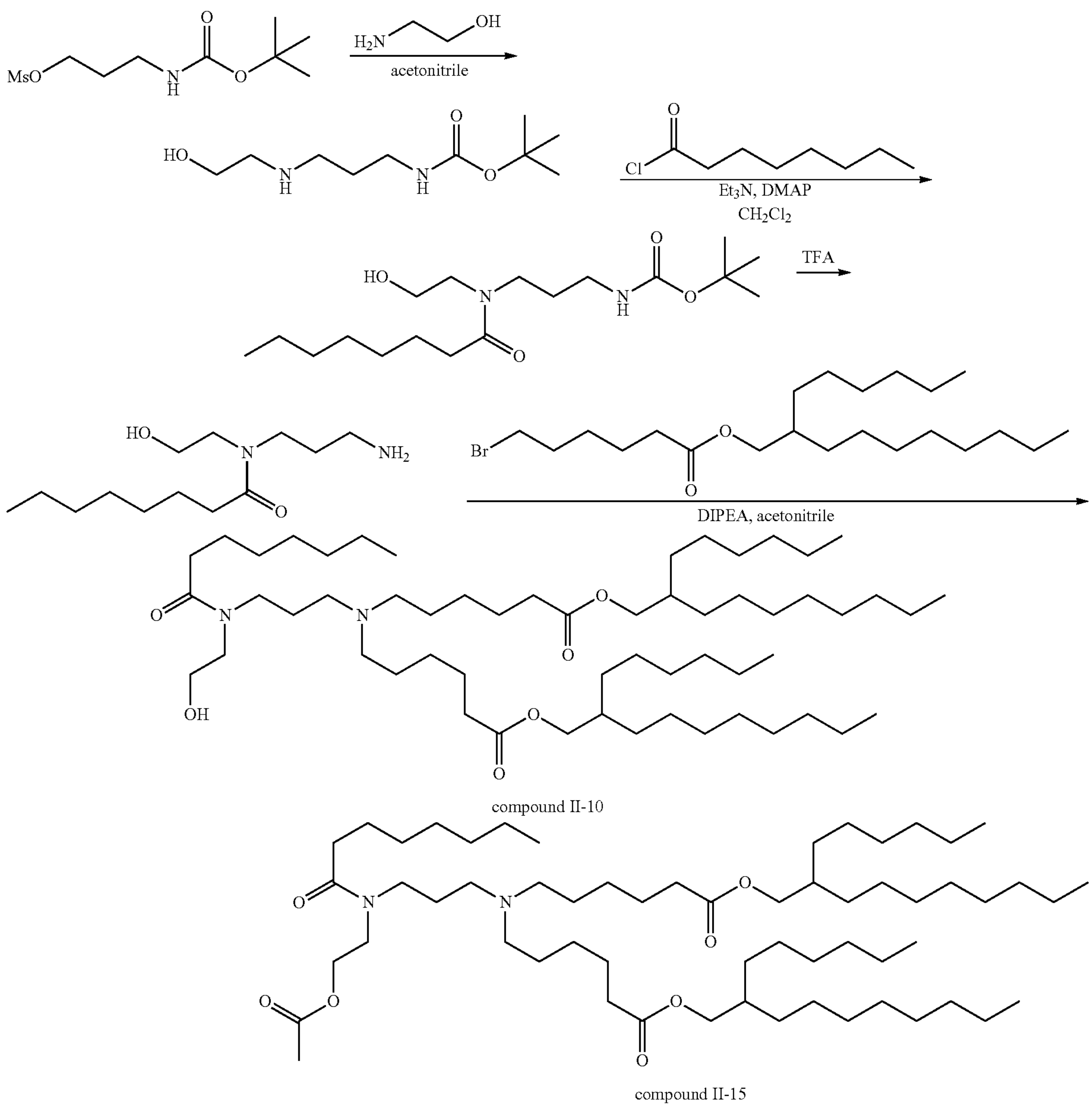

compound II-10 compound II-15

Synthesis of tert-Butyl (3-((2-hydroxyethyl)amino)propyl)carbamate 3-((tert-butoxycarbonyl)amino)propyl methanesulfonate (1.02 g, 4 mmol) was dissolved in anhydrous acetonitrile (10 mL) and 2-aminoethanol (5 eq, 20.5 mmol, 1.25 g, 1.24 mL) was added thereto. The mixture was heated at 75° C. for 18 hours. After heating, the reaction mixture was concentrated and the resulting residue was taken up in ethyl acetate (30 mL, two layers). Water was added to the mixture and the organic layer was separated. The aqueous layer was extracted with ethyl acetate (3×30 mL). The organic layer was dried over anhydrous sodium sulfate filtered, and concentrated to afford the crude product as slightly yellow oil (0.96 g). The crude product was purified by silica gel column chromatography (chloroform/methanol/concentrated ammonia, gradient from 90:10:0.5 to 80:20:3) to afford the desired product as oil (649 mg, 2.98 mmol, 74%).

Synthesis of tert-butyl (3-(N-(2-hydroxyethyl)octanamido)propyl)carbamate

A solution of octanoyl chloride (1.3 eq, 2.57 mmol, 419 mg, 439 μL) in dichloromethane (10 mL) was added via syringe to a solution of compound tert-butyl (3-((2-hydroxyethyl)amino)propyl)carbamate (1.98 mmol, 433 mg) and triethylamine (5 eq, 9.9 mmol, 1.00 g, 1.38 mL) and DMAP (5 mg) in dichloromethane (10 mL) at 10-20° C. over 5 minutes. The resulting mixture was allowed to warm and stirred overnight at room temperature followed by the addition of methanol (1 mL). Water was added and the layers were separated. The aqueous phase was extracted with dichloromethane (30 mL×1), dried over sodium sulfate, filtered and concentrated to yield oil/solid (0.764 g).

To a solution of the crude mixture (0.764 g) in ethanol (10 mL) was added potassium hydroxide (100 mg, ~1.5 mmol, in 1.5 mL of water). The resulting mixture was stirred at room temperature for 2.5 hours followed by concentration under reduced pressure. The resulting residue was diluted in ethyl acetate and to the mixture anhydrous sodium sulfate and anhydrous potassium carbonate was added. The mixture was filtered and concentrated to afford the desired product as clear colorless oil (650 mg, 1.88 mmol, 95%).

Synthesis of N-(3-aminopropyl)-N-(2-hydroxyethyl)octanamide

A solution of crude tert-butyl (3-(N-(2-hydroxyethyl) octanamido)propyl) carbamate (650 mg, 1.88 mmol) in dichloromethane (10 mL). Trifluoroacetic acid (40 mmol, 3 mL, 4.56 g) was added at room temperature under argon atmosphere. The reaction mixture was stirred at room temperature for 16 hours. The mixture was diluted with dichloromethane followed by the addition of water (40 mL), saturated aqueous sodium chloride (40 mL) and saturated aqueous sodium bicarbonate (40 mL). Solid sodium bicarbonate was slowly added with stirring until the pH of the mixture reached 9. Two phases were separated and the aqueous phase was extracted with dichloromethane (3×). Only small amount of the desired product was found in extracts, so the aqueous phase was concentrated under reduced pressure. The residue was taken up in isopropanol and filtered. The isopropanol filtrate was concentrated and a white solid was obtained (5.1 g). The resultant residue was taken up in a mixture of dichloromethane, methanol and triethylamine (~85:1:1) and filtered through a pad of silica. The filtrate was concentrated to afford the desired product as oil/solid (190 mg). The crude product was used in the next synthetic step without further purification.

Synthesis of Compound II-10 and Compound II-15

A solution of 2-hexyldecyl 6-bromohexanoate (1.0 g, 2.4 mmol), N-(3-aminopropyl)-N-(2-hydroxyethyl)octanamide (190 mg), N,N-diisopropylethylamine (2.6 mmol, 338 mg, 0.456 mL) and anhydrous acetonitrile (15 mL) was heated to 80° C. using an oil bath for 16 hours in a sealed pressure flask. The reaction mixture was concentrated and the resultant residue was taken up in a mixture of hexane/ethyl acetate (~19:1, 200 mL). The mixture was washed with water, dried over sodium sulfate, filtered and concentrated to afford brown oil. The crude product was purified by flash dry column chromatography on silica gel (gradient from 0 to 4% methanol in chloroform, 0 to 4%). A product was obtained as slightly yellow oil (37 mg) and tentatively assigned as compound 15 based on $^1$H NMR analysis.

$^1$H NMR (400 MHz, $CDCl_3$) δ: 4.23-4.13 (m, 2H), 3.976, 3.973 (two sets of doublets, 5.8 Hz, 4H), 3.59-3.53 (m, 2H), 3.37-3.29 (m, 2H), 2.41-2.28 (m, 12H), 2.07, 2.05 (two sets of singlet, 3H), 1.71-1.58 (m, 10H), 1.49-1.38 (m, 4H), 1.37-1.10 (58H), 0.92-0.86 (m, 15H).

Example 20

Synthesis of Compound II-12

Compound II-12 was prepared according to method G to yield 34 mg of colorless oil.

$^1$H NMR (400 MHz, $CDCl_3$) δ: 3.976, 3.974 (two sets of doublets, 5.8 Hz, 4H), 3.33-3.27 (m, 2H), 3.26-3.19 (m, 2H), 2.42-2.35 (m, 6H), 2.31 (t, 7.5 Hz, 2H), 2.30 (t, 7.5 Hz, 2H), 2.09, 2.08 (two sets of singlet, 3H), 1.71-1.59 (m, 8H), 1.59-1.49 (m, 2H), 1.48-1.39 (m, 4H), 1.37-1.19 (m, 62H), 0.92-0.86 (m, 15H).

Example 21

Synthesis of Compound II-14

Compound II-14 was prepared according to method D (in a similar manner to compound II-3) to yield 241 mg of colorless oil (0.31 mmol, 41%).

$^1$H NMR (400 MHz, $CDCl_3$) δ: 3.97 (dd, 5.8 Hz, 1.1 Hz, 4H), 3.36 (t-like, 7.5 Hz, 1H), 3.30 (t-like, 7.5 Hz, 1H), 2.98, 2.91 (two sets of singlet, 3H), 2.41-2.35 (m, 6H), 2.34-2.26 (m, 6H), 1.71-1.58 (m, 10H), 1.48-1.38 (m, 4H), 1.37-1.18 (m, 44H), 0.92-0.86 (m, 15H).

Example 22

Synthesis of Compound II-16

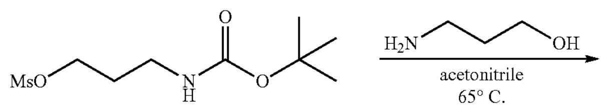

-continued

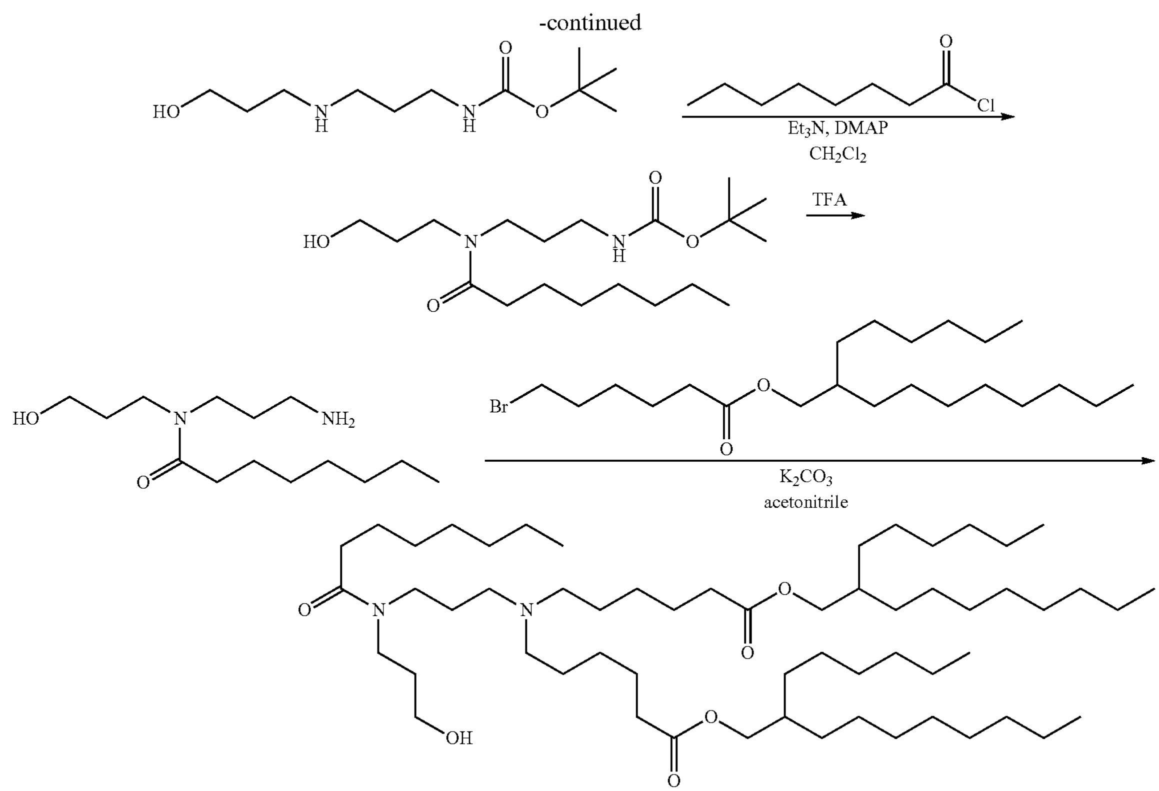

Synthesis of tert-butyl (3-((3-hydroxypropyl)amino)propyl)carbamate 3-((tert-Butoxycarbonyl)amino)propyl methanesulfonate (1.05 g, 4.1 mmol) and 3-amino-1-propanol (5 eq, 20.5 mmol, 1.54 g, 1.57 mL) were dissolved in acetonitrile (10 mL). The mixture was then stirred at 65° C. overnight.

After water (10-20 mL) was added to the mixture, the organic layer was separated and the aqueous layer was extracted with ethyl acetate (3×30 mL). The organic extract was dried over sodium sulfate, filtered, and concentrated to afford colorless oil (0.75 g). The crude product was purified by silica gel column chromatography (chloroform/methanol/concentrated ammonia, gradient from 90:10:0.5 to 80:20:3). Fractions containing the product were combined and concentrated. The resultant residue was dissolved in ethanol and filtered through cotton. The filtrate was concentrated to afford the desired product (591 mg, 2.54 mmol, 64%).

Synthesis of tert-butyl (3-(N-(3-hydroxypropyl)octanamido)propyl)carbamate

A solution of octanoyl chloride (1 eq, 1.6 mmol, 260 mg, 273 μL) in dichloromethane (10 mL) was added via syringe to a solution of tert-butyl (3-((3-hydroxypropyl)amino)propyl)carbamate (1.6 mmol, 371 mg) and triethylamine (5 eq, 8 mmol, 808 mg, 1.11 mL) and DMAP (5 mg) in dichloromethane (10 mL) at 5° C. in over 5 minutes. The mixture was allowed to warm to room temperature and stirred for 3.5 hours, followed by the addition of methanol (1 mL). After an additional 1 hour of stirring, water was added and two layers were separated. The aqueous phase was extracted with dichloromethane (30 mL×1). The extract was dried over sodium sulfate and concentrated to afford the desired product as colorless oil (0.59 g, 1.64 mmol, 100%).

Synthesis of N-(3-aminopropyl)-N-(3-hydroxypropyl)octanamide

In a round-bottomed flask equipped with a stir bar and a rubber septum under an argon atmosphere was placed tert-butyl (3-(N-(3-hydroxypropyl)octanamido)propyl)carbamate (1.6 mmol, 590 mg) in dichloromethane (10 mL). Trifluoroacetic acid (3 mL) was added to the mixture and the reaction mixture was stirred at room temperature for 3.5 hours. After stirring, the reaction mixture was concentrated to remove solvent.

The resultant residue was dissolved in dichloromethane and concentrated again to afford colorless oil (1.1 g). The oil was dissolved in dichloromethane and filtered through sodium bicarbonate powder. The filtrate was concentrated to afford an oil (1.1 g). The crude product was used in the next synthetic step without further purification.

Synthesis of Compound II-16

A mixture of 2-hexyldecyl 6-bromohexanoate (2.59 mmol, 1.09 g), N-(3-aminopropyl)-N-(3-hydroxypropyl)octanamide (1.1 g), N,N-diisopropylethylamine (2.8 mmol, 361 mmg, 0.487 mL), potassium carbonate (2.8 mmol, 386 mg) and anhydrous acetonitrile (15 mL) was heated to 83° C. using an oil bath for 16 hours in a sealed pressure flask. The reaction mixture was concentrated and the residue was taken up in a mixture of hexane/ethyl acetate (~75:25) with 0.5% triethylamine (20 mL). The mixture was filtered through a pad of silica and the pad was washed with a mixture of hexane/ethyl acetate/triethylamine (100 mL, 4:1:0.1). The filtrate was concentrated and the residue was purified again by flash dry column chromatography on silica gel (gradient from 0 to 4% methanol in chloroform) to afford the desired product as a slightly yellow oil (240 mg, 0.26 mmol, 20%).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/491,664, filed Apr. 28, 2017, U.S. Provisional Patent Application No. 62/491,659, filed Apr. 28, 2017, U.S. Provisional Patent Application No. 62/546,227, filed Aug. 16, 2017, and U.S. Provisional Patent Application No. 62/595,497, filed Dec. 6, 2017, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having the following structure (II):

(II)

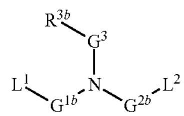

or a pharmaceutically acceptable salt or stereoisomer thereof, wherein:

$L^1$ is —O(C═O)$R^1$, —(C═O)O$R^1$, —C(═O)$R^1$, —O$R^1$, —S(O)$_x$$R^1$, —S—S$R^1$, —C(═O)S$R^1$, —SC(═O)$R^1$, —N$R^a$C(═O)$R^1$, —C(═O)N$R^b$$R^c$, —N$R^a$C(═O)N$R^b$$R^c$, —OC(═O)N$R^b$$R^c$ or —N$R^a$C(═O)O$R^1$;

$L^2$ is —O(C═O)$R^2$, —(C═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^e$$R^f$, —N$R^d$C(═O)N$R^e$$R^f$, —OC(═O)N$R^e$$R^f$, —N$R^d$C(═O)O$R^2$, or a direct bond to $R^2$;

$G^{1b}$ and $G^{2b}$ are each independently $C_1$-$C_{12}$ alkylene or $C_2$-$C_{12}$ alkenylene;

$G^3$ is $C_1$-$C_{24}$ alkylene, $C_2$-$C_{24}$ alkenylene, $C_3$-$C_8$ cycloalkylene or $C_3$-$C_8$ cycloalkenylene;

$R^a$, $R^b$, $R^d$ and $R^e$ are each independently H, $C_1$-$C_{12}$ alkyl or $C_2$-$C_{12}$ alkenyl;

$R^c$ and $R^f$ are each independently $C_1$-$C_{12}$ alkyl or $C_2$-$C_{12}$ alkenyl;

$R^1$ and $R^2$ each, independently, have the following structure:

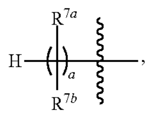

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ are each independently branched and independently comprise from 6 to 20 carbon atoms;

$R^{3b}$ is —N$R^{4b}$C(═O)$R^{5b}$;

$R^{4b}$ is H, $C_1$-$C_{12}$ alkyl or $C_2$-$C_{12}$ alkenyl;

$R^{5b}$ is $C_2$-$C_{12}$ alkyl or $C_2$-$C_{12}$ alkenyl when $R^{4b}$ is H; or $R^{5b}$ is $C_1$-$C_{12}$ alkyl or $C_2$-$C_{12}$ alkenyl when $R^{4b}$ is $C_1$-$C_{12}$ alkyl or $C_2$-$C_{12}$ alkenyl; and x is 0, 1 or 2, and wherein each alkyl, alkenyl, alkylene, alkenylene, cycloalkylene, cycloalkenylene, aryl and aralkyl is independently substituted or unsubstituted.

2. The compound of claim 1, wherein $G^3$ is $C_3$-$C_{12}$ alkylene.

3. The compound of claim 1, having the following structure (IIA):

(IIA)

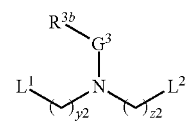

wherein y2 and z2 are each independently integers ranging from 1 to 12.

4. The compound of claim 1, wherein $L^1$ is —O(C═O)$R^1$, —(C═O)O$R^1$ or —C(═O)N$R^b$$R^c$, and $L^2$ is —O(C═O)$R^2$, —(C═O)O$R^2$ or —C(═O)N$R^e$$R^f$.

5. The compound of claim 4, having one of the following structures (IIB) or (IIC):

(IIB)

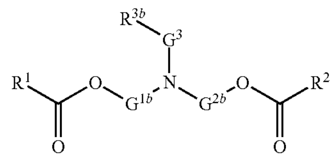

or (IIC)

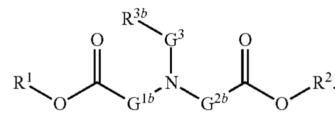

6. The compound of claim 4, having one of the following structures (IID) or (IIE):

(IID)

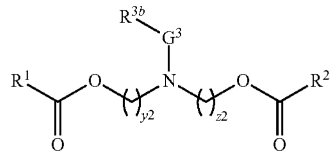

or (IIE)

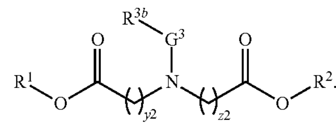

7. The compound of claim 3, wherein y2, and z2 are each independently an integer ranging from 4 to 10.

8. The compound of claim 1, wherein $R^1$ and $R^2$ are each, independently, branched $C_6$-$C_{24}$ alkyl.

9. The compound of claim 1, wherein a is an integer from 8 to 12.

10. The compound of claim 1, wherein at least one occurrence of $R^{7b}$ is $C_1$-$C_8$ alkyl.

11. The compound of claim 10, wherein $C_1$-$C_8$ alkyl is methyl, ethyl, n-propyl, iso-propyl, n-butyl, iso-butyl, tert-butyl, n-hexyl or n-octyl.

12. The compound of claim 1, wherein $R^1$ and $R^2$ independently has one of the following structures:

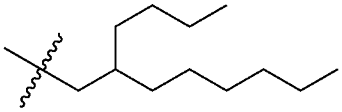
;

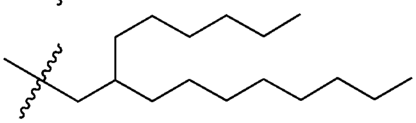
;

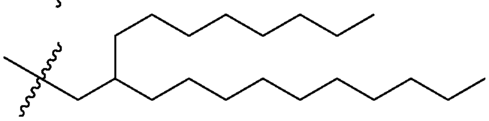
;

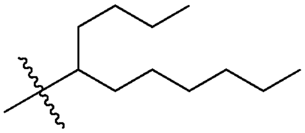
;

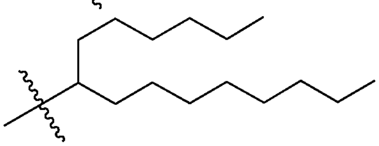
;

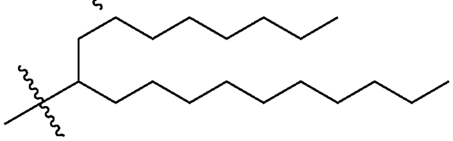
;

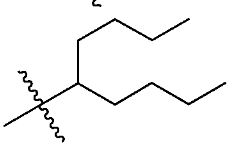
;

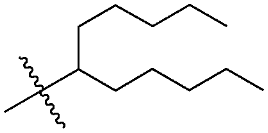
;

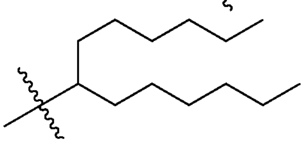
; or

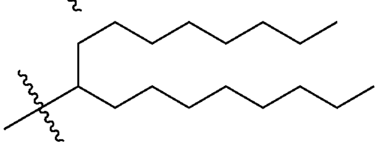
.

13. The compound of claim 1, wherein $R^{4b}$ is methyl, ethyl, propyl, or octyl.

14. The compound of claim 13, wherein $R^{4b}$ and $R^{5b}$ are independently optionally substituted with one or more substituents selected from the group consisting of $-OR^g$, $-NR^gC(=O)R^h$, $-C(=O)NR^gR^h$, $-C(=O)R^h$, $-OC(=O)R^h$, $-C(=O)OR^h$ and $OR^iOH$, wherein:

$R^g$ is, at each occurrence, independently H or $C_1$-$C_6$ alkyl;

$R^h$ is, at each occurrence, independently $C_1$-$C_6$ alkyl; and $R^i$ is, at each occurrence, independently $C_1$-$C_6$ alkylene.

15. The compound of claim 13, wherein $R^{5b}$ is methyl, ethyl, propyl, heptyl or octyl.

16. The compound of claim 1, wherein $R^{3b}$ has one of the following structures:

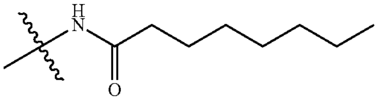
;

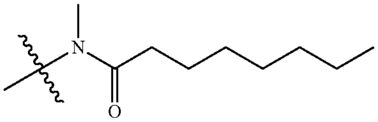
;

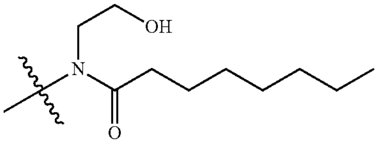
;

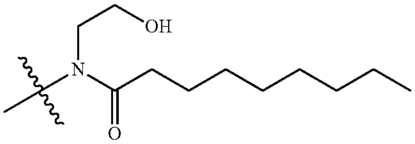
;

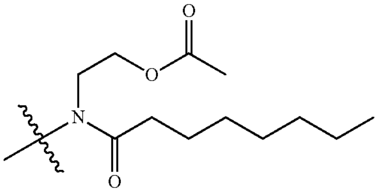
;

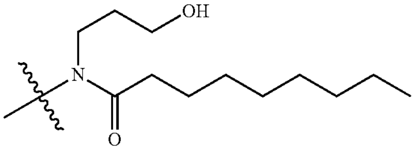
;

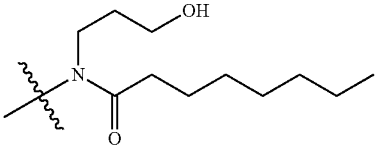
;

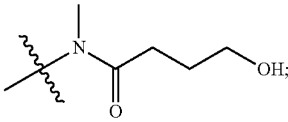
;

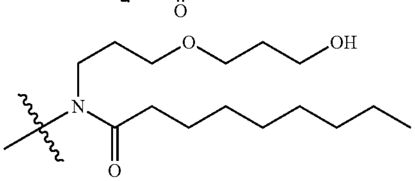
;

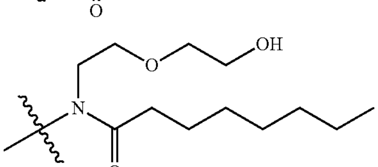
;

-continued
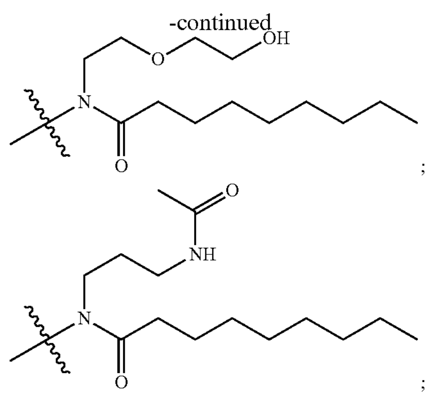
;
;
-continued
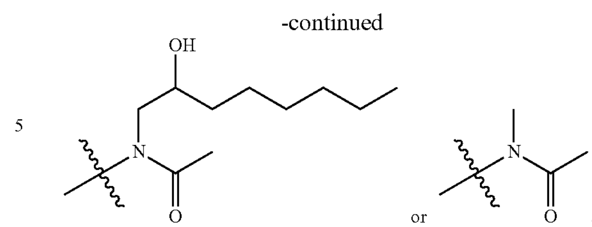
or .
17. The compound of claim 1, having one of the following structures:
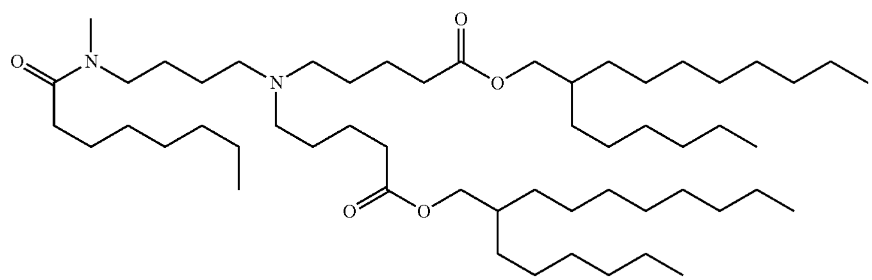
;
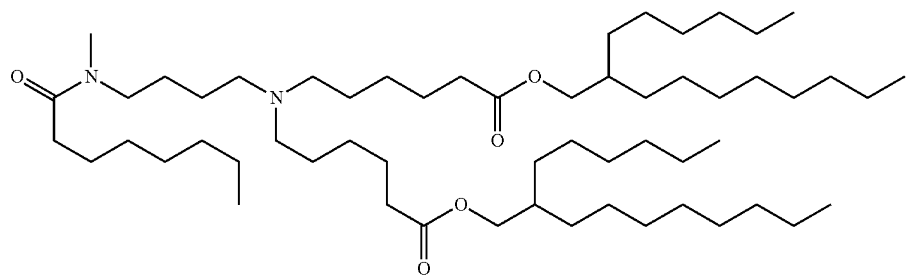
;
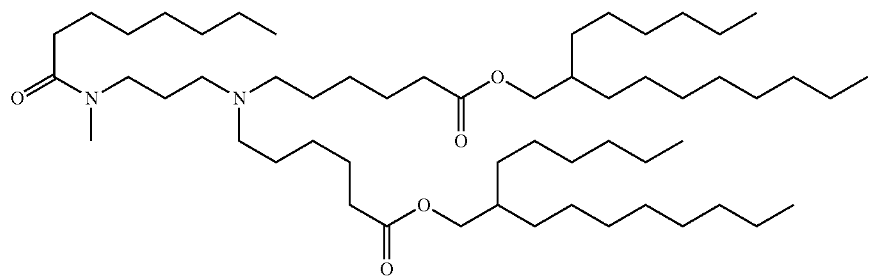
;
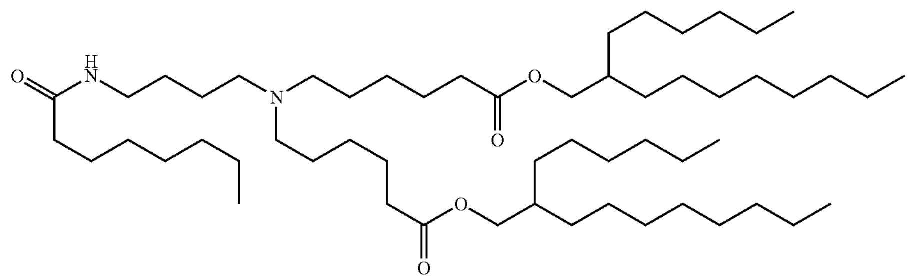
;

-continued
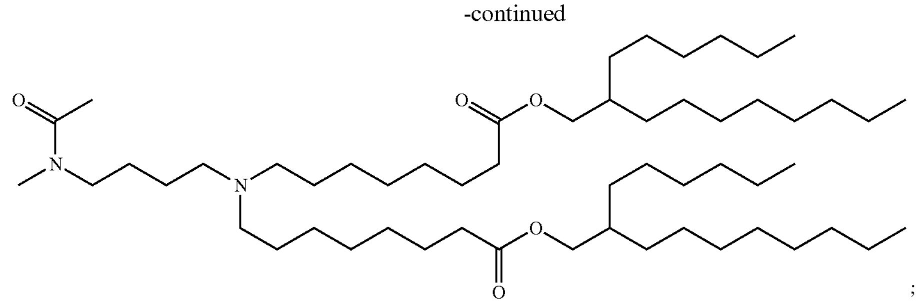
;
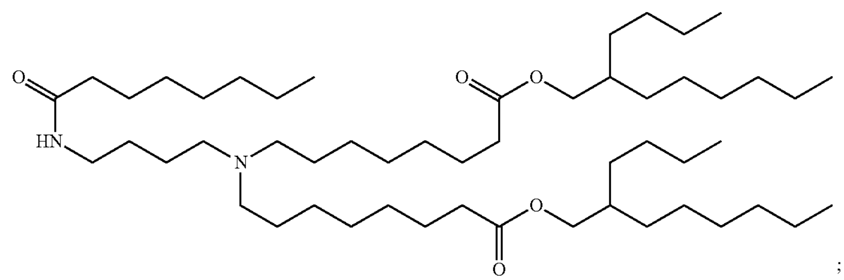
;
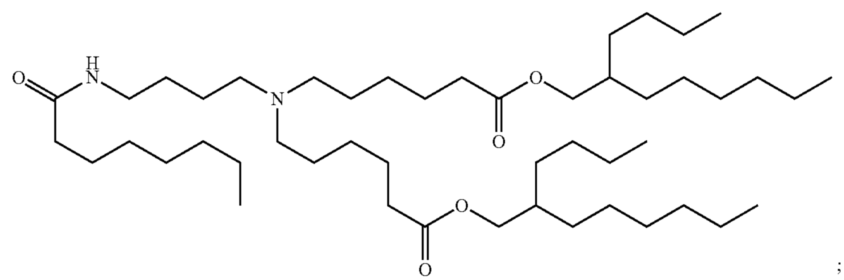
;
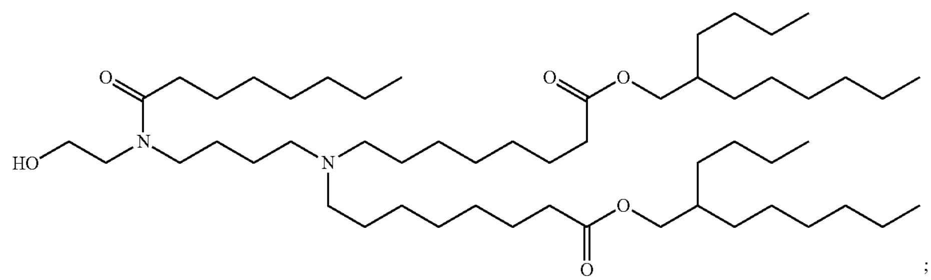
;
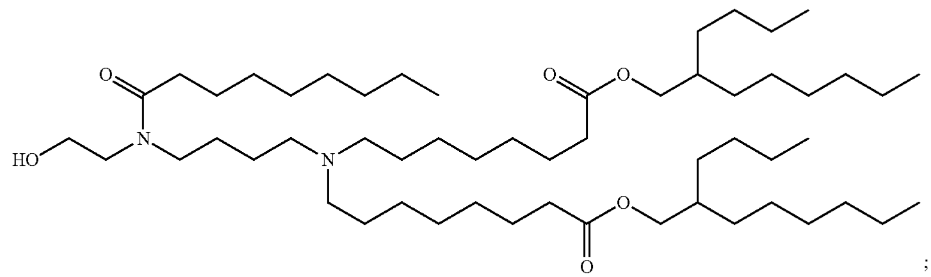
;
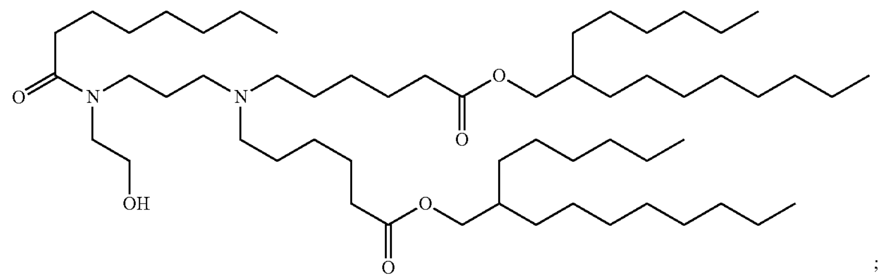
;

-continued
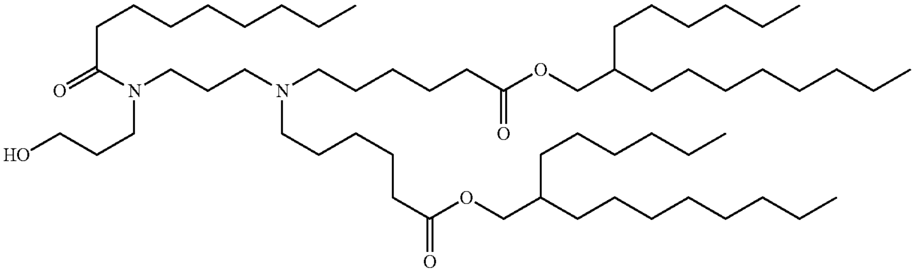
;
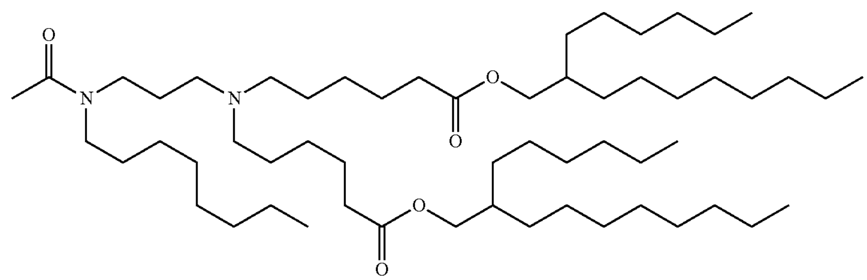
;
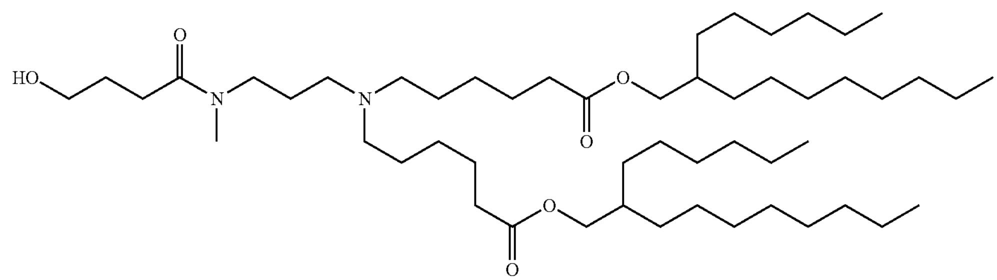
;
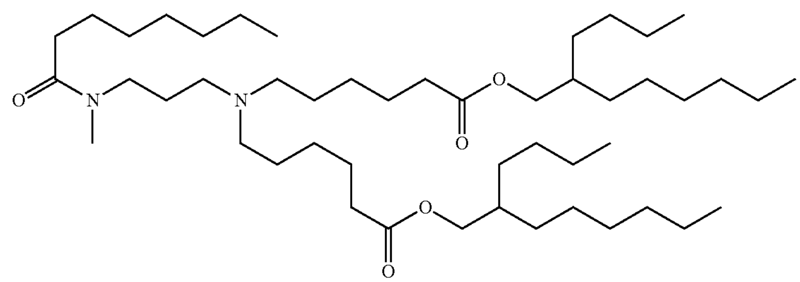
;
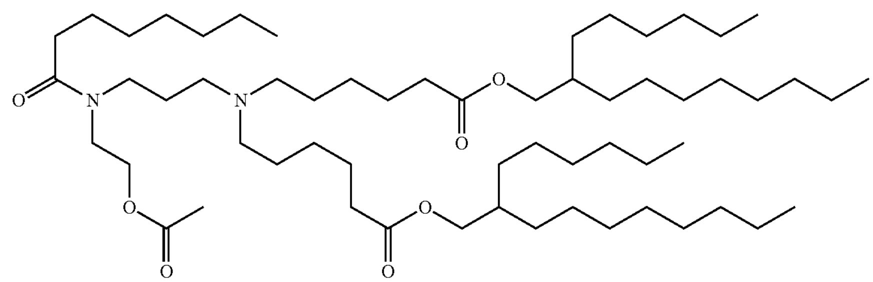
;
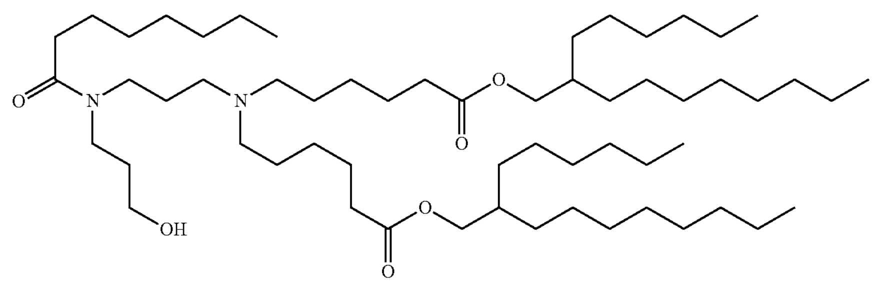 [SMILES: CCCCCCCCC(CCCCCC)COC(=O)CCCCCN(CCCCCC(=O)OCC(CCCCCC)CCCCCCCC)CCCN(CCCO)C(=O)CCCCCCC]
;

-continued

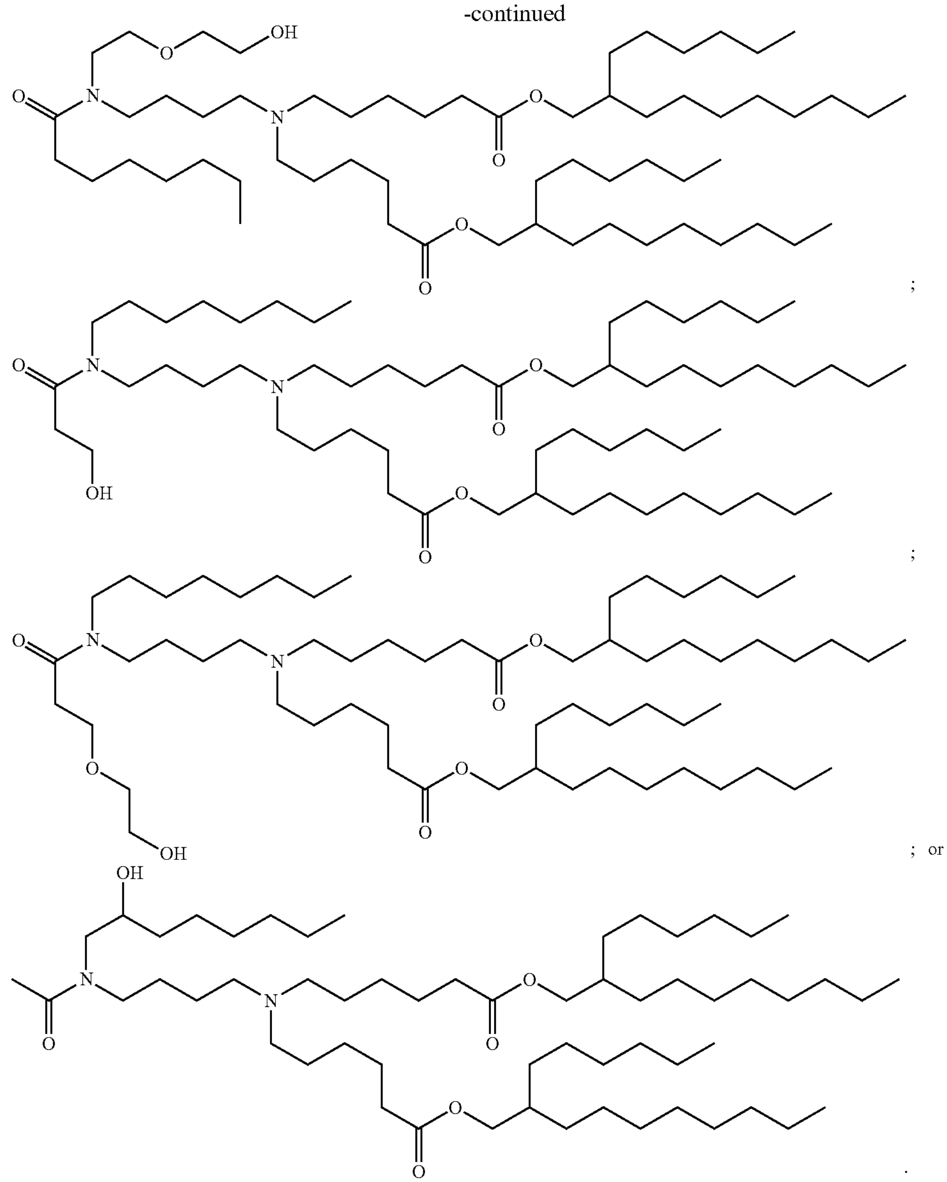

; ; ; or .

18. A composition comprising the compound of claim 1 and a therapeutic agent.

19. The composition of claim 18, wherein the therapeutic agent comprises a nucleic acid.

20. The composition of claim 19, wherein the nucleic acid is selected from antisense and messenger RNA.

21. A lipid nanoparticle comprising a compound of claim 1.

22. A pharmaceutical composition comprising the lipid nanoparticle of claim 21 and a pharmaceutically acceptable diluent or excipient.

* * * * *